(12) United States Patent
Sharps et al.

(10) Patent No.: US 6,602,248 B1
(45) Date of Patent: *Aug. 5, 2003

(54) METHODS FOR REPAIRING DAMAGED INTERVERTEBRAL DISCS

(75) Inventors: Lewis Sharps, Bryn Mawr, PA (US); David C. Hovda, Mountain View, CA (US); Jean Woloszko, Mountain View, CA (US); Hira V. Thapliyal, Los Altos, CA (US); Philip E. Eggers, Dublin, OH (US)

(73) Assignee: Arthro Care Corp., Sunnyvale ( * ) Notice: Subject to any disclaimer, the term of this patent is extended or adjusted under 35 U.S.C. 154(b) by 0 days.

This patent is subject to a terminal disclaimer.

(21) Appl. No.: 09/676,194

(22) Filed: Sep. 28, 2000

Related U.S. Application Data

(63) Continuation-in-part of application No. PCT/US00/13706, filed on May 17, 2000, which is a continuation of application No. 09/316,472, filed on May 21, 1999, which is a continuation-in-part of application No. 09/295,687, filed as application No. 09/054,323 on Apr. 2, 1998, and a continuation-in-part of application No. 09/268,616, filed on Mar. 15, 1999, which is a continuation-in-part of application No. 08/990,374, filed on Dec. 15, 1997, which is a continuation-in-part of application No. 08/485,219, filed on Jun. 7, 1995, which is a continuation-in-part of application No. 09/026,851, filed on Feb. 20, 1999, and a continuation-in-part of application No. 08/690,159, filed on Jul. 18, 1996.

(60) Provisional application No. 60/224,107, filed on Aug. 9, 2000.

(51) Int. Cl.$^7$ .............................................. A61B 18/14
(52) U.S. Cl. ........................ 606/32; 606/41; 604/35; 604/114; 607/105; 607/113
(58) Field of Search ........................ 606/32, 34, 41, 606/49; 607/99, 105, 113; 604/35, 114; 128/898

(56) References Cited

U.S. PATENT DOCUMENTS 6,073,051 A * 6/2000 Sharkey et al. ............... 606/27
6,277,112 B1 * 8/2001 Underwood et al. ......... 604/114

* cited by examiner

Primary Examiner—Lee Cohen
(74) Attorney, Agent, or Firm—John T. Raffle; Richard R. Batt

(57) ABSTRACT

Apparatus and methods for treating an intervertebral disc by ablation of disc tissue. A method of the invention includes positioning at least one active electrode within the intervertebral disc, and applying at least a first high frequency voltage between the active electrode(s) and one or more return electrode(s), wherein the volume of the nucleus pulposus is decreased, pressure exerted by the nucleus pulposus on the annulus fibrosus is reduced, and discogenic pain of a patient is alleviated. In other embodiments, a curved or steerable probe is guided to a specific target site within a disc to be treated, and the disc tissue at the target site is ablated by application of at least a first high frequency voltage between the active electrode(s) and one or more return electrode(s). A method of making an electrosurgical probe is also disclosed.

57 Claims, 47 Drawing Sheets

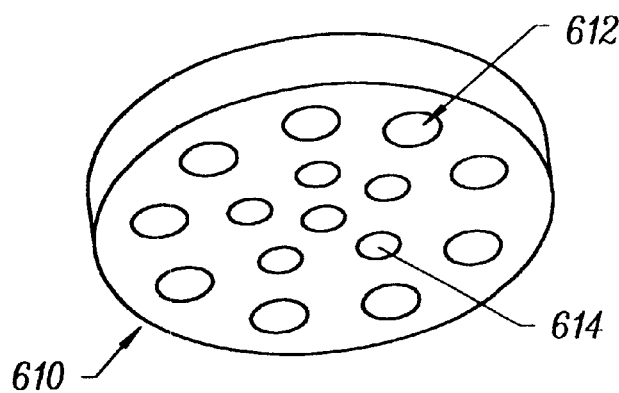
FIG. 14A
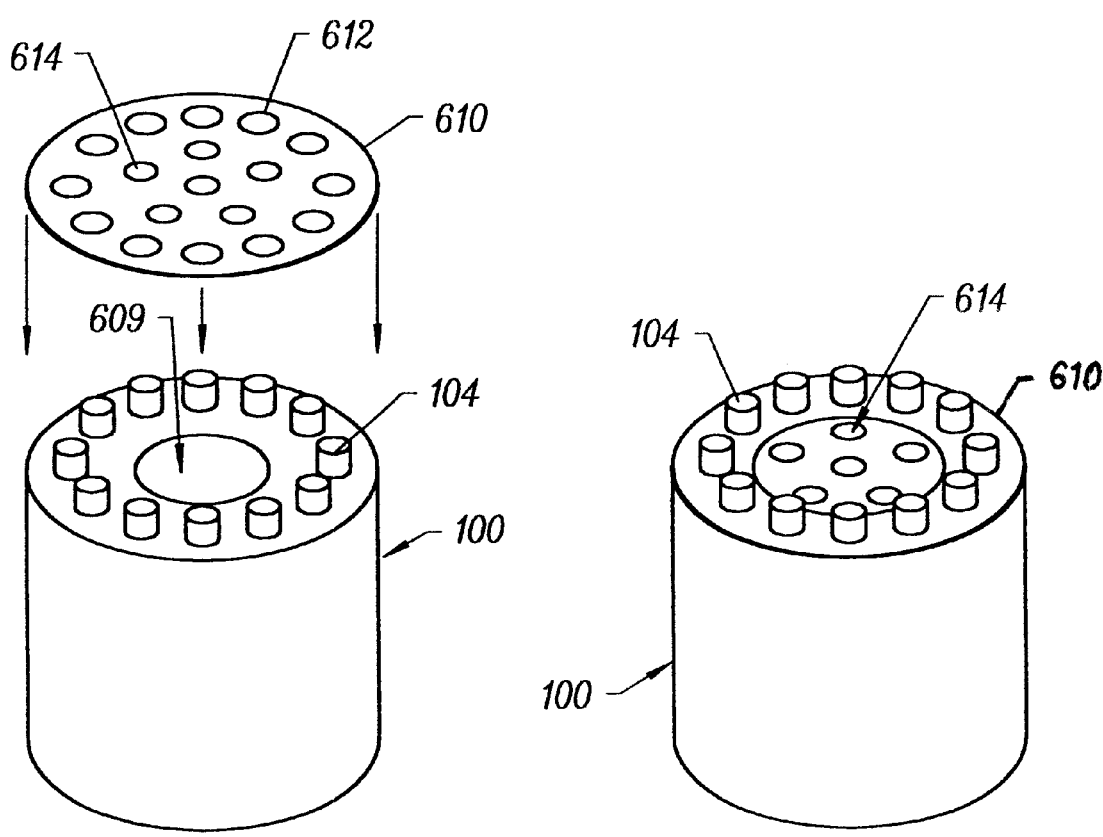
FIG. 14B
FIG. 14C

METHODS FOR REPAIRING DAMAGED INTERVERTEBRAL DISCS

CROSS-REFERENCES TO RELATED APPLICATIONS

The present invention claims priority from U.S. Provisional Application No. 60/224,107, filed Aug. 9, 2000, and from PCT Application No. 00/13706, filed May 17, 2000, and from U.S. patent application Ser. No. 09/316,472, filed May 21, 1999, which is a continuation-in-part of U.S. patent application Ser. No. 09/295,687, filed Apr. 21, 1999 and U.S. patent application Ser. Nos. 09/054,323 and 09/268,616, filed Apr. 2, 1998 and Mar. 15, 1999, respectively, each of which are continuation-in-parts of U.S. patent application Ser. No. 08/990,374, filed Dec. 15, 1997, which is a continuation-in-part of U.S. patent application Ser. No. 08/485,219, filed on Jun. 7, 1995, the complete disclosures of which are incorporated herein by reference for all purposes. This application is also a continuation-in-part of U.S. patent application Ser. No. 09/026,851, filed Feb. 20, 1999, which is a continuation-in-part of U.S. patent application Ser. No. 08/690,159, filed Jul. 18, 1996, the complete disclosure of which is incorporated herein by reference for all purposes.

The present invention is related to commonly assigned U.S. patent application Ser. No. 09/181,926, filed Oct. 28, 1998, U.S. patent application Ser. No. 09/130,804, filed Aug. 7, 1998, U.S. patent application Ser. No. 09/058,571, filed on Apr. 10, 1998, U.S. patent application Ser. No. 09/248,763, filed Feb. 12, 1999, U.S. patent application Ser. No. 09/026,698, filed Feb. 20, 1998, U.S. patent application Ser. No. 09/074,020, filed on May 6, 1998, U.S. patent application Ser. No. 09/010,382, filed Jan. 21, 1998, U.S. patent application Ser. No. 09/032,375, filed Feb. 27, 1998, U.S. patent application Ser. Nos. 08/977,845, filed on Nov. 25, 1997, 08/942,580, filed on Oct. 2, 1997, U.S. patent application Ser. No. 08/753,227, filed on Nov. 22, 1996, U.S. patent application Ser. No. 08/687792, filed on Jul. 18, 1996, and PCT International Application, U.S. National Phase Ser. No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,697,882, filed Nov. 22, 1995, the complete disclosure of which is incorporated herein by reference for all purposes.

BACKGROUND OF THE INVENTION

The present invention relates to a medical apparatus having a distal curved configuration which avoids contact of the apparatus distal end with an introducer device. The present invention also relates to the field of electrosurgery, and more particularly to surgical devices and methods which employ high frequency electrical energy to treat tissue in regions of the spine. The present invention is particularly suited for the treatment of the discs, cartilage, ligaments, and other tissue within the vertebral column.

The major causes of persistent, often disabling, back pain are disruption of the disc annulus, chronic inflammation of the disc, contained and non-contained herniation, and relative instability of the vertebral bodies surrounding a given disc, such as the instability that often occurs due to a stretching of the interspinous tissue surrounding the vertebrae. Intervertebral discs mainly function to cushion and tether the vertebrae, while the interspinous tissue (i.e., tendons and cartilage, and the like) function to support the vertebrae so as to provide flexibility and stability to the patient's spine.

Spinal discs comprise a central hydrophilic cushion, the nucleus pulposus, surrounded by a multi-layered fibrous ligament, the annulus fibrosus. As discs degenerate, they lose their water content and height, bringing the adjoining vertebrae closer together. This results in a weakening of the shock absorption properties of the disc and a narrowing of the nerve openings in the sides of the spine which may pinch these nerves. This disc degeneration can eventually cause back and leg pain. Weakness in the annulus from degenerative discs or disc injury can allow fragments of nucleus pulposus from within the disc space to migrate through the annulus fibrosus and into the spinal canal. There, displaced nucleus pulposus tissue, or protrusion of the annulus fibrosus, e.g., due to herniation, may impinge on spinal nerves or nerve roots. A weakening of the annulus fibrosus can cause the disc to bulge, e.g., a contained herniation, and the mere proximity of the nucleus pulposus or the damaged annulus to a nerve can cause direct pressure against the nerve, resulting in pain and sensory and motor deficit.

Often, inflammation from disc herniation can be treated successfully by non-surgical means, such as rest, therapeutic exercise, oral anti-inflammatory medications or epidural injection of corticosteroids. Such treatments result in a gradual but progressive improvement in symptoms and allow the patient to avoid surgical intervention.

In some cases, the disc tissue is irreparably damaged, thereby necessitating removal of a portion of the disc or the entire disc to eliminate the source of inflammation and pressure. In more severe cases, the adjacent vertebral bodies must be stabilized following excision of the disc material to avoid recurrence of the disabling back pain. One approach to stabilizing the vertebrae, termed spinal fusion, is to insert an interbody graft or implant into the space vacated by the degenerative disc. In this procedure, a small amount of bone may be grafted and packed into the implants. This allows the bone to grow through and around the implant, fusing the vertebral bodies and preventing reoccurrence of the symptoms.

Until recently, surgical spinal procedures resulted in major operations and traumatic dissection of muscle and bone removal or bone fusion. To overcome the disadvantages of traditional traumatic spine surgery, minimally invasive spine surgery was developed. In endoscopic spinal procedures, the spinal canal is not violated and therefore epidural bleeding with ensuing scarring is minimized or completely avoided. In addition, the risk of instability from ligament and bone removal is generally lower in endoscopic procedures than with open procedures. Further, more rapid rehabilitation facilitates faster recovery and return to work.

Minimally invasive techniques for the treatment of spinal diseases or disorders include chemonucleolysis, laser techniques, and mechanical techniques. These procedures generally require the surgeon to form a passage or operating corridor from the external surface of the patient to the spinal disc(s) for passage of surgical instruments, implants and the like. Typically, the formation of this operating corridor requires the removal of soft tissue, muscle or other types of tissue depending on the procedure (i.e., laparascopic, thoracoscopic, arthroscopic, back, etc.). This tissue is usually removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments might sever blood vessels within this tissue, usually causing profuse bleeding that obstructs the surgeon's view of the target site.

Once the operating corridor is established, the nerve root is retracted and a portion or all of the disc is removed with mechanical instruments, such as a pituitary rongeur. In addition to the above problems with mechanical instruments, there are serious concerns because these instruments are not precise, and it is often difficult, during the procedure, to differentiate between the target disc tissue, and other structures within the spine, such as bone, cartilage, ligaments, nerves and non-target tissue. Thus, the surgeon must be extremely careful to minimize damage to the cartilage and bone within the spine, and to avoid damaging nerves, such as the spinal nerves and the dura mater surrounding the spinal cord.

Lasers were initially considered ideal for spine surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, bones, ligaments and spinal nerves often lie within close proximity of the spinal disc, it is essential to maintain a minimum depth of tissue damage, which cannot always be ensured with a laser.

Monopolar and bipolar radiofrequency devices have been used in limited roles in spine surgery, such as to cauterize severed vessels to improve visualization. Monopolar devices, however, suffer from the disadvantage that the electric current will flow through undefined paths in the patient's body, thereby increasing the risk of undesirable electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue or neighboring peripheral nerves.

Other disadvantages of conventional RF devices, particularly monopolar devices, is nerve stimulation and interference with nerve monitoring equipment in the operating room. In addition, these devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Many patients experience discogenic pain due to defects or disorders of intervertebral discs. Such disc defects include annular fissures, fragmentation of the nucleus pulposus, and contained herniation. A common cause of pain related to various disc disorders is compression of a nerve root by the disc. In many patients for whom major spinal surgery is not indicated, discogenic pain naturally diminishes in severity over an extended period of time, perhaps several months. There is a need for a minimally invasive method to treat such patients in order to alleviate the chronic, and often debilitating, pain associated with spinal nerve root compression. The instant invention provides methods for decompressing nerve roots by ablation of disc tissue at relatively low temperatures during a percutaneous procedure, wherein the volume of the disc is decreased and discogenic pain is alleviated.

SUMMARY OF THE INVENTION

The present invention provides systems, apparatus, and methods for selectively applying electrical energy to structures within a patient's body, such as the intervertebral disc. The systems and methods of the present invention are useful for shrinkage, ablation, resection, aspiration, and/or hemostasis of tissue and other body structures in open and endoscopic spine surgery. In particular, the present invention includes a method and system for debulking, ablating, and shrinking the disc.

The present invention further relates to an electrosurgical probe including an elongated shaft having first and second curves in the distal end portion of the shaft, wherein the shaft can be rotated within an intervertebral disc to contact fresh tissue of the nucleus pulposus. The present invention also relates to an electrosurgical probe including an elongated shaft, wherein the shaft distal end can be guided to a specific target site within a disc, and the shaft distal end is adapted for localized ablation of targeted disc tissue. The present invention further relates to a probe having an elongated shaft, wherein the shaft includes an active electrode, an insulating collar, and an outer shield, and wherein the active electrode includes a head having an apical spike and a cusp. The present invention still further relates to a method for ablating disc tissue with an electrosurgical probe, wherein the probe includes an elongated shaft, and the shaft distal end is guided to a specific target site within a disc.

In one aspect, the present invention provides a method of treating a herniated intervertebral disc. The method comprises positioning at least one active electrode within the intervertebral disc. High frequency voltage is applied between the active electrode(s) and one or more return electrode(s) to debulk, ablate, coagulate and/or shrink at least a portion of the nucleus pulposus and/or annulus. The high frequency voltage effects a controlled depth of thermal heating to reduce the water content of the nucleus pulposus, thereby debulking the nucleus pulposus and reducing the internal pressure on the annulus fibrosus.

In an exemplary embodiment, an electrically conductive media, such as isotonic saline or an electrically conductive gel, is delivered to the target site within the intervertebral disc prior to delivery of the high frequency energy. The conductive media will typically fill the entire target region such that the active electrode(s) are submerged throughout the procedure. In other embodiments, the extracellular conductive fluid (e.g., the nucleus pulposus) in the patient's disc may be used as a substitute for, or as a supplement to, the electrically conductive media that is applied or delivered to the target site. For example, in some embodiments, an initial amount of conductive media is provided to initiate the requisite conditions for ablation. After initiation, the conductive fluid already present in the patient's tissue is used to sustain these conditions.

In another aspect, the present invention provides a method of treating a disc having a contained herniation or fissure. The method comprises introducing an electrosurgical instrument into the patient's intervertebral disc either percutaneously or through an open procedure. The instrument is steered or otherwise guided into close proximity to the contained herniation or fissure and a high frequency voltage is applied between an active electrode and a return electrode so as to debulk the nucleus pulposus adjacent the contained herniation or fissure. In some embodiments a conductive fluid is delivered into the intervertebral disc prior to applying the high frequency voltage to ensure that sufficient conductive fluid exists for plasma formation and to conduct electric current between the active and return electrodes. Alternatively, the conductive fluid can be delivered to the target site during the procedure. The heating delivered through the electrically conductive fluid debulks the nucleus pulposus, and reduces the pressure on the annulus fibrosus so as to reduce the pressure on the affected nerve root and alleviate neck and back pain.

In another aspect, the present invention provides a method for treating degenerative intervertebral discs. The active electrode(s) are advanced into the target disc tissue in an ablation mode, where the high frequency voltage is sufficient to ablate or remove the nucleus pulposus through molecular dissociation or disintegration processes. In these embodiments, the high frequency voltage applied to the active electrode(s) is sufficient to vaporize an electrically conductive fluid (e.g., gel, saline and/or intracellular fluid) between the active electrode(s) and the tissue. Within the vaporized fluid, an ionized plasma is formed and charged particles (e.g., electrons) cause the molecular breakdown or disintegration of several cell layers of the nucleus pulposus. This molecular dissociation is accompanied by the volumetric removal of the tissue. This process can be precisely controlled to effect the volumetric removal of tissue as thin as 10 microns to 150 microns with minimal heating of, or damage to, surrounding or underlying tissue structures. A more complete description of this phenomenon is described in commonly assigned U.S. Pat. No. 5,697,882 the complete disclosure of which is incorporated herein by reference.

An apparatus according to the present invention generally includes a shaft having proximal and distal end portions, an active electrode at the distal end and one or more connectors for coupling the active electrode to a source of high frequency electrical energy. The probe or catheter may assume a wide variety of configurations, with the primary purpose being to introduce the electrode assembly into the patient's disc (in an open or endoscopic procedure) and to permit the treating physician to manipulate the electrode assembly from a proximal end of the shaft. The probe shaft can be flexible, curved, or steerable so as to allow the treating physician to move the active electrode into close proximity of the region of the disc, e.g., herniation, to be treated. The electrode assembly includes one or more active electrode(s) and a return electrode spaced from the active electrode(s) either on the instrument shaft or separate from the instrument shaft.

The active electrode(s) may comprise a single active electrode, or an electrode array, extending from an electrically insulating support member, typically made of an inorganic material such as ceramic, silicone or glass. The active electrode will usually have a smaller exposed surface area than the return electrode, such that the current densities are much higher at the active electrode than at the return electrode. Preferably, the return electrode has a relatively large, smooth surface extending around the instrument shaft to reduce current densities, thereby minimizing damage to adjacent tissue.

In another aspect, the present invention provides a method of treating an intervertebral disc, the method comprising contacting at least a first region of the intervertebral disc with at least one active electrode of an electrosurgical system. The at least one active electrode may be disposed on the distal end portion of a shaft of the electrosurgical system. A first high frequency voltage is applied between the active electrode(s) and one or more return electrode(s) such that at least a portion of the nucleus pulposus is ablated, and the volume of the disc's nucleus pulposus is decreased. After ablation of disc tissue at the first region of the intervertebral disc, other regions of the disc may be contacted with the at least one active electrode for ablation of disc tissue at the other regions of the disc. In one embodiment of the invention, axial translation of the at least one active electrode within the disc while applying the first high frequency voltage, leads to formation of a channel within the treated disc. The diameter of such a channel may be increased by rotating the at least one active electrode about the longitudinal axis of the shaft while applying the first high frequency voltage. Optionally, after a channel has been formed in the disc, disc tissue in the vicinity of the channel may be coagulated, or made necrotic, by applying a second high frequency voltage, wherein the second high frequency voltage may have different parameters as compared with the first high frequency voltage.

In another aspect, the present invention provides a method for treating an intervertebral disc, wherein the method involves providing an electrosurgical system including a probe having a shaft and a handle, the shaft having at least one active electrode located on the distal end portion of the shaft, and wherein the shaft distal end portion includes a pre-defined bias. The method further involves inserting the shaft distal end portion within the disc, and ablating at least a portion of the nucleus pulposus tissue from the disc such that the volume of the disc is decreased with minimal collateral damage to non-target tissue within the disc. The ablating step involves applying a high frequency voltage between the at least one active electrode and at least one return electrode. The high frequency voltage is sufficient to vaporize an electrically conductive fluid (e.g., a gel, isotonic saline, and/or tissue fluid) located between the at least one active electrode and the target tissue. Within the vaporized fluid a plasma is formed, and charged particles (e.g., electrons) are accelerated towards the nucleus pulposus to cause the molecular dissociation of nucleus pulposus tissue at the site to be ablated. This molecular dissociation is accompanied by the volumetric removal of disc tissue at the target site.

In one embodiment, inserting the shaft distal end portion in the disc involves advancing the shaft distal end portion via an introducer needle, the introducer needle having a lumen and a needle distal end, such that when the shaft distal end portion is advanced distally beyond the needle distal end, the at least one active electrode does not make contact with the needle distal end. One or more stages in the treatment or procedure may be performed under fluoroscopy to allow visualization of the shaft within the disc to be treated. Visualization of the shaft may be enhanced by inclusion of a radiopaque tracking device on the distal end of the shaft. The depth of penetration of the shaft into a disc can be monitored by one or more depth markings on the shaft.

In another aspect of the invention, the method further comprises retracting the shaft distal end portion proximally within the lumen of the introducer needle, wherein the at least one active electrode does not make contact with the needle distal end.

In another aspect of the invention, the shaft of the electrosurgical system includes a shield, and a distal insulating collar. In yet another aspect of the invention, the at least one active electrode includes an apical spike and a cusp. Applicants have found that an active electrode having an apical spike and a cusp promotes high current density in the vicinity of the active electrode.

For a further understanding of the nature and advantages of the invention, reference should be made to the following description taken in conjunction with the accompanying drawings.

BRIEF DESCRIPTION OF THE DRAWINGS

FIGS. 14A–14C illustrate an alternative embodiment incorporating a screen electrode;

FIG. 27C is a side view of the distal end portion of the curved shaft of FIG. 27B in the absence of the introducer device;

DESCRIPTION OF SPECIFIC EMBODIMENTS

Figure 1:
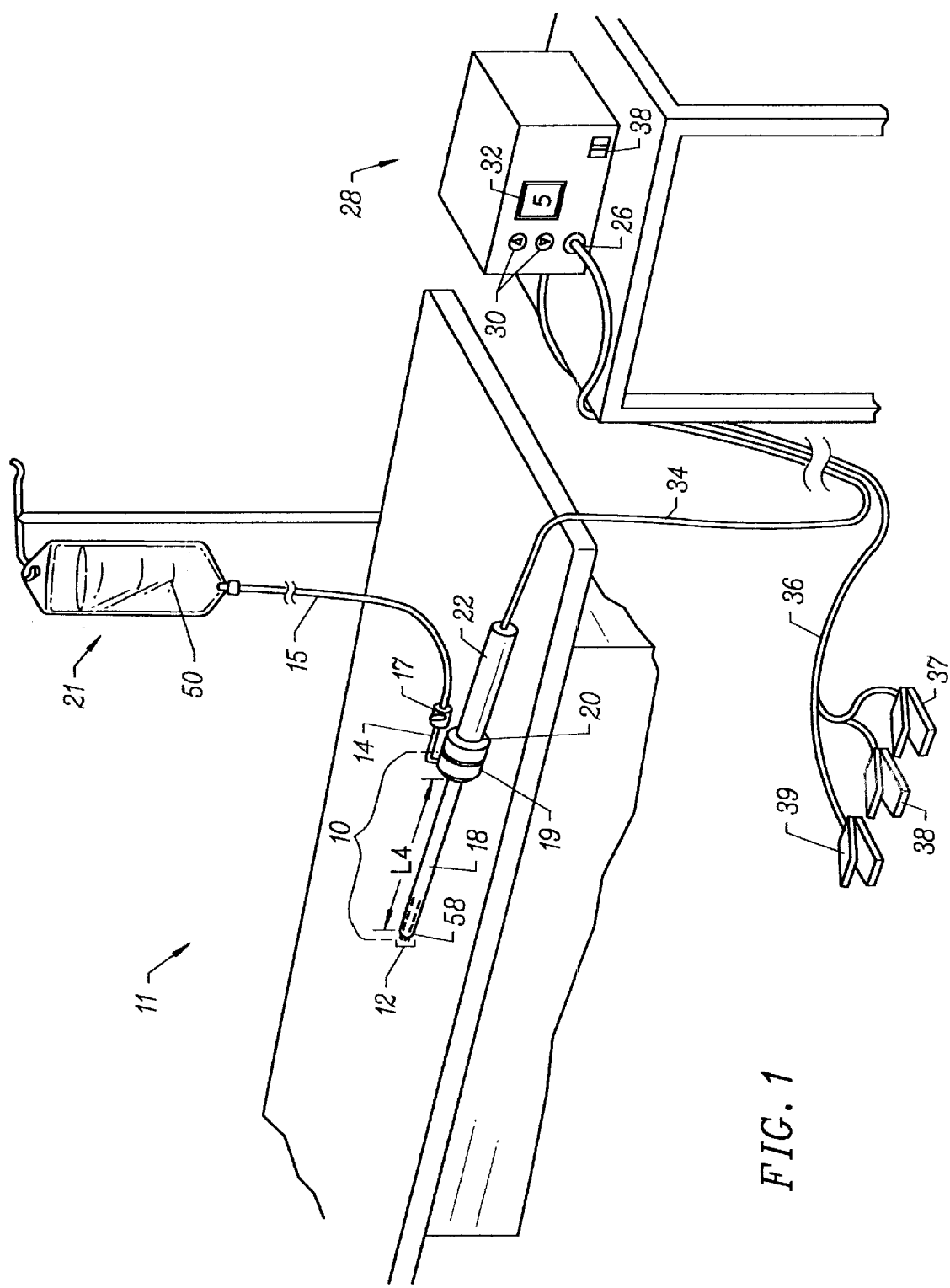
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including support tissue or other body structures in the spine. These procedures include treating interspinous tissue, degenerative discs, laminectomy/discectomy procedures for treating herniated discs, decompressive laminectomy for stenosis in the lumbosacral and cervical spine, localized tears or fissures in the annulus, nucleotomy, disc fusion procedures, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar discectomies. These procedures may be performed through open procedures, or using minimally invasive techniques, such as thoracoscopy, arthroscopy, laparascopy or the like.

The present invention involves techniques for treating disc abnormalities with RF energy. In some embodiments, RF energy is used to ablate, debulk and/or stiffen the tissue structure of the disc to reduce the volume of the disc, thereby relieving neck and back pain. In one aspect of the invention, spinal disc tissue is volumetrically removed or ablated to form holes, channels, divots or other spaces within the disc. In this procedure, a high frequency voltage difference is applied between one or more active electrode(s) and one or more return electrode(s) to develop high electric field intensities in the vicinity of the target tissue. The high electric field intensities adjacent the active electrode(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization.

The present invention also involves a system and method for treating the interspinous tissue (e.g., tendons, cartilage, synovial tissue in between the vertebrae, and other support tissue within and surrounding the vertebral column). In some embodiments, RF energy is used to heat and shrink the interspinous tissue to stabilize the vertebral column and reduce pain in the back and neck. In one aspect of the invention, an active electrode is positioned adjacent the interspinous tissue and the interspinous tissue is heated, preferably with RF energy, to a sufficient temperature to shrink the interspinous tissue. In a specific embodiment, a high frequency voltage difference is applied between one or more active electrode(s) and one or more return electrode(s) to develop high electric field intensities in the vicinity of the target tissue to controllably heat the target tissue.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site. Since the vapor layer or vaporized region has a relatively high electrical impedance, it minimizes the current flow into the electrically conductive fluid. This ionization, under the conditions described herein, induces the discharge of energetic electrons and photons from the vapor layer and to the surface of the target tissue A more detailed description of this phenomena, termed Coblation® can be found in commonly assigned U.S. Pat. No. 5,697,882 the complete disclosure of which is incorporated herein by reference.

Applicant believes that the principle mechanism of tissue removal in the Coblation® mechanism of the present invention is energetic electrons or ions that have been energized in a plasma adjacent to the active electrode(s). When a liquid is heated enough that atoms vaporize off the surface faster than they recondense, a gas is formed. When the gas is heated enough that the atoms collide with each other and knock their electrons off in the process, an ionized gas or plasma is formed (the so-called "fourth state of matter"). A more complete description of plasma can be found in Plasma Physics, by R. J. Goldston and P. H. Rutherford of the Plasma Physics Laboratory of Princeton University (1995), the complete disclosure of which is incorporated herein by reference. When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a gas and ionizing the gas by driving an electric current through it, or by shining radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In some embodiments, the present invention applies high frequency (RF) electrical energy in an electrically conducting media environment to shrink or remove (i.e., resect, cut, or ablate) a tissue structure and to seal transected vessels within the region of the target tissue. The present invention may also be useful for sealing larger arterial vessels, e.g., on the order of about 1 mm in diameter. In some embodiments, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue. In other embodiments, an electrosurgical instrument is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or shrink with the active electrode(s). In other embodiments, the power supply is combined with the coagulation instrument such that the coagulation electrode is used when the power supply is in the coagulation mode (low voltage), and the active electrode(s) are used when the power supply is in the ablation mode (higher voltage).

In one method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the active electrodes may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

In another aspect, the present invention may be used to shrink or contract collagen connective tissue which support the vertebral column or connective tissue within the disc. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphological Acad. Sci. of Hungary, Vol. 15(2), pp. 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980), the complete disclosure of which is incorporated by reference. Consequently, the controlled heating of tissue to a precise depth is critical to the achievement of therapeutic collagen shrinkage. A more detailed description of collagen shrinkage can be found in U.S. patent application Ser. No. 08/942,580 filed on Oct. 2, 1997, the complete disclosure of which is incorporated by reference.

The preferred depth of heating to effect the shrinkage of collagen in the heated region (i.e., the depth to which the tissue is elevated to temperatures between 60° C. to 70° C.) generally depends on (1) the thickness of the target tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 1.0 mm to 5.0 mm. In some embodiments of the present invention, the tissue is purposely damaged in a thermal heating mode to create necrosed or scarred tissue at the tissue surface. The high frequency voltage in the thermal heating mode is below the threshold of ablation as described above, but sufficient to cause some thermal damage to the tissue immediately surrounding the electrodes without vaporizing or otherwise debulking this tissue in situ. Typically, it is desired to achieve a tissue temperature in the range of about 60° C. to 100° C. to a depth of about 0.2 mm to 5 mm, usually about 1 mm to 2 mm. The voltage required for this thermal damage will partly depend on the electrode configurations, the conductivity of the area immediately surrounding the electrodes, the time period in which the voltage is applied and the depth of tissue damage desired. With the electrode configurations described in this application (e.g., FIGS. 15A–15D), the voltage level for thermal heating will usually be in the range of about 20 volts rms to 300 volts rms, preferably about 60 volts rms to 200 volts rms. The peak-to-peak voltages for thermal heating with a square wave form having a crest factor of about 2 are typically in the range of about 40 volts peak-to-peak to 600 volts peak-to-peak, preferably about 120 volts peak-to-peak to 400 volts peak-to-peak. In some embodiments, capacitors or other electrical elements may be used to increase the crest factor up to 10. The higher the voltage is within this range, the less time required. If the voltage is too high, however, the surface tissue may be vaporized, debulked or ablated, which is generally undesirable.

In yet another embodiment, the present invention may be used for treating degenerative discs with fissures or tears. In these embodiments, the active and return electrode(s) are positioned in or around the inner wall of the disc annulus such that the active electrode is adjacent to the fissure. High frequency voltage is applied between the active and return electrodes to heat the fissure and shrink the collagen fibers and create a seal or weld within the inner wall, thereby helping to close the fissure in the annulus. In these embodiments, the return electrode will typically be positioned proximally from the active electrode(s) on the instrument shaft, and an electrically conductive fluid will be applied to the target site to create the necessary current path between the active and return electrodes. In alternative embodiments, the disc tissue may complete this electrically conductive path.

The present invention is also useful for removing or ablating tissue around nerves, such as spinal, peripheral or cranial nerves. One of the significant drawbacks with the prior art shavers or microdebriders, conventional electrosurgical devices and lasers is that these devices do not differentiate between the target tissue and the surrounding nerves or bone. Therefore, the surgeon must be extremely careful during these procedures to avoid damage to the bone or nerves within and around the target site. In the present invention, the Coblation® process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more active electrode(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode(s) either individually or to the complete array of electrodes, if and when the tissue encountered at the tip or working end of the probe is normal tissue based on the measured electrical properties.

In one embodiment, the current limiting elements (discussed in detail above) are configured such that the active electrodes will shut down or turn off when the electrical impedance reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to tissue, will continue to conduct electric current to the return electrode. This selective ablation or removal of lower impedance tissue in combination with the Coblation® mechanism of the present invention allows the surgeon to precisely remove tissue around nerves or bone. Applicant has found that the present invention is capable of volumetrically removing tissue closely adjacent to nerves without impairment the function of the nerves, and without significantly damaging the tissue of the epineurium. One of the significant drawbacks with the prior art microdebriders, conventional electrosurgical devices and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation® process for removing tissue results in extremely small depths of collateral tissue damage as discussed above. This allows the surgeon to remove tissue close to a nerve without causing collateral damage to the nerve fibers.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the active electrode(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 eV to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 eV to 5 eV to break (typically on the order of about 8 eV). Accordingly, the present invention in its current configuration generally does not ablate or remove such fatty tissue. However, the present invention may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032, 375, filed Feb. 27, 1998, the complete disclosure of which is incorporated herein by reference.

In yet other embodiments, the present invention provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the active electrode(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's brain or to the surgical staff. The high frequency voltage is preferably selected to effect controlled removal of these tissue cells while minimizing substantial tissue necrosis to surrounding or underlying tissue. A more complete description of this phenomena can be found in co-pending U.S. patent application Ser. No. 09/109,219, filed Jun. 30, 1998, the complete disclosure of which is incorporated herein by reference.

The electrosurgical probe or catheter of the present invention can comprise a shaft or a handpiece having a proximal end and a distal end which supports one or more active electrode(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For endoscopic procedures within the spine, the shaft will have a suitable diameter and length to allow the surgeon to reach the target site (e.g., a disc or vertebra) by delivering the shaft through the thoracic cavity, the abdomen or the like. Thus, the shaft will usually have a length in the range of about 5.0 cm to 30.0 cm, and a diameter in the range of about 0.2 mm to about 20 mm. Alternatively, the shaft may be delivered directly through the patient's back in a posterior approach, which would considerably reduce the required length of the shaft. In any of these embodiments, the shaft may also be introduced through rigid or flexible endoscopes. Alternatively, the shaft may be a flexible catheter that is introduced through a percutaneous penetration in the patient. Specific shaft designs will be described in detail in connection with the figures hereinafter.

In an alternative embodiment, the probe may comprise a long, thin needle (e.g., on the order of about 1 mm in diameter or less) that can be percutaneously introduced through the patient's back directly into the spine. The needle will include one or more active electrode(s) for applying electrical energy to tissues within the spine. The needle may include one or more return electrode(s), or the return electrode may be positioned on the patient's back, as a dispersive pad. In either embodiment, sufficient electrical energy is applied through the needle to the active electrode(s) to either shrink the collagen fibers within the spinal disc, to ablate tissue within the disc, or to shrink support fibers surrounding the vertebrae.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The active electrode(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in and around the spinal cord, however, makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) will include the appropriate electrical connections for coupling the return electrode(s) and the active electrode(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a pH less than 7.0 or by using a high velocity stream of abrasive particles (e.g., grit blasting) to create asperities on the surface of an elongated electrode. A more detailed description of such electrode configurations can be found in U.S. Pat. No. 5,843,019, the complete disclosure of which is incorporated herein by reference.

The return electrode is typically spaced proximally from the active electrode(s) a suitable distance to avoid electrical shorting between the active and return electrodes in the presence of electrically conductive fluid. In most of the embodiments described herein, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

The current flow path between the active electrodes and the return electrode(s) may be generated by submerging the tissue site in an electrical conducting fluid (e.g., within a viscous fluid, such as an electrically conductive gel) or by directing an electrically conductive fluid along a fluid path to the target site (i.e., a liquid, such as isotonic saline, hypotonic saline or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conductive fluid between the active and return electrodes is described in U.S. Pat. No. 5,697,281, previously incorporated herein by reference. Alternatively, the body's natural conductive fluids, such as blood or extracellular saline, may be sufficient to establish a conductive path between the return electrode(s) and the active electrode(s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply, or generator, may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, the gaseous products of ablation, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, co-pending U.S. patent application Ser. No. 09/010,382 filed Jan. 21, 1998, the complete disclosure of which is incorporated herein by reference.

As an alternative or in addition to suction, it may be desirable to contain the excess electrically conductive fluid, tissue fragments and/or gaseous products of ablation at or near the target site with a containment apparatus, such as a basket, retractable sheath, or the like. This embodiment has the advantage of ensuring that the conductive fluid, tissue fragments or ablation products do not flow through the patient's vasculature or into other portions of the body. In addition, it may be desirable to limit the amount of suction to limit the undesirable effect suction may have on hemostasis of severed blood vessels.

The present invention may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within said instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The tip region of the instrument may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip which also serves as a conduit for the supply of the electrically conductive fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals effects shrinking, cutting, removing, ablating, shaping, contracting or otherwise modifying the target tissue. In some embodiments of the present invention, the tissue volume over which energy is dissipated (i.e., a high current density exists) may be more precisely controlled, for example, by the use of a multiplicity of small active electrodes whose effective diameters or principal dimensions range from about 10 mm to 0.01 mm, preferably from about 2 mm to 0.05 mm, and more preferably from about 1 mm to 0.1 mm. In this embodiment, electrode areas for both circular and non-circular terminals will have a contact area (per active electrode) below 50 $mm^2$ for electrode arrays and as large as 75 $mm^2$ for single electrode embodiments. In multiple electrode array embodiments, the contact area of each active electrode is typically in the range from 0.0001 $mm^2$ to 1 $mm^2$, and more preferably from 0.001 $mm^2$ to 0.5 $mm^2$. The circumscribed area of the electrode array or active electrode is in the range from 0.25 $mm^2$ to 75 $mm^2$, preferably from 0.5 $mm^2$ to 40 $mm^2$. In multiple electrode embodiments, the array will usually include at least two isolated active electrodes, often at least five active electrodes, often greater than 10 active electrodes and even 50 or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or active electrode(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

It should be clearly understood that the invention is not limited to electrically isolated active electrodes, or even to a plurality of active electrodes. For example, the array of active electrodes may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

In other embodiments, the active electrodes are spaced from the tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the tissue bonds are dissociated or broken as in previous embodiments, while minimizing the electron flow, and thus the thermal energy, in contact with the tissue.

The electrically conductive fluid should have a threshold conductivity to provide a suitable conductive path between the return electrode and the active electrode(s). The electrical conductivity of the fluid (in units of millisiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Applicant has found that a more conductive fluid, or one with a higher ionic concentration, will usually provide a more aggressive ablation rate. For example, a saline solution with higher levels of sodium chloride than conventional saline (which is on the order of about 0.9% sodium chloride) e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals near the left end of the periodic chart. In addition, other electronegative elements may be used in place of chlorine, such as fluorine.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400–600 kHz) to minimize low frequency current flow into the heart or the nerves of the head and neck. The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation). Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in co-pending patent applications Ser. Nos. 09/058,571 and 09/058,336, filed Apr. 10, 1998, the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Referring to FIG. 1, an exemplary electrosurgical system 11 for treatment of tissue in the spine will now be described in detail. Electrosurgical system 11 generally comprises an electrosurgical handpiece or probe 10 connected to a power supply 28 for providing high frequency voltage to a target site, and a fluid source 21 for supplying electrically conductive fluid 50 to probe 10. In addition, electrosurgical system 11 may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 211 (see FIG. 4) in the probe 10 for aspirating the target site.

As shown, probe 10 generally includes a proximal handle 19 and an elongate shaft 18 having an array 12 of active electrodes 58 at its distal end. A connecting cable 34 has a connector 26 for electrically coupling the active electrodes 58 to power supply 28. The active electrodes 58 are electrically isolated from each other and each of electrodes 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site. Fluid supply tube 15 may be connected to a suitable pump (not shown), if desired.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to active electrodes 58. In an exemplary embodiment, first foot pedal 37 is used to place the power supply into the "ablation" mode and second foot pedal 38 places power supply 28 into the "sub-ablation" mode (e.g., for coagulation or contraction of tissue). The third foot pedal 39 allows the user to adjust the voltage level within the "ablation" mode. In the ablation mode, a sufficient voltage is applied to the active electrodes to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the active electrodes to avoid vaporization of the electrically conductive fluid and subsequent molecular dissociation of the tissue. The surgeon may automatically toggle the power supply between the ablation and sub-ablation modes by alternately stepping on foot pedals 37, 38, respectively. In some embodiments, this allows the surgeon to quickly move between coagulation/thermal heating and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 2:
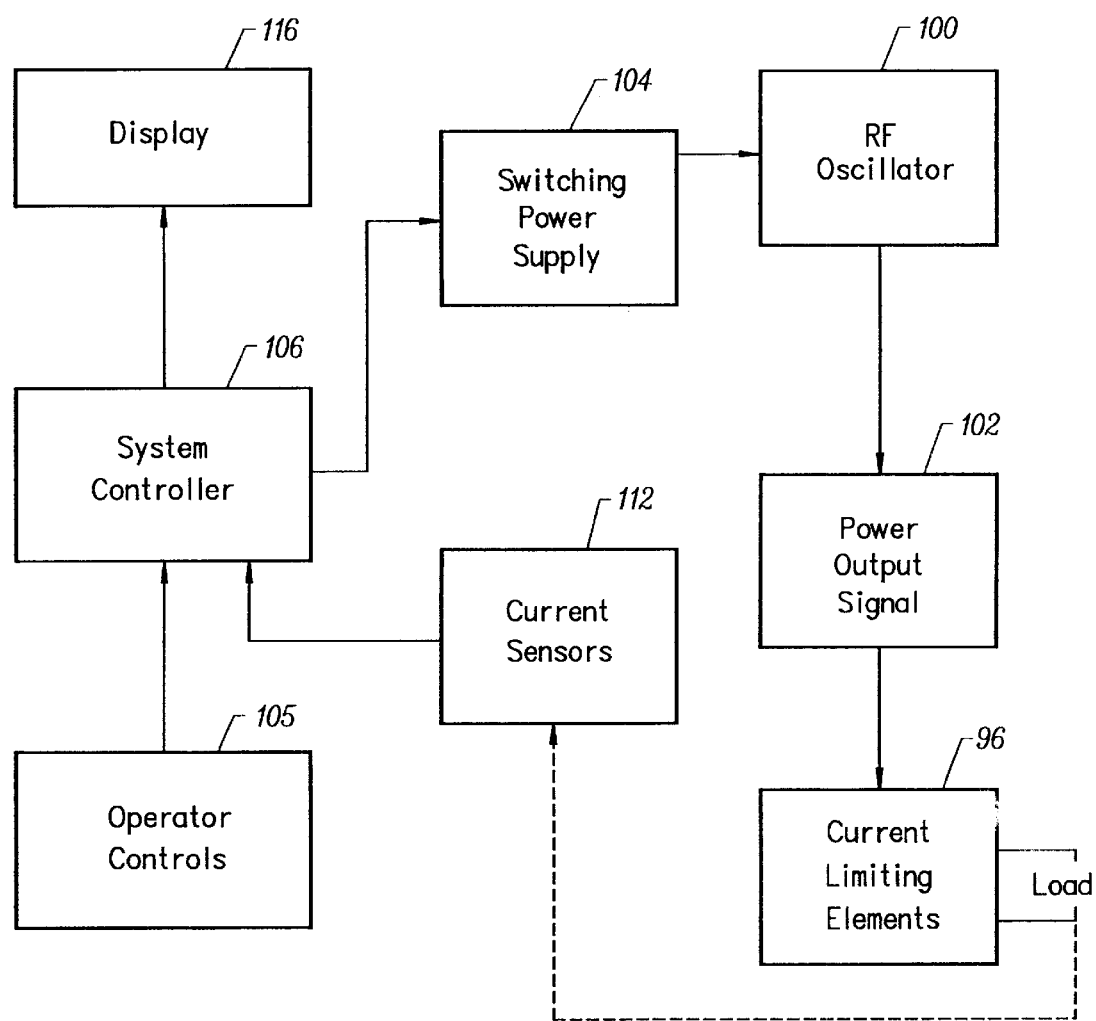
FIG. 2 schematically illustrates one embodiment of a power supply according to the present invention.
Figure 3:
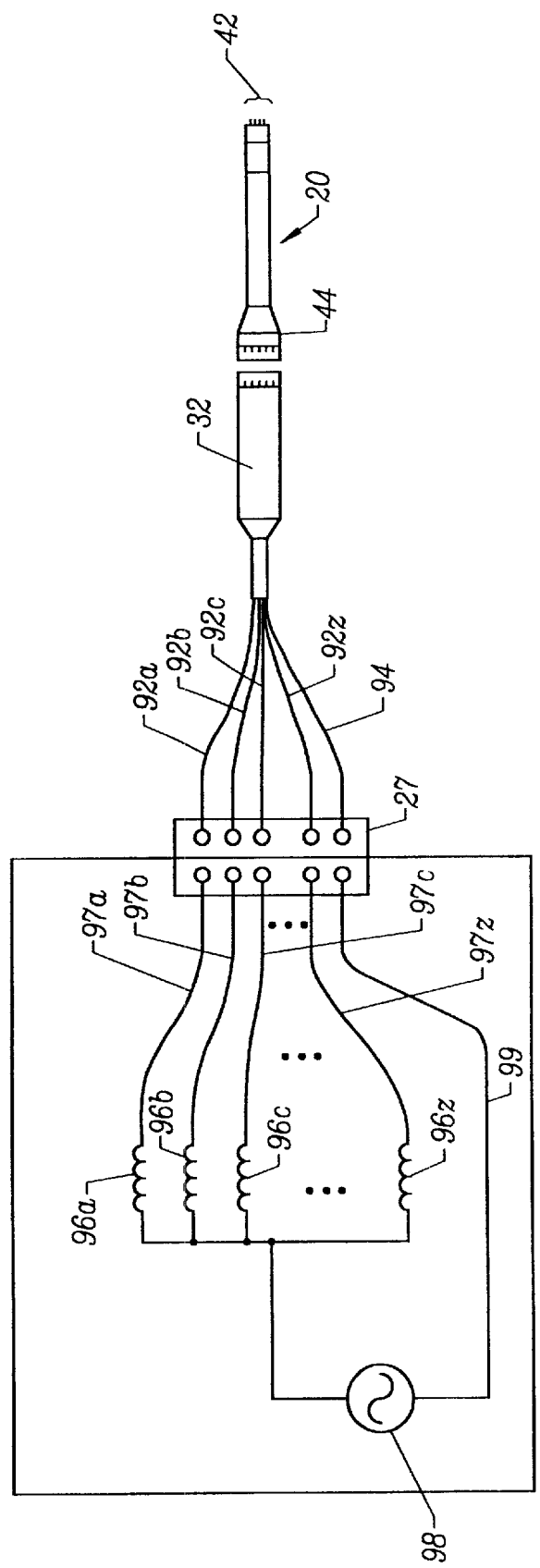
FIG. 3 illustrates an electrosurgical system incorporating a plurality of active electrodes and associated current limiting elements.

Referring now to FIGS. 2 and 3, a representative high frequency power supply for use according to the principles of the present invention will now be described. The high frequency power supply of the present invention is configured to apply a high frequency voltage of about 10 volts RMS to 500 volts RMS between one or more active electrodes (and/or coagulation electrode) and one or more return electrodes. In the exemplary embodiment, the power supply applies about 70 volts RMS to 350 volts RMS in the ablation mode and about 20 volts to 90 volts in a subablation mode, preferably 45 volts to 70 volts in the subablation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being treated, and/or the maximum allowed temperature selected for the probe tip. The power supply allows the user to select the voltage level according to the specific requirements of a particular procedure, e.g., spinal surgery, arthroscopic surgery, dermatological procedure, ophthalmic procedures, open surgery, or other endoscopic surgery procedure.

As shown in FIG. 2, the power supply generally comprises a radio frequency (RF) power oscillator 70 having output connections for coupling via a power output signal 71 to the load impedance, which is represented by the electrode assembly when the electrosurgical probe is in use. In the representative embodiment, the RF oscillator operates at about 100 kHz. The RF oscillator is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 71 is designed to incur minimal voltage decrease (i.e., sag) under load. This improves the applied voltage to the active electrodes and the return electrode, which improves the rate of volumetric removal (ablation) of tissue.

Power is supplied to RF oscillator 70 by a switching power supply 72 coupled between the power line and the RF oscillator rather than a conventional transformer. The switching power supply 72 allows power supply 28 to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 72 operates at about 100 kHz.

A controller 74 coupled to the operator controls 73 (i.e., foot pedals and voltage selector) and display 76, is connected to a control input of the switching power supply 72 for adjusting the generator output power by supply voltage variation. The controller 74 may be a microprocessor or an integrated circuit. The power supply may also include one or more current sensors 75 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield," thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the active electrodes 102 (see FIG. 4).

Alternatively, in one embodiment, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application Ser. No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from said active electrode into the low resistance medium (e.g., saline irrigant or conductive gel). Power output signal may also be coupled to a plurality of current limiting elements 96, which are preferably located on the daughter board since the current limiting elements may vary depending on the application. A more complete description of a representative power supply can be found in commonly assigned U.S. patent application Ser. No. 09/058,571, previously incorporated herein by reference.

Figure 4:
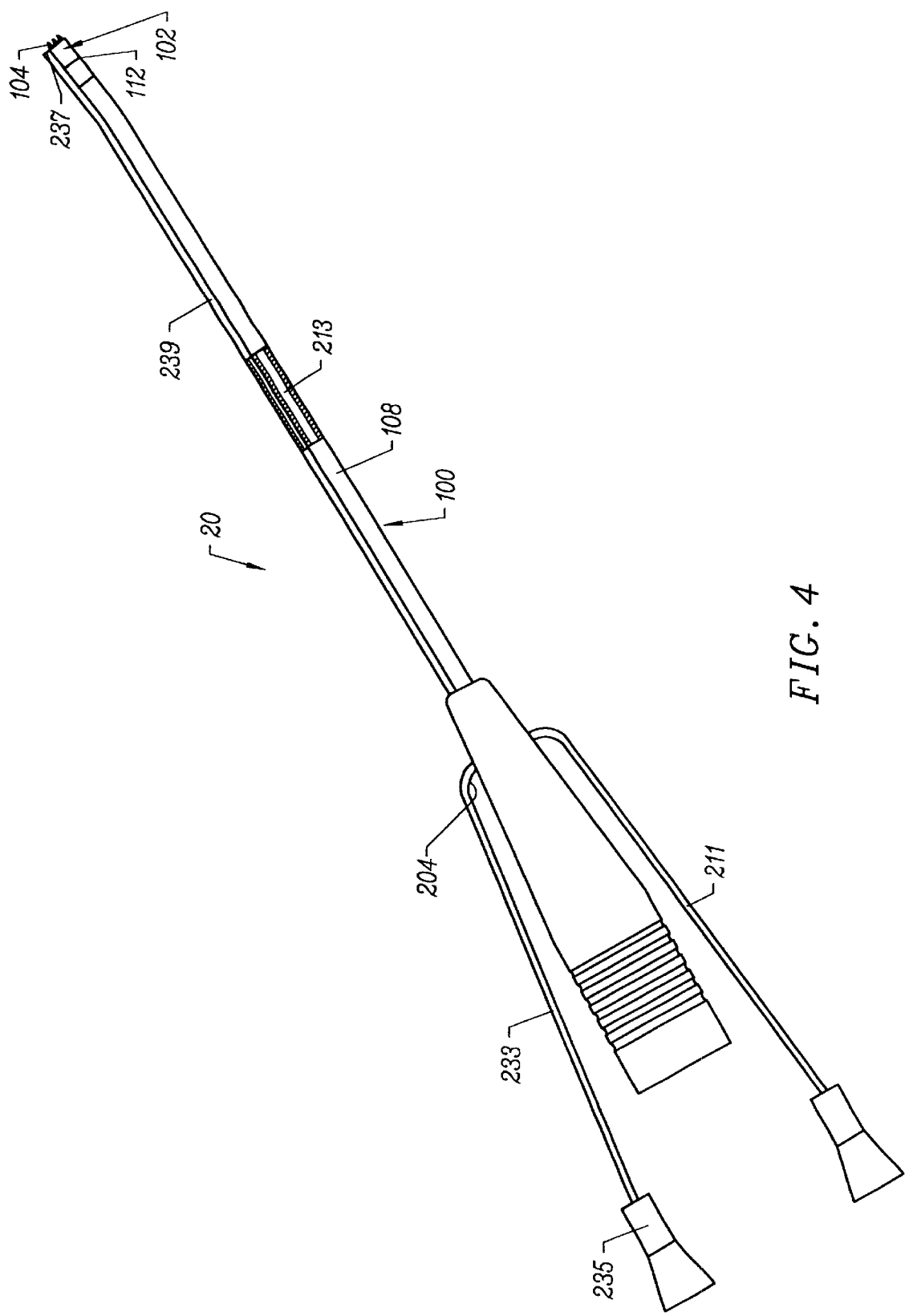
FIG. 4 is a side view of an electrosurgical probe according to the present invention.
Figure 5:
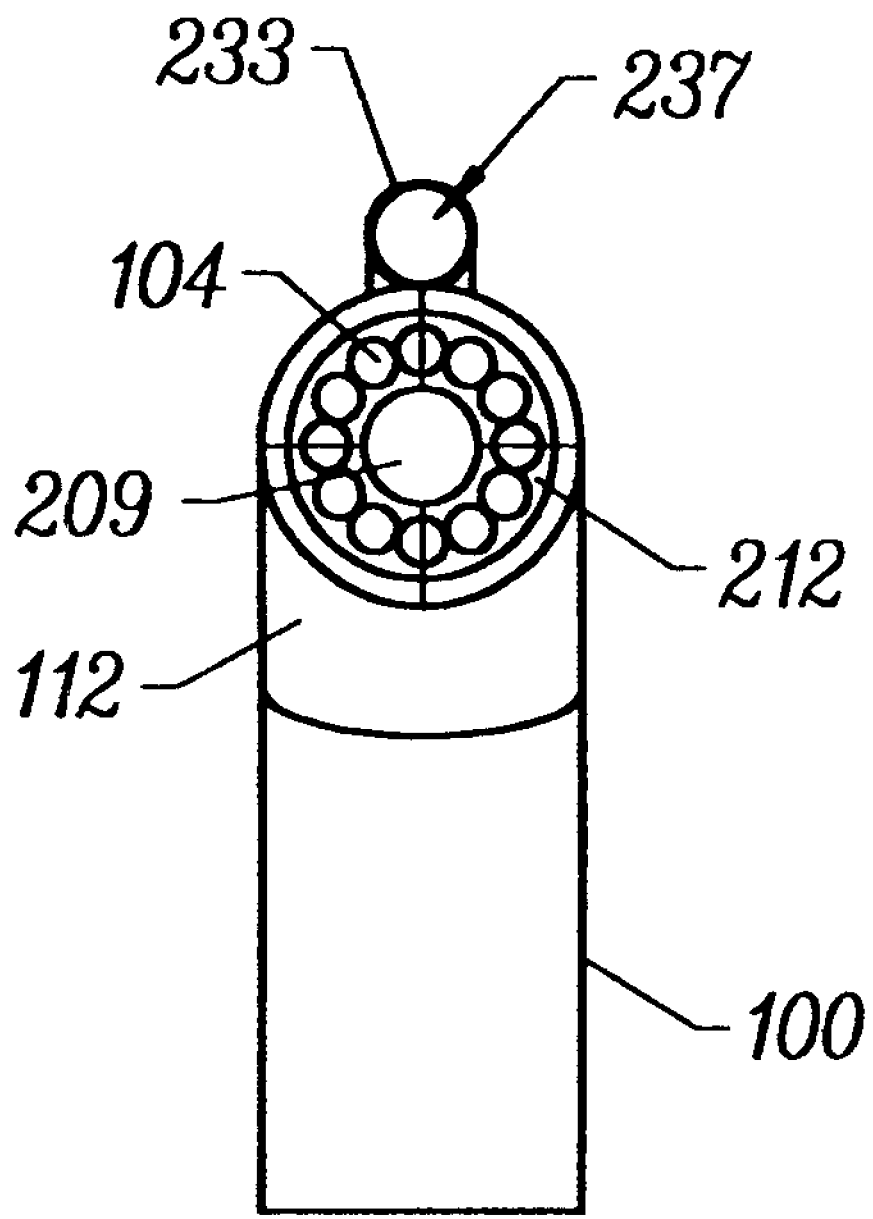
FIG. 5 is a view of the distal end portion of the probe of FIG. 4
Figure 6:
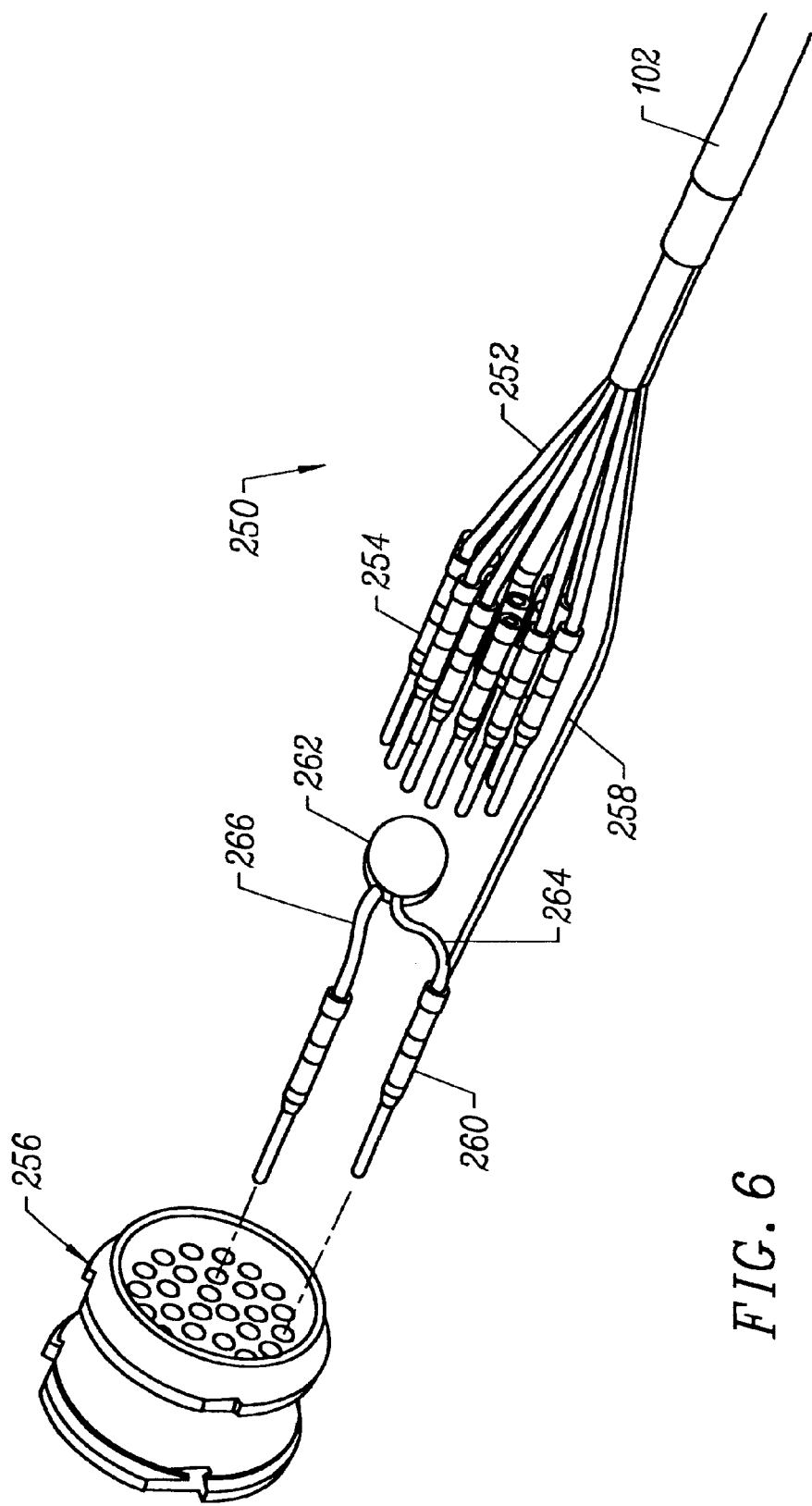
FIG. 6 is an exploded view of a proximal portion of an electrosurgical probe.

FIGS. 4–6 illustrate an exemplary electrosurgical probe 20 constructed according to the principles of the present invention. As shown in FIG. 4, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis. Alternatively, the return electrode may comprise an annular band coupled to an insulating shaft and having a connector extending within the shaft to its proximal end.

Handle 204 typically comprises a plastic material that is easily molded into a suitable shape for handling by the surgeon. Handle 204 defines an inner cavity (not shown) that houses the electrical connections 250 (FIG. 6), and provides a suitable interface for connection to an electrical connecting cable distal portion 22 (see FIG. 1) Electrode support member 102 extends from the distal end of shaft 100 (usually about 1 mm to 20 mm), and provides support for a plurality of electrically isolated active electrodes 104 (see FIG. 5). As shown in FIG. 4, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, tubing 239 is a tube that extends along the exterior of shaft 100 to a point just distal of return electrode 112 (see FIG. 5). In this embodiment, the fluid is directed through an opening 237 past return electrode 112 to the active electrodes 104. Probe 20 may also include a valve 17 (FIG. 1) or equivalent structure for controlling the flow rate of the electrically conductive fluid to the target site.

As shown in FIG. 4, the distal portion of shaft 100 is preferably bent to improve access to the operative site of the tissue being treated. Electrode support member 102 has a substantially planar tissue treatment surface 212 (FIG. 5) that is usually at an angle of about 10 degrees to 90 degrees relative to the longitudinal axis of shaft 100, preferably about 30 degrees to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in U.S. Pat. No. 5, 697,909, the complete disclosure of which has previously been incorporated herein by reference. Alternatively, the shaft 100 of the present invention may be bent by the physician to the appropriate angle using a conventional bending tool or the like.

In the embodiment shown in FIGS. 4 to 6, probe 20 includes a return electrode 112 for completing the current path between active electrodes 104 and a high frequency power supply 28 (see FIG. 1). As shown, return electrode 112 preferably comprises an exposed portion of shaft 100 shaped as an annular conductive band near the distal end of shaft 100 slightly proximal to tissue treatment surface 212 of electrode support member 102, typically about 0.5 mm to 10 mm and more preferably about 1 mm to 10 mm. Return electrode 112 or shaft 100 is coupled to a connector 258 that extends to the proximal end of probe 10/20, where it is suitably connected to power supply 28 (FIG. 1).

As shown in FIG. 4, return electrode 112 is not directly connected to active electrodes 104. To complete this current path so that active electrodes 104 are electrically connected to return electrode 112, an electrically conductive fluid (e.g., isotonic saline) is caused to flow therebetween. In the representative embodiment, the electrically conductive fluid is delivered through fluid tube 233 to opening 237, as described above. Alternatively, the conductive fluid may be delivered by a fluid delivery element (not shown) that is separate from probe 20. In arthroscopic surgery, for example, the target area of the joint will be flooded with isotonic saline and the probe 90 will be introduced into this flooded target area. Electrically conductive fluid can be continually resupplied to maintain the conduction path between return electrode 112 and active electrodes 104. In other embodiments, the distal portion of probe 20 may be dipped into a source of electrically conductive fluid, such as a gel or isotonic saline, prior to positioning at the target site. Applicant has found that the surface tension of the fluid and/or the viscous nature of a gel allows the conductive fluid to remain around the active and return electrodes for long enough to complete its function according to the present invention, as described below. Alternatively, the conductive fluid, such as a gel, may be applied directly to the target site.

Figure 8A:
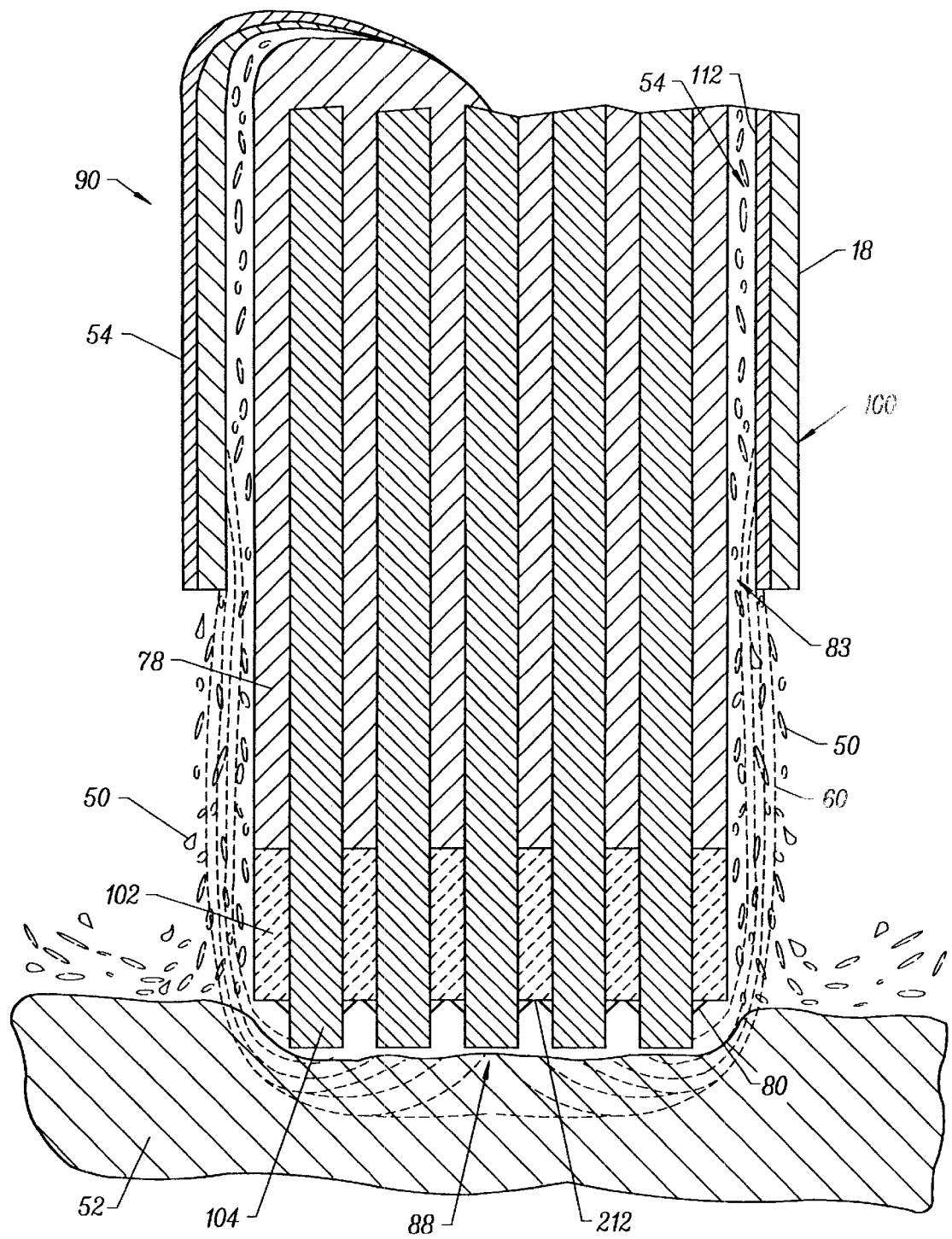
FIGS. 8A–8C are cross-sectional views of the distal portions of three different embodiments of an electrosurgical probe according to the present invention.
Figure 8B:
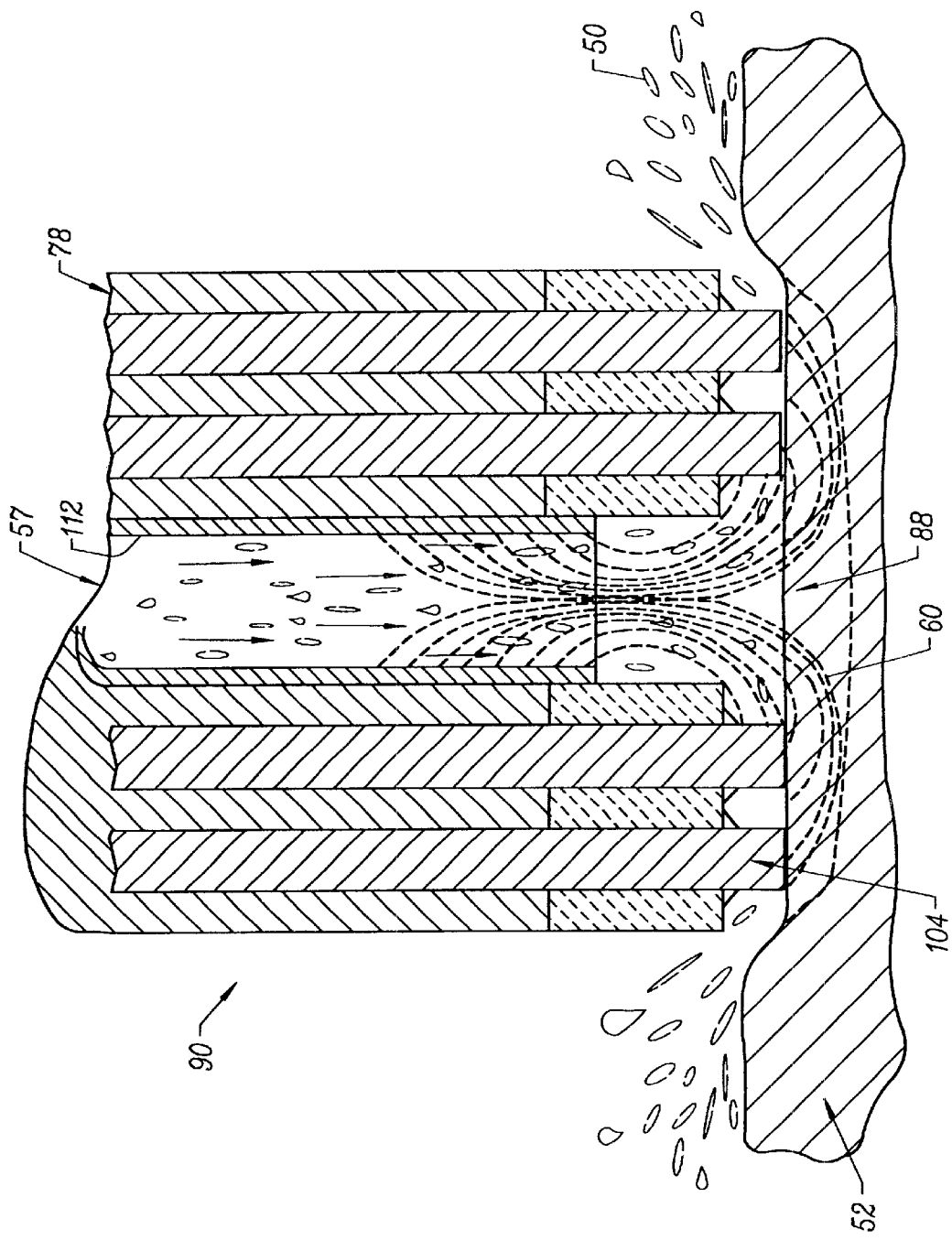

In alternative embodiments, the fluid path may be formed in probe 90 by, for example, an inner lumen or an annular gap between the return electrode and a tubular support member within shaft 100 (see FIGS. 8A and 8B). This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 90 via a fluid supply tube (not shown) that may or may not have a controllable valve. A more complete description of an electrosurgical probe incorporating one or more fluid lumen(s) can be found in U.S. Pat. No. 5,697,281, the complete disclosure of which has previously been incorporated herein by reference.

Referring to FIG. 5, the electrically isolated active electrodes 104 are spaced apart over tissue treatment surface 212 of electrode support member 102. The tissue treatment surface and individual active electrodes 104 will usually have dimensions within the ranges set forth above. In the representative embodiment, the tissue treatment surface 212 has a circular cross-sectional shape with a diameter in the range of 1 mm to 20 mm. The individual active electrodes 104 preferably extend outward from tissue treatment surface 212 by a distance of about 0.1 mm to 4 mm, usually about 0.2 mm to 2 mm. Applicant has found that this configuration increases the high electric field intensities and associated current densities around active electrodes 104 to facilitate the ablation and shrinkage of tissue as described in detail above.

In the embodiment of FIGS. 4 to 6, the probe includes a single, larger opening 209 in the center of tissue treatment surface 212, and a plurality of active electrodes (e.g., about 3–15) around the perimeter of surface 212 (see FIG. 5). Alternatively, the probe may include a single, annular, or partially annular, active electrode at the perimeter of the tissue treatment surface. The central opening 209 is coupled to a suction lumen (not shown) within shaft 100 and a suction tube 211 (FIG. 4) for aspirating tissue, fluids and/or gases from the target site. In this embodiment, the electrically conductive fluid generally flows radially inward past active electrodes 104 and then back through the opening 209. Aspirating the electrically conductive fluid during surgery allows the surgeon to see the target site, and it prevents the fluid from flowing into the patient's body.

Figure 7A:
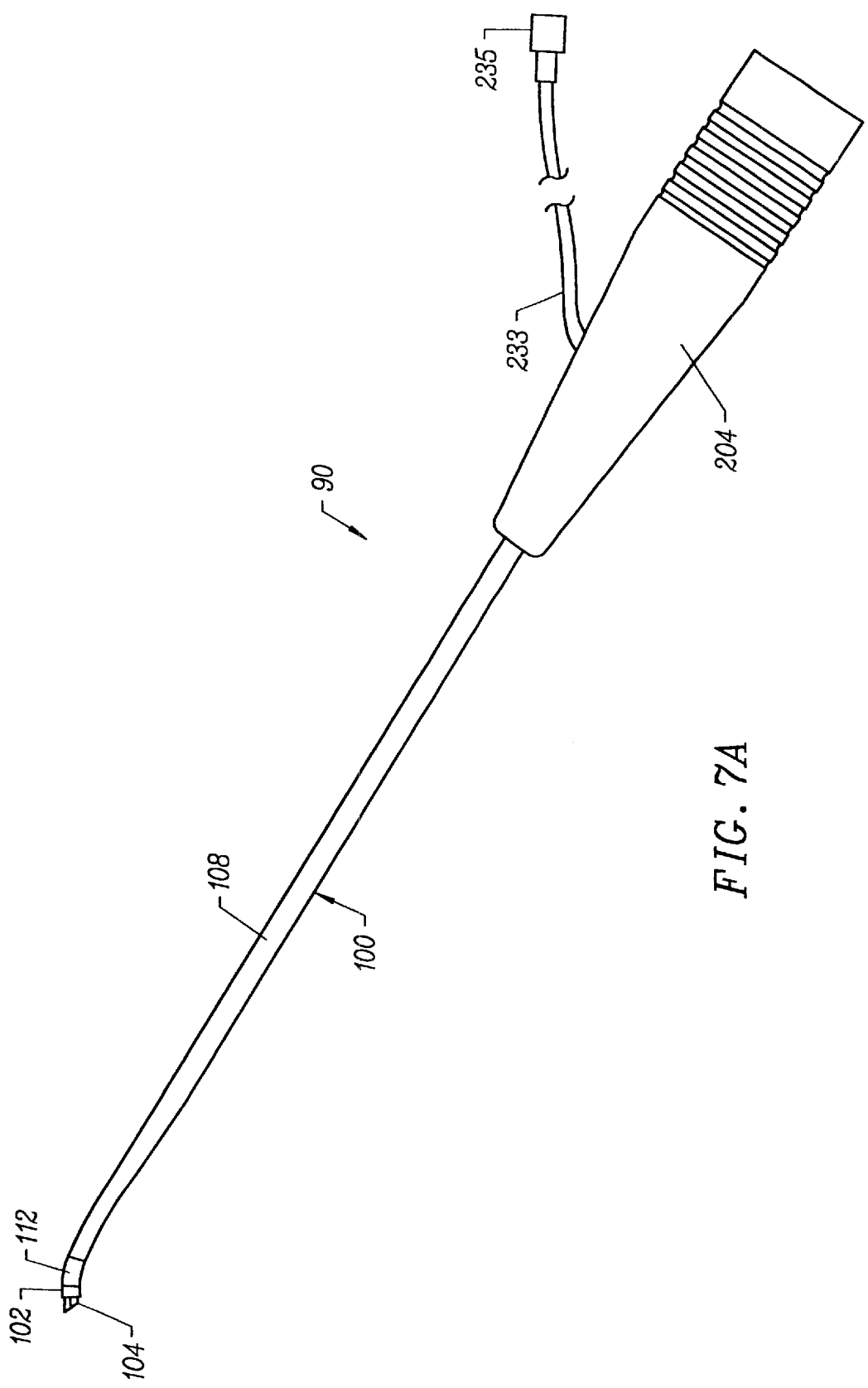
FIGS. 7A and 7B are perspective and end views, respectively, of an alternative electrosurgical probe incorporating an inner fluid lumen.
Figure 7B:
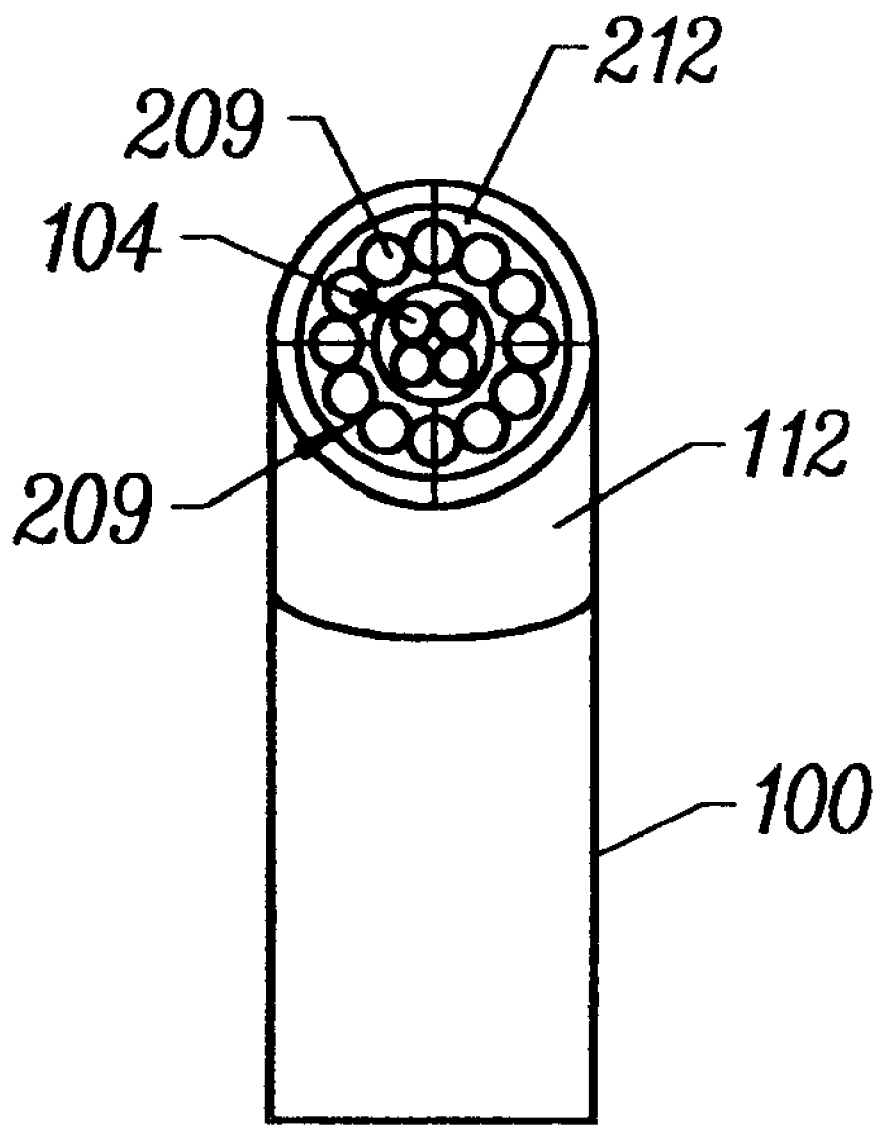

Of course, it will be recognized that the distal tip of an electrosurgical probe of the invention, e.g. probe 10/20/90, may have a variety of different configurations. For example, the probe may include a plurality of openings 209 around the outer perimeter of tissue treatment surface 212 (see FIG. 7B). In this embodiment, the active electrodes 104 extend distally from the center of tissue treatment surface 212 such that they are located radially inward from openings 209. The openings are suitably coupled to fluid tube 233 for delivering electrically conductive fluid to the target site, and suction tube 211 for aspirating the fluid after it has completed the conductive path between the return electrode 112 and the active electrodes 104.

FIG. 6 illustrates the electrical connections 250 within handle 204 for coupling active electrodes 104 and return electrode 112 to the power supply 28. As shown, a plurality of wires 252 extend through shaft 100 to couple active electrodes 104 to a plurality of pins 254, which are plugged into a connector block 256 for coupling to a connecting cable distal end 22 (FIG. 1). Similarly, return electrode 112 is coupled to connector block 256 via a wire 258 and a plug 260.

According to the present invention, the probe 20 further includes an identification element that is characteristic of the particular electrode assembly so that the same power supply 28 can be used for different electrosurgical operations. In one embodiment, for example, the probe (e.g., 20) includes a voltage reduction element or a voltage reduction circuit for reducing the voltage applied between the active electrodes 104 and the return electrode 112. The voltage reduction element serves to reduce the voltage applied by the power supply so that the voltage between the active electrodes and the return electrode is low enough to avoid excessive power dissipation into the electrically conducting medium and/or ablation of the soft tissue at the target site. In some embodiments, the voltage reduction element allows the power supply 28 to apply two different voltages simultaneously to two different electrodes (see FIG. 15D). In other embodiments, the voltage reduction element primarily allows the electrosurgical probe to be compatible with various electrosurgical generators supplied by ArthroCare Corporation (Sunnyvale, Calif.) that are adapted to apply higher voltages for ablation or vaporization of tissue. For thermal heating or coagulation of tissue, for example, the voltage reduction element will serve to reduce a voltage of about 100 volts rms to 170 volts rms (which is a setting of 1 or 2 on the ArthroCare Model 970 and 980 (i.e., 2000) Generators) to about 45 volts rms to 60 volts rms, which is a suitable voltage for coagulation of tissue without ablation (e.g., molecular dissociation) of the tissue.

Of course, for some procedures, the probe will typically not require a voltage reduction element. Alternatively, the probe may include a voltage increasing element or circuit, if desired. Alternatively or additionally, the cable 34 and/or cable distal end 22 that couples the power supply 28 to the probe may be used as a voltage reduction element. The cable has an inherent capacitance that can be used to reduce the power supply voltage if the cable is placed into the electrical circuit between the power supply, the active electrodes and the return electrode. In this embodiment, the cable distal end 22 may be used alone, or in combination with one of the voltage reduction elements discussed above, e.g., a capacitor. Further, it should be noted that the present invention can be used with a power supply that is adapted to apply a voltage within the selected range for treatment of tissue. In this embodiment, a voltage reduction element or circuitry may not be desired.

Figure 8C:
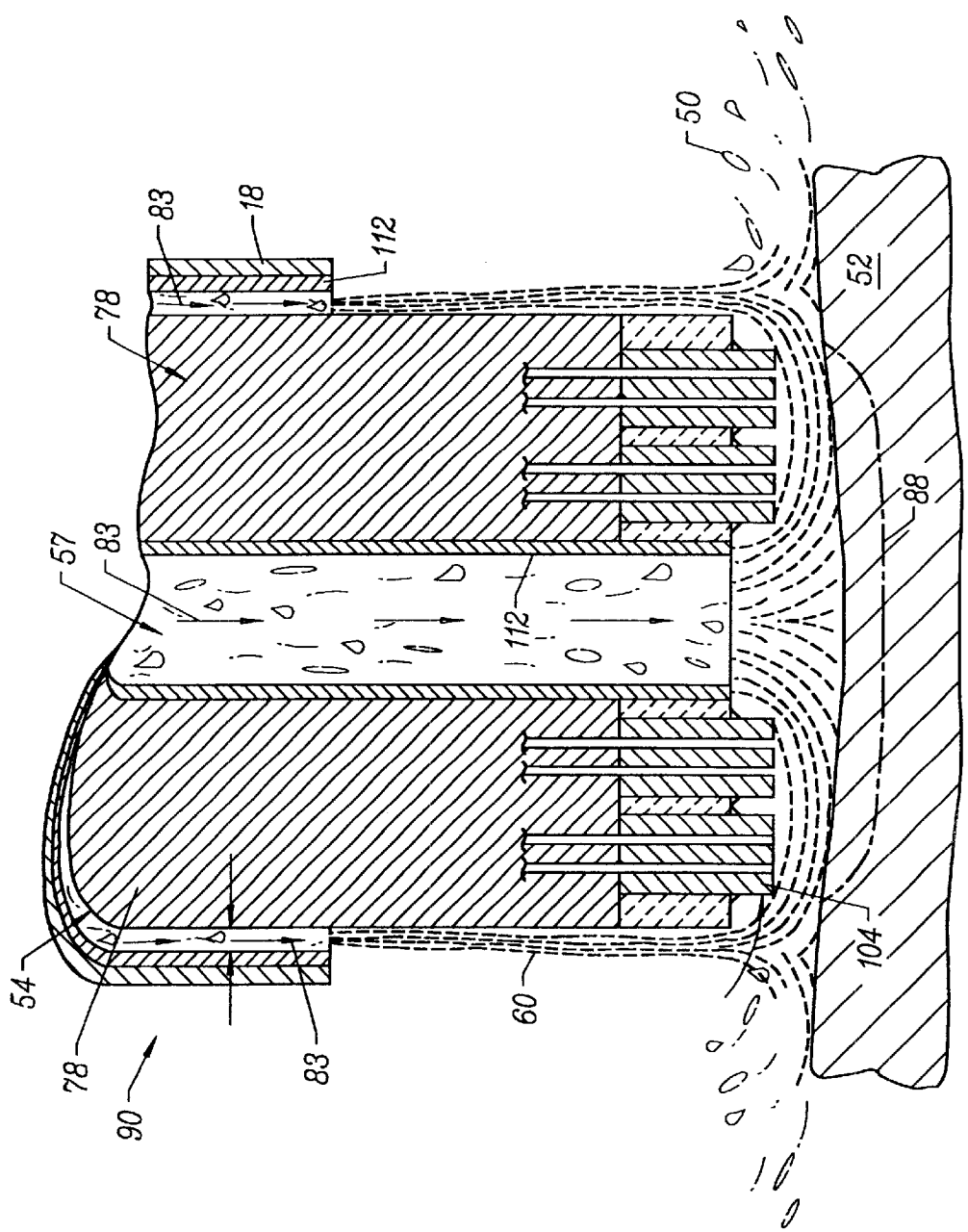

FIGS. 8A–8C schematically illustrate the distal portion of three different embodiments of probe 90 according to the present invention. As shown in FIG. 8A, active electrodes 104 are anchored in a support matrix 102' of suitable insulating material (e.g., silicone or a ceramic or glass material, such as alumina, zirconia and the like) which could be formed at the time of manufacture in a flat, hemispherical or other shape according to the requirements of a particular procedure. The preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support matrix 102' is adhesively joined to a tubular support member 78 that extends most or all of the distance between matrix 102' and the proximal end of probe 90. Tubular member 78 preferably comprises an electrically insulating material, such as an epoxy or silicone-based material.

In a preferred construction technique, active electrodes 104 extend through pre-formed openings in the support matrix 102' so that they protrude above tissue treatment surface 212 by the desired distance. The electrodes are then bonded to the tissue treatment surface 212 of support matrix 102', typically by an inorganic sealing material 80. Sealing material 80 is selected to provide effective electrical insulation, and good adhesion to both support matrix 102' and the platinum or titanium active electrodes. Sealing material 80 additionally should have a compatible thermal expansion coefficient and a melting point well below that of platinum or titanium and alumina or zirconia, typically being a glass or glass ceramic.

In the embodiment shown in FIG. 8A, return electrode 112 comprises an annular member positioned around the exterior of shaft 100 of probe 90. Return electrode 112 may fully or partially circumscribe tubular support member 78 to form an annular gap 54 therebetween for flow of electrically conducting liquid 50 therethrough, as discussed below. Gap 54 preferably has a width in the range of 0.25 mm to 4 mm. Alternatively, probe 90 may include a plurality of longitudinal ribs between support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 118, which is typically formed as one or more electrically insulative sheaths or coatings, such as polytetrafluoroethylene, polyimide, and the like. The provision of the electrically insulative jacket 118 over return electrode 112 prevents direct electrical contact between return electrode 112 and any adjacent body structure. Such direct electrical contact between a body structure (e.g., tendon) and an exposed return electrode 112 could result in unwanted heating and necrosis of the structure at the point of contact.

As shown in FIG. 8A, return electrode 112 is not directly connected to active electrodes 104. To complete this current path so that terminals 104 are electrically connected to return electrode 112, electrically conducting liquid 50 (e.g., isotonic saline) is caused to flow along fluid path(s) 83. Fluid path 83 is formed by annular gap 54 between return electrode 112 and tubular support member 78. The electrically conducting liquid 50 flowing through fluid path 83 provides a pathway for electrical current flow between active electrodes 104 and return electrode 112, as illustrated by the current flux lines 60 in FIG. 8A. When a voltage difference is applied between active electrodes 104 and return electrode 112, high electric field intensities will be generated at the distal tips of active electrodes 104 with current flow from active electrodes 104 through the target tissue to return electrode 112, the high electric field intensities causing ablation of tissue 52 in zone 88.

FIG. 8B illustrates another alternative embodiment of electrosurgical probe 90 which has a return electrode 112 positioned within tubular member 78. Return electrode 112 is preferably a tubular member defining an inner lumen 57 for allowing electrically conducting liquid 50 (e.g., isotonic saline) to flow therethrough in electrical contact with return electrode 112. In this embodiment, a voltage difference is applied between active electrodes 104 and return electrode 112 resulting in electrical current flow through the electrically conducting liquid 50 as shown by current flux lines 60. As a result of the applied voltage difference and concomitant high electric field intensities at the tips of active electrodes 104, tissue 52 becomes ablated or transected in zone 88.

FIG. 8C illustrates another embodiment of probe 90 that is a combination of the embodiments in FIGS. 8A and 8B. As shown, this probe includes both an inner lumen 57 and an outer gap or plurality of outer lumens 54 for flow of electrically conductive fluid. In this embodiment, the return electrode 112 may be positioned within tubular member 78 as in FIG. 8B, outside of tubular member 78 as in FIG. 8A, or in both locations.

Figure 9:
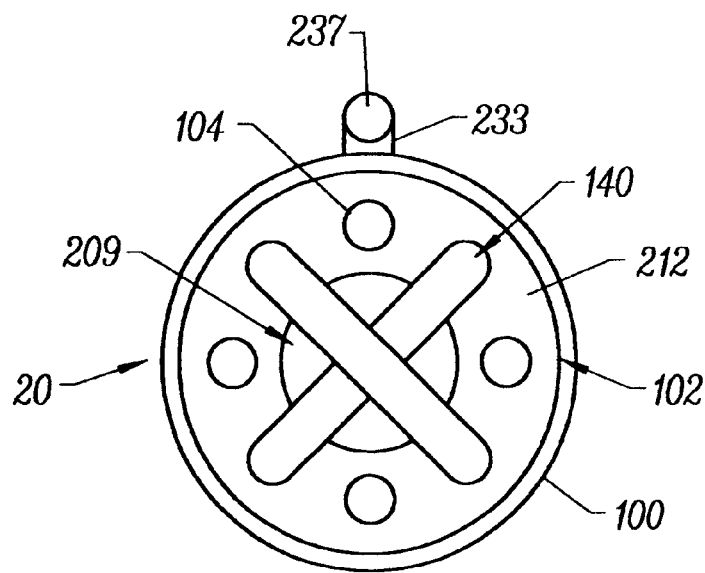
FIGS. 9–12 are end views of alternative embodiments of the probe of FIG. 4, incorporating aspiration electrode(s)
Figure 13:
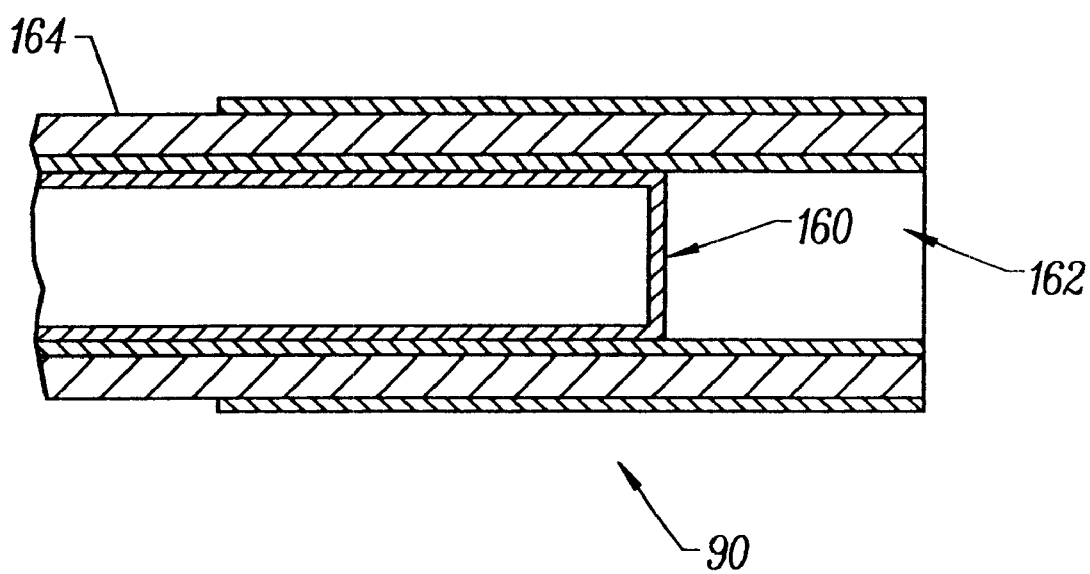
FIG. 13 is a side view of the distal portion of the shaft of an electrosurgical probe, according to one embodiment of the invention.

In some embodiments, the probe 20/90 will also include one or more aspiration electrode(s) coupled to the aspiration lumen for inhibiting clogging during aspiration of tissue fragments from the surgical site. As shown in FIG. 9, one or more of the active electrodes 104 may comprise loop electrodes 140 that extend across distal opening 209 of the suction lumen within shaft 100. In the representative embodiment, two of the active electrodes 104 comprise loop electrodes 140 that cross over the distal opening 209. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 10 and 11. Alternatively, the electrodes may be formed within suction lumen proximal to the distal opening 209, as shown in FIG. 13. The main function of loop electrodes 140 is to ablate portions of tissue that are drawn into the suction lumen to prevent clogging of the lumen.

In some embodiments, loop electrodes 140 are electrically isolated from the other active electrodes 104. In other embodiments, the loop electrodes 140 and active electrodes 104 may be electrically connected to each other such that both are activated together. Loop electrodes 140 may or may not be electrically isolated from each other. Loop electrodes 140 will usually extend only about 0.05 mm to 4 mm, preferably about 0.1 mm to 1 mm from the tissue treatment surface of electrode support member 102.

Figure 10:
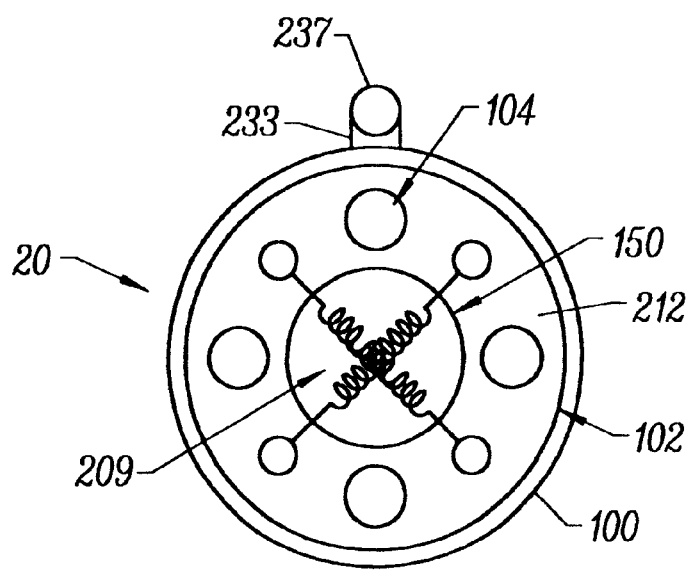
Figure 11:
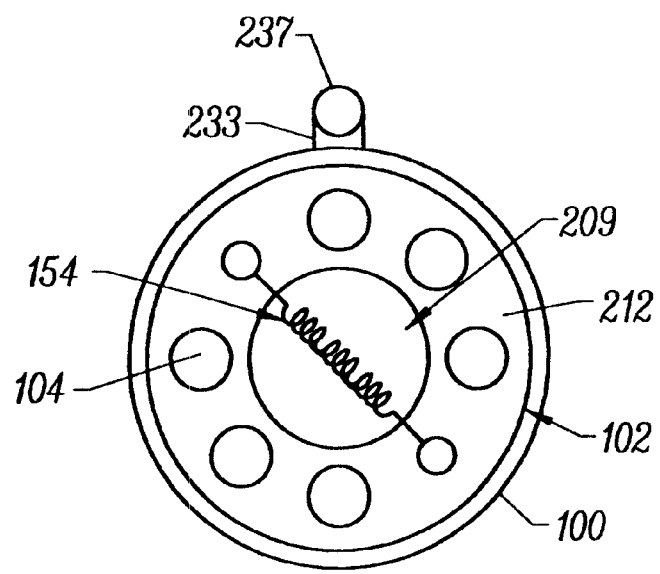

Referring now to FIGS. 10 and 11, alternative embodiments for aspiration electrodes will now be described. As shown in FIG. 10, the aspiration electrodes may comprise a pair of coiled electrodes 150 that extend across distal opening 209 of the suction lumen. The larger surface area of the coiled electrodes 150 usually increases the effectiveness of the electrodes 150 in ablating tissue fragments which may approach or pass through opening 209. In FIG. 11, the aspiration electrode comprises a single coiled electrode 154 extending across the distal opening 209 of the suction lumen. This single electrode 152 may be sufficient to inhibit clogging of the suction lumen. Alternatively, the aspiration electrodes may be positioned within the suction lumen proximal to the distal opening 209. Preferably, these electrodes are close to opening 209 so that tissue does not clog the opening 209 before it reaches electrodes 154. In this embodiment, a separate return electrode (not shown) may be provided within the suction lumen to confine the electric currents therein.

Figure 12:
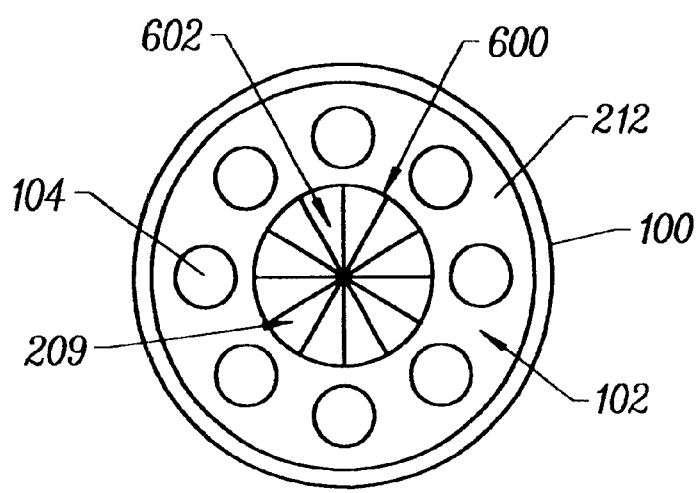

Referring to FIG. 12, another embodiment of the present invention incorporates a wire mesh electrode 600 extending across the distal portion of aspiration lumen 162. As shown, mesh electrode 600 includes a plurality of openings 602 to allow fluids and tissue fragments to flow therethrough into aspiration lumen 162. The size of the openings 602 will vary depending on a variety of factors. The mesh electrode may be coupled to the distal or proximal surfaces of support member 102. Wire mesh electrode 600 comprises a conductive material, such as titanium, tantalum, steel, stainless steel, tungsten, copper, gold or the like. In the representative embodiment, wire mesh electrode 600 comprises a different material having a different electric potential than the active electrode(s) 104. Preferably, mesh electrode 600 comprises steel and active electrode(s) 104 comprises tungsten. Applicant has found that a slight variance in the electrochemical potential of mesh electrode 600 and active electrode(s) 104 improves the performance of the device. Of course, it will be recognized that mesh electrode 600 may be electrically insulated from active electrode(s) 104, as in previous embodiments.

Referring to FIG. 13, another embodiment of the present invention incorporates an aspiration electrode 160 within an aspiration lumen 162 of the probe. As shown, the electrode 160 is positioned just proximal of distal opening 209 so that the tissue fragments are ablated as they enter lumen 162. In the representative embodiment, aspiration electrode 160 comprises a loop electrode that extends across the aspiration lumen 162. However, it will be recognized that many other configurations are possible. In this embodiment, the return electrode 164 is located towards the exterior of the shaft, as in the previously described embodiments. Alternatively, the return electrode(s) may be located within the aspiration lumen 162 with the aspiration electrode 160. For example, the inner insulating coating 163 may be exposed at portions within the lumen 162 to provide a conductive path between this exposed portion of return electrode 164 and the aspiration electrode 160. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 162 along with the tissue fragments.

Referring now to FIGS. 14A–14C, an alternative embodiment incorporating a metal screen 610 is illustrated. As shown, metal screen 610 has a plurality of peripheral openings 612 for receiving active electrodes 104, and a plurality of inner openings 614 for allowing aspiration of fluid and tissue through an opening 609 of the aspiration lumen. As shown, screen 610 is press fitted over active electrodes 104 and then adhered to shaft 100 of probe 20/90. Similar to the mesh electrode embodiment, metal screen 610 may comprise a variety of conductive metals, such as titanium, tantalum, steel, stainless steel, tungsten, copper, gold or the like. In the representative embodiment, metal screen 610 is coupled directly to, or integral with, active electrode(s) 104. In this embodiment, the active electrode(s) 104 and the metal screen 610 are electrically coupled to each other.

Figure 15A:
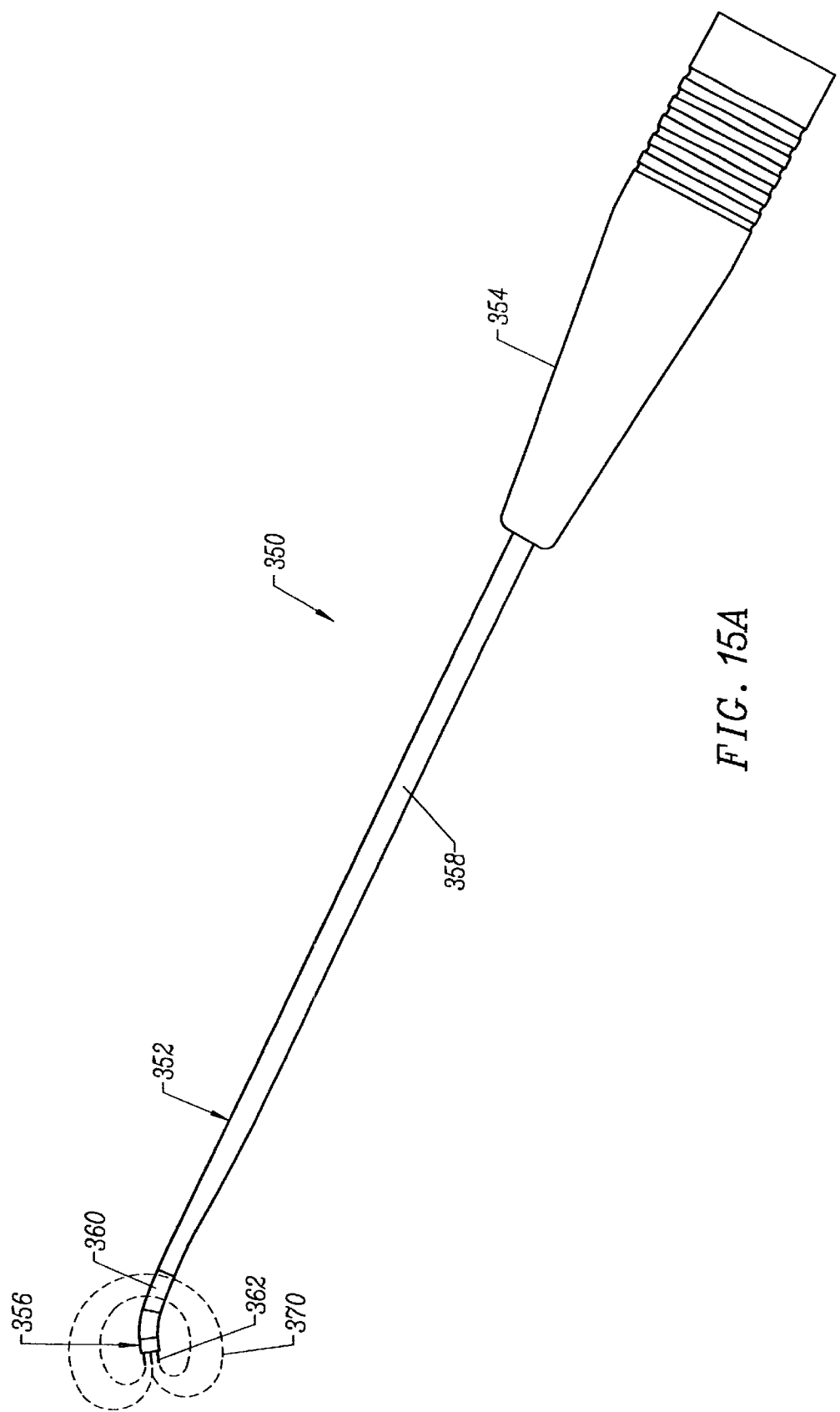
FIGS. 15A–15D illustrate four embodiments of electrosurgical probes specifically designed for treating spinal defects.

FIGS. 15A to 15D illustrate embodiments of an electrosurgical probe 350 specifically designed for the treatment of herniated or diseased spinal discs. Referring to FIG. 15A, probe 350 comprises an electrically conductive shaft 352, a handle 354 coupled to the proximal end of shaft 352 and an electrically insulating support member 356 at the distal end of shaft 352. Probe 350 further includes a shrink wrapped insulating sleeve 358 over shaft 352, and an exposed portion of shaft 352 that functions as the return electrode 360. In the representative embodiment, probe 350 comprises a plurality of active electrodes 362 extending from the distal end of support member 356. As shown, return electrode 360 is spaced a further distance from active electrodes 362 than in the embodiments described above. In this embodiment, the return electrode 360 is spaced a distance of about 2.0 mm to 50 mm, preferably about 5 mm to 25 mm from active electrodes 362. In addition, return electrode 360 has a larger exposed surface area than in previous embodiments, having a length in the range of about 2.0 mm to 40 mm, preferably about 5 mm to 20 mm. Accordingly, electric current passing from active electrodes 362 to return electrode 360 will follow a current flow path 370 that is further away from shaft 352 than in the previous embodiments. In some applications, this current flow path 370 results in a deeper current penetration into the surrounding tissue with the same voltage level, and thus increased thermal heating of the tissue. As discussed above, this increased thermal heating may have advantages in some applications of treating disc or other spinal abnormalities. Typically, it is desired to achieve a tissue temperature in the range of about 60° C. to 100° C. to a depth of about 0.2 mm to 5 mm, usually about 1 mm to 2 mm. The voltage required for this thermal damage will partly depend on the electrode configurations, the conductivity of the tissue and the area immediately surrounding the electrodes, the time period in which the voltage is applied and the depth of tissue damage desired. With the electrode configurations described in FIGS. 15A–15D, the voltage level for thermal heating will usually be in the range of about 20 volts rms to 300 volts rms, preferably about 60 volts rms to 200 volts rms. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked or ablated, which is undesirable.

In alternative embodiments, the electrosurgical system used in conjunction with probe 350 may include a dispersive return electrode 450 (see FIG. 16) for switching between bipolar and monopolar modes. In this embodiment, the system will switch between an ablation mode, where the dispersive pad 450 is deactivated and voltage is applied between active and return electrodes 362, 360, and a subablation or thermal heating mode, where the active electrode(s) 362 are deactivated and voltage is applied between the dispersive pad 450 and the return electrode 360. In the subablation mode, a lower voltage is typically applied and the return electrode 360 functions as the active electrode to provide thermal heating and/or coagulation of tissue surrounding return electrode 360.

Figure 15B:
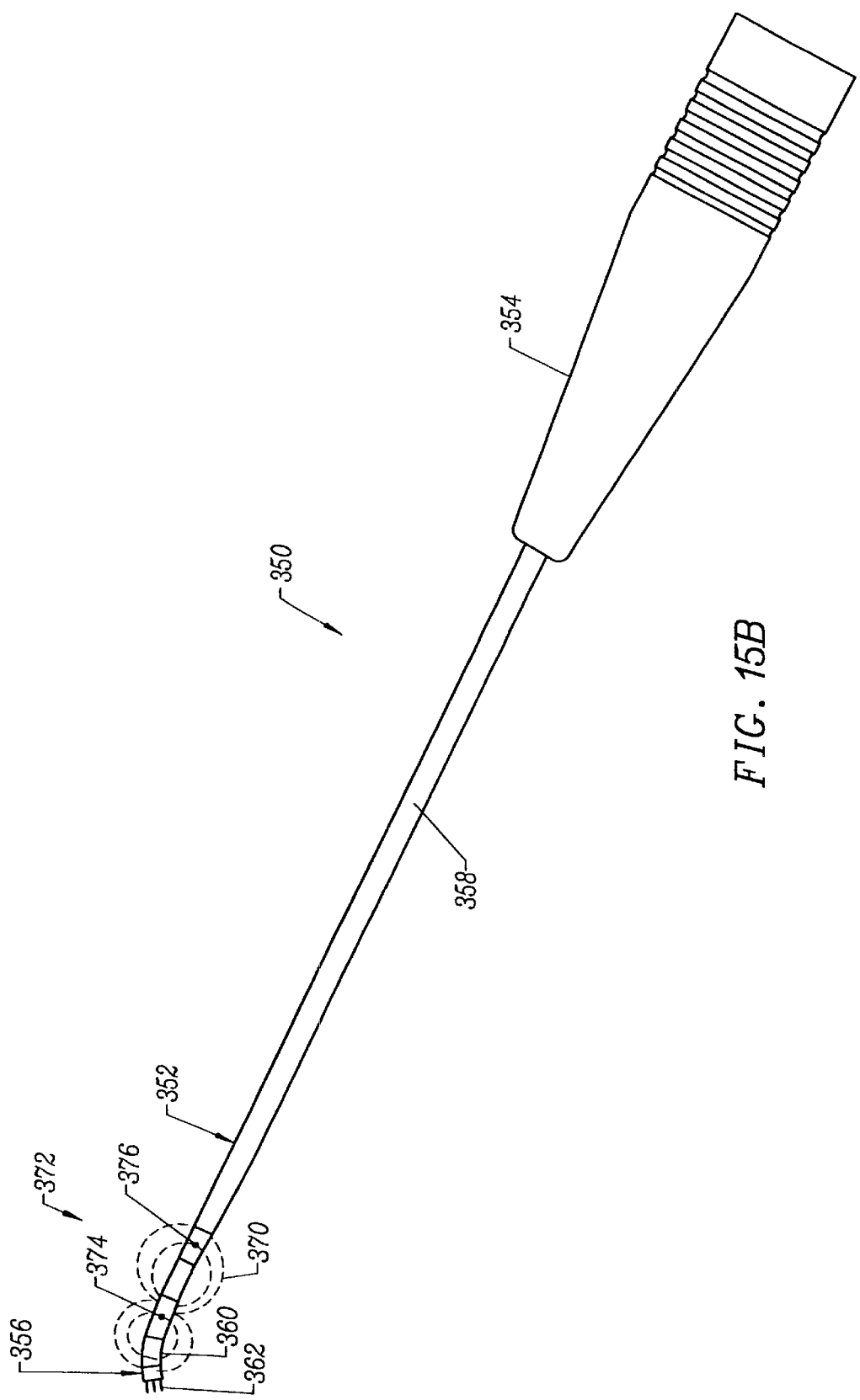

FIG. 15B illustrates yet another embodiment of the present invention. As shown, electrosurgical probe 350 comprises an electrode assembly 372 having one or more active electrode(s) 362 and a proximally spaced return electrode 360 as in previous embodiments. Return electrode 360 is typically spaced about 0.5 mm to 25 mm, preferably 1.0 mm to 5.0 mm from the active electrode(s) 362, and has an exposed length of about 1 mm to 20 mm. In addition, electrode assembly 372 includes two additional electrodes 374, 376 spaced axially on either side of return electrode 360. Electrodes 374, 376 are typically spaced about 0.5 mm to 25 mm, preferably about 1 mm to 5 mm from return electrode 360. In the representative embodiment, the additional electrodes 374, 376 are exposed portions of shaft 352, and the return electrode 360 is electrically insulated from shaft 352 such that a voltage difference may be applied between electrodes 374, 376 and electrode 360. In this embodiment, probe 350 may be used in at least two different modes, an ablation mode and a subablation or thermal heating mode. In the ablation mode, voltage is applied between active electrode(s) 362 and return electrode 360 in the presence of electrically conductive fluid, as described above. In the ablation mode, electrodes 374, 376 are deactivated. In the thermal heating or coagulation mode, active electrode(s) 362 are deactivated and a voltage difference is applied between electrodes 374, 376 and electrode 360 such that a high frequency current 370 flows therebetween, as shown in FIG. 15B. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 372, 374.

Figure 15C:
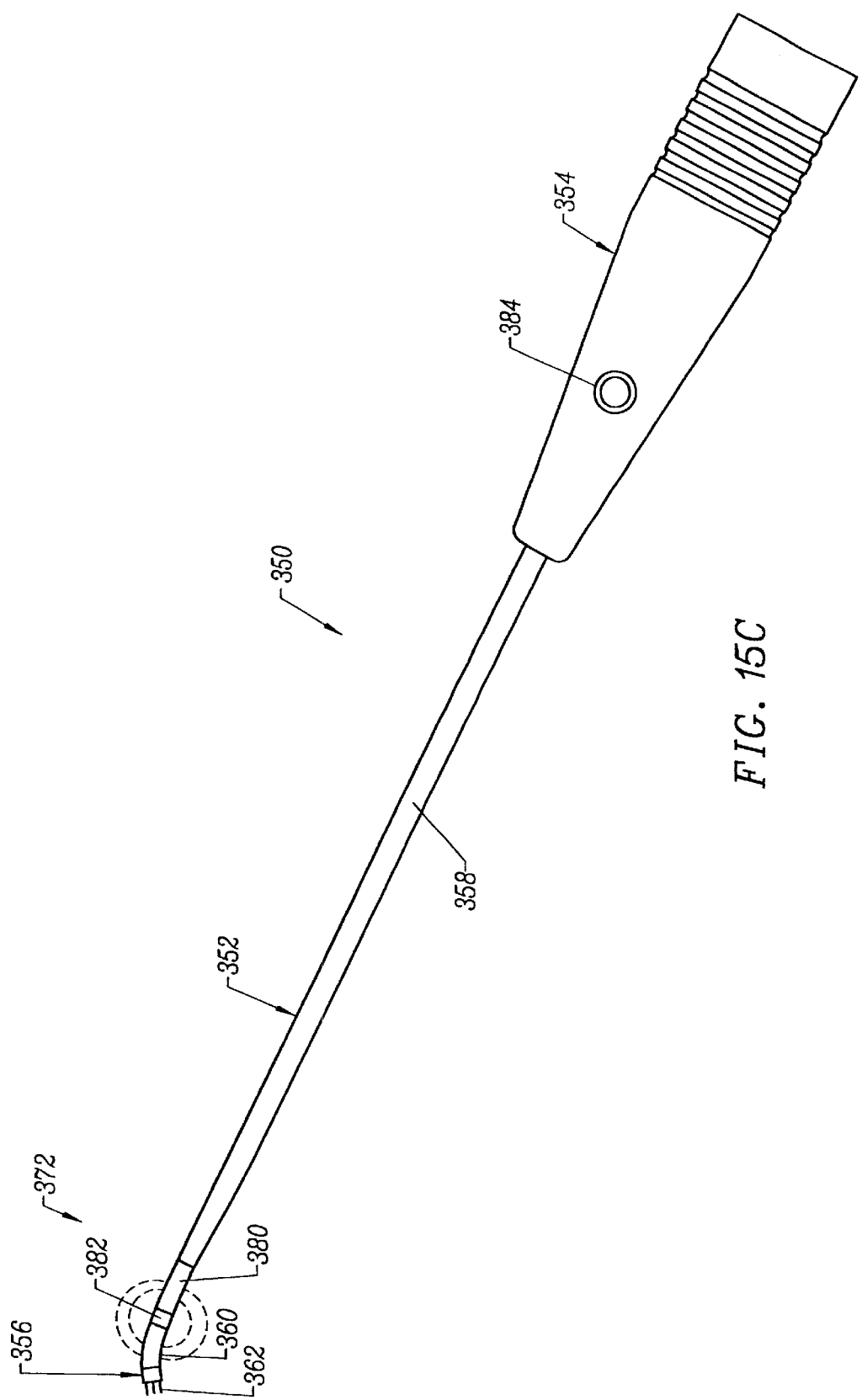

FIG. 15C illustrates another embodiment of probe 350 incorporating an electrode assembly 372 having one or more active electrode(s) 362 and a proximally spaced return electrode 360 as in previous embodiments. Return electrode 360 is typically spaced about 0.5 mm to 25 mm, preferably 1.0 mm to 5.0 mm from the active electrode(s) 362, and has an exposed length of about 1 mm to 20 mm. In addition, electrode assembly 372 includes a second active electrode 380 separated from return electrode 360 by an electrically insulating spacer 382. In this embodiment, handle 354 includes a switch 384 for toggling probe 350 between at least two different modes, an ablation mode and a subablation or thermal heating mode. In the ablation mode, voltage is applied between active electrode(s) 362 and return electrode 360 in the presence of electrically conductive fluid, as described above. In the ablation mode, electrode 380 is deactivated. In the thermal heating or coagulation mode, active electrode(s) 362 may be deactivated and a voltage difference is applied between electrode 380 and electrode 360 such that a high frequency current 370 flows therebetween. Alternatively, active electrode(s) 362 may not be deactivated as the higher resistance of the smaller electrodes may automatically send the electric current to electrode 380 without having to physically decouple electrode(s) 362 from the circuit. In the thermal heating mode, a lower voltage is typically applied below the threshold for plasma formation and ablation, but sufficient to cause some thermal damage to the tissue immediately surrounding the electrodes without vaporizing or otherwise debulking this tissue so that the current 370 provides thermal heating and/or coagulation of tissue surrounding electrodes 360, 380.

Of course, it will be recognized that a variety of other embodiments may be used to accomplish similar functions as the embodiments described above. For example, electrosurgical probe 350 may include a plurality of helical bands formed around shaft 352, with one or more of the helical bands having an electrode coupled to the portion of the band such that one or more electrodes are formed on shaft 352 spaced axially from each other.

Figure 15D:
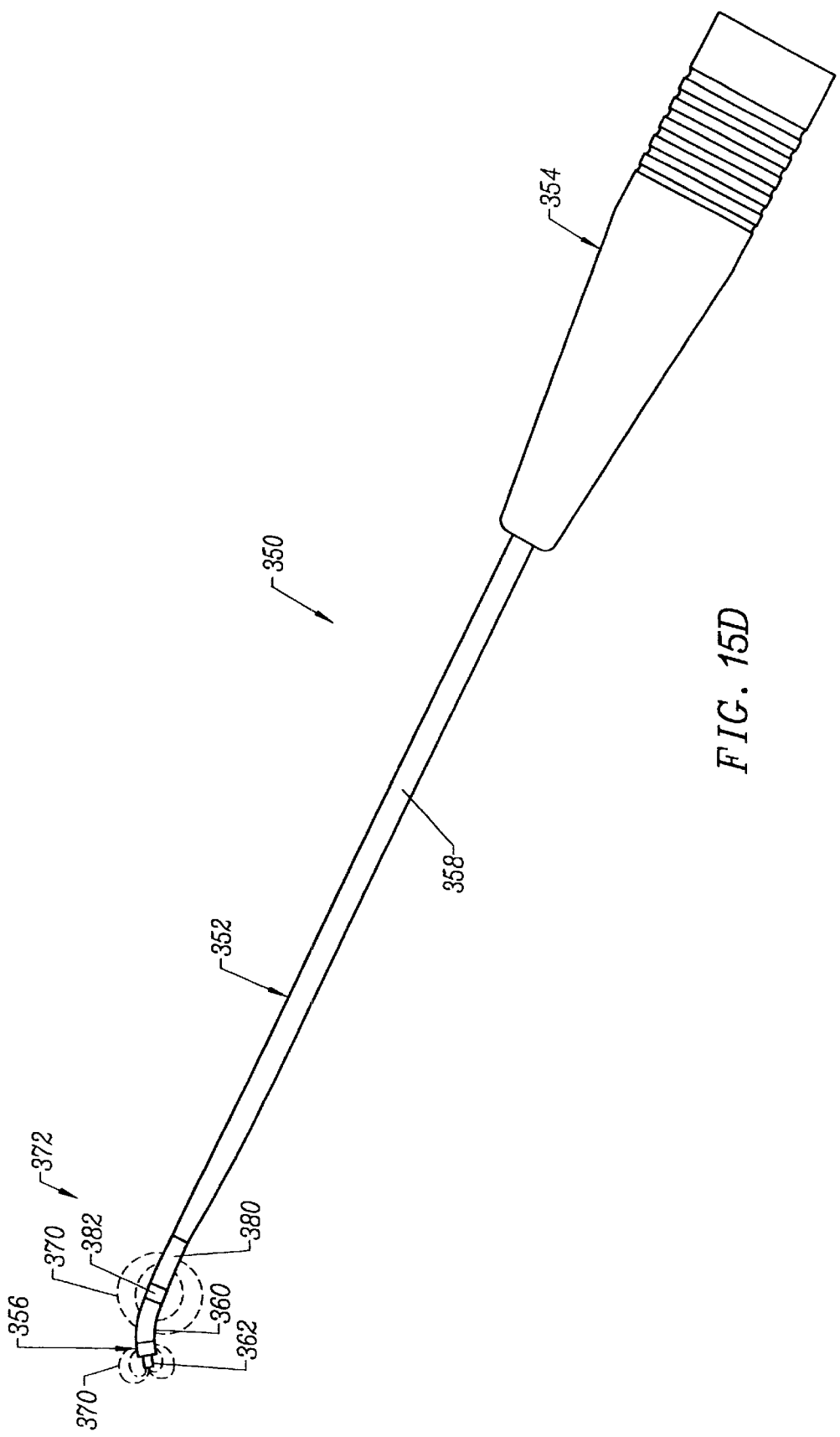

FIG. 15D illustrates another embodiment of the invention designed for channeling through tissue and creating lesions therein to treat spinal discs and/or snoring and sleep apnea. As shown, probe 350 is similar to the probe in FIG. 15C having a return electrode 360 and a third, coagulation electrode 380 spaced proximally from the return electrode 360. In this embodiment, active electrode 362 comprises a single electrode wire extending distally from insulating support member 356. Of course, the active electrode 362 may have a variety of configurations to increase the current densities on its surfaces, e.g., a conical shape tapering to a distal point, a hollow cylinder, loop electrode and the like.

In the representative embodiment, support members 356 and 382 are constructed of a material, such as ceramic, glass, silicone and the like. The proximal support member 382 may also comprise a more conventional organic material as this support member 382 will generally not be in the presence of a plasma that would otherwise etch or wear away an organic material.

The probe 350 in FIG. 15D does not include a switching element. In this embodiment, all three electrodes are activated when the power supply is activated. The return electrode 360 has an opposite polarity from the active and coagulation electrodes 362, 380 such that current 370 flows from the latter electrodes to the return electrode 360 as shown. In the preferred embodiment, the electrosurgical system includes a voltage reduction element or a voltage reduction circuit for reducing the voltage applied between the coagulation electrode 380 and return electrode 360. The voltage reduction element allows the power supply 28 to, in effect, apply two different voltages simultaneously to two different electrodes. Thus, for channeling through tissue, the operator may apply a voltage sufficient to provide ablation of the tissue at the tip of the probe (i.e., tissue adjacent to the active electrode 362). At the same time, the voltage applied to the coagulation electrode 380 will be insufficient to ablate tissue. For thermal heating or coagulation of tissue, for example, the voltage reduction element will serve to reduce a voltage of about 100 volts rms to 300 volts rms to about 45 volts rms to 90 volts rms, which is a suitable voltage for coagulation of tissue without ablation (e.g., molecular dissociation) of the tissue.

In the representative embodiment, the voltage reduction element comprises a pair of capacitors forming a bridge divider(not shown) coupled to the power supply and coagulation electrode 380. The capacitors usually have a capacitance of about 200 pF to 500 pF (at 500 volts) and preferably about 300 pF to 350 pF (at 500 volts). Of course, the capacitors may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 350 may include a coded resistor (not shown) that is constructed to lower the voltage applied between the return and coagulation electrodes 360, 380, respectively. In addition, electrical circuits may be employed for this purpose.

Of course, for some procedures, the probe will typically not require a voltage reduction element. Alternatively, the probe may include a voltage increasing element or circuit, if desired. Alternatively or additionally, cable 22/34 that couples power supply 28 to the probe 90 may be used as a voltage reduction element. The cable has an inherent capacitance that can be used to reduce the power supply voltage if the cable is placed into the electrical circuit between the power supply, the active electrodes and the return electrode. In this embodiment, cable 22/34 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In one specific embodiment, the probe 350 is manufactured by first inserting an electrode wire (active electrode 362) through a ceramic tube (insulating member 356) such that a distal portion of the wire extends through the distal portion of the tube, and bonding the wire to the tube, typically with an appropriate epoxy. A stainless steel tube (return electrode 360) is then placed over the proximal portion of the ceramic tube, and a wire (e.g., nickel wire) is bonded, typically by spot welding, to the inside surface of the stainless steel tube. The stainless steel tube is coupled to the ceramic tube by epoxy, and the device is cured in an oven or other suitable heat source. A second ceramic tube (insulating member 382) is then placed inside of the proximal portion of the stainless steel tube, and bonded in a similar manner. The shaft 358 is then bonded to the proximal portion of the second ceramic tube, and an insulating sleeve (e.g. polyimide) is wrapped around shaft 358 such that only a distal portion of the shaft is exposed (i.e., coagulation electrode 380). The nickel wire connection will extend through the center of shaft 358 to connect return electrode 360 to the power supply. The active electrode 362 may form a distal portion of shaft 358, or it may also have a connector extending through shaft 358 to the power supply.

In use, the physician positions active electrode 362 adjacent to the tissue surface to be treated (i.e., a spinal disc). The power supply is activated to provide an ablation voltage between active and return electrodes 362, 360, respectively, and a coagulation or thermal heating voltage between coagulation and return electrodes 380, 360, respectively. An electrically conductive fluid can then be provided around active electrode 362, and in the junction between the active and return electrodes 360, 362 to provide a current flow path therebetween. This may be accomplished in a variety of manners, as discussed above. The active electrode 362 is then advanced through the space left by the ablated tissue to form a channel in the disc. During ablation, the electric current between the coagulation and return electrode is typically insufficient to cause any damage to the surface of the tissue as these electrodes pass through the tissue surface into the channel created by active electrode 362. Once the physician has formed the channel to the appropriate depth, he or she will cease advancement of the active electrode, and will either hold the instrument in place for approximately 5 seconds to 30 seconds, or can immediately remove the distal tip of the instrument from the channel (see detailed discussion of this below). In either event, when the active electrode is no longer advancing, it will eventually stop ablating tissue.

Prior to entering the channel formed by the active electrode 362, an open circuit exists between return and coagulation electrodes 360, 380. Once coagulation electrode 380 enters this channel, electric current will flow from coagulation electrode 380, through the tissue surrounding the channel, to return electrode 360. This electric current will heat the tissue immediately surrounding the channel to coagulate any severed vessels at the surface of the channel. If the physician desires, the instrument may be held within the channel for a period of time to create a lesion around the channel, as discussed in more detail below.

Figure 16:
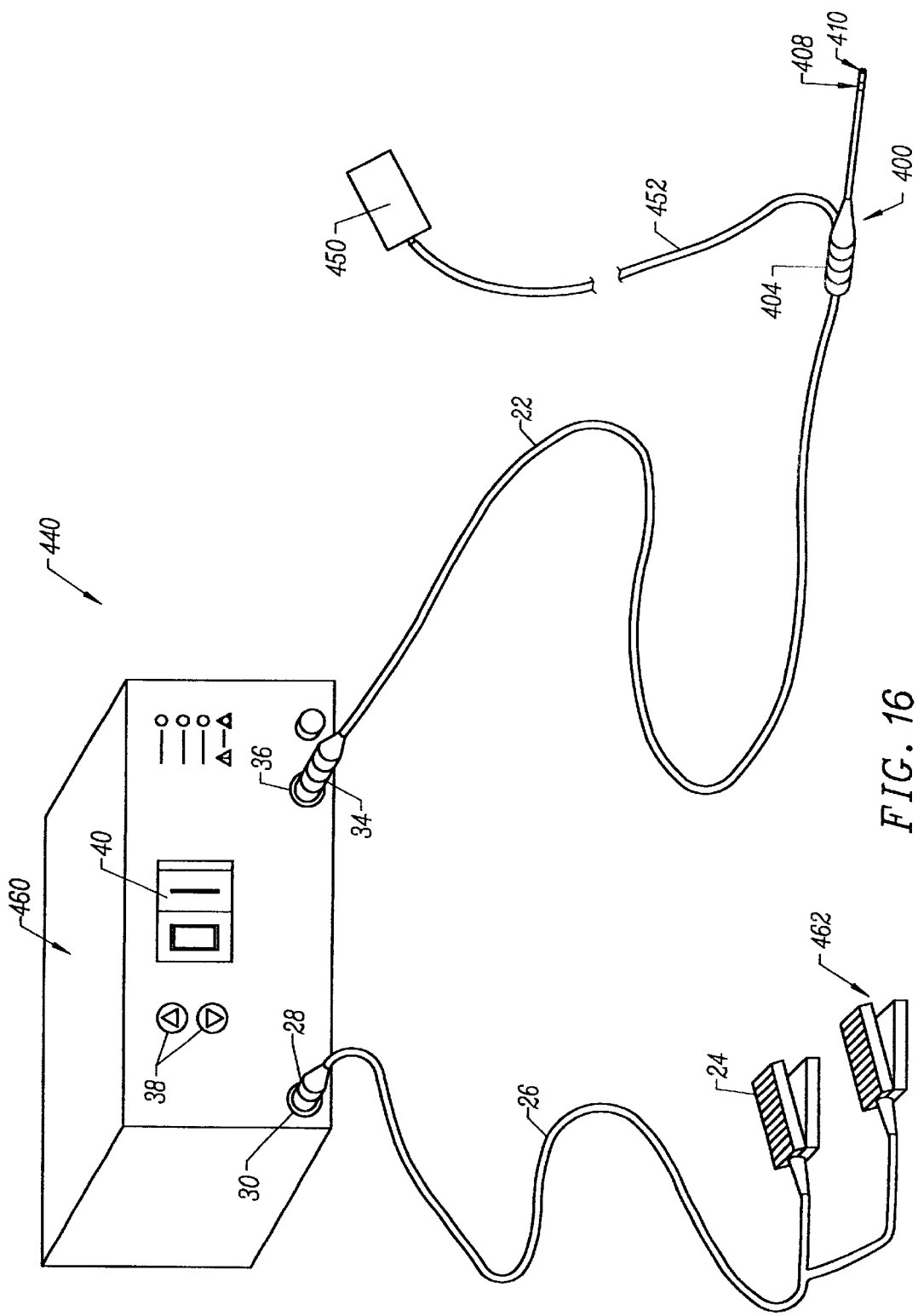
FIG. 16 illustrates an electrosurgical system incorporating a dispersive return pad for monopolar and/or bipolar operations.

FIG. 16 illustrates yet another embodiment of an electrosurgical system 440 incorporating a dispersive return pad 450 attached to the electrosurgical probe 400. In this embodiment, the invention functions in the bipolar mode as described above. In addition, the system 440 may function in a monopolar mode in which a high frequency voltage difference is applied between the active electrode(s) 410, and the dispersive return pad 450. In the exemplary embodiment, the pad 450 and the probe 400 are coupled together, and are both disposable, single-use items. The pad 450 includes an electrical connector 452 that extends into handle 404 of probe 400 for direct connection to the power supply. Of course, the invention would also be operable with a standard return pad that connects directly to the power supply. In this embodiment, the power supply 460 will include a switch, e.g., a foot pedal 462, for switching between the monopolar and bipolar modes. In the bipolar mode, the return path on the power supply is coupled to return electrode 408 on probe 400, as described above. In the monopolar mode, the return path on the power supply is coupled to connector 452 of pad 450, active electrode(s) 410 are decoupled from the electrical circuit, and return electrode 408 functions as the active electrode. This allows the surgeon to switch between bipolar and monopolar modes during, or prior to, the surgical procedure. In some cases, it may be desirable to operate in the monopolar mode to provide deeper current penetration and, thus, a greater thermal heating of the tissue surrounding the return electrodes. In other cases, such as ablation of tissue, the bipolar modality may be preferable to limit the current penetration to the tissue.

In one configuration, the dispersive return pad 450 is adapted for coupling to an external surface of the patient in a region substantially close to the target region. For example, during the treatment of tissue in the head and neck, the dispersive return pad is designed and constructed for placement in or around the patient's shoulder, upper back or upper chest region. This design limits the current path through the patient's body to the head and neck area, which minimizes the damage that may be generated by unwanted current paths in the patient's body, particularly by limiting current flow through the patient's heart. The return pad is also designed to minimize the current densities at the pad, to thereby minimize patient skin burns in the region where the pad is attached.

Figure 17:
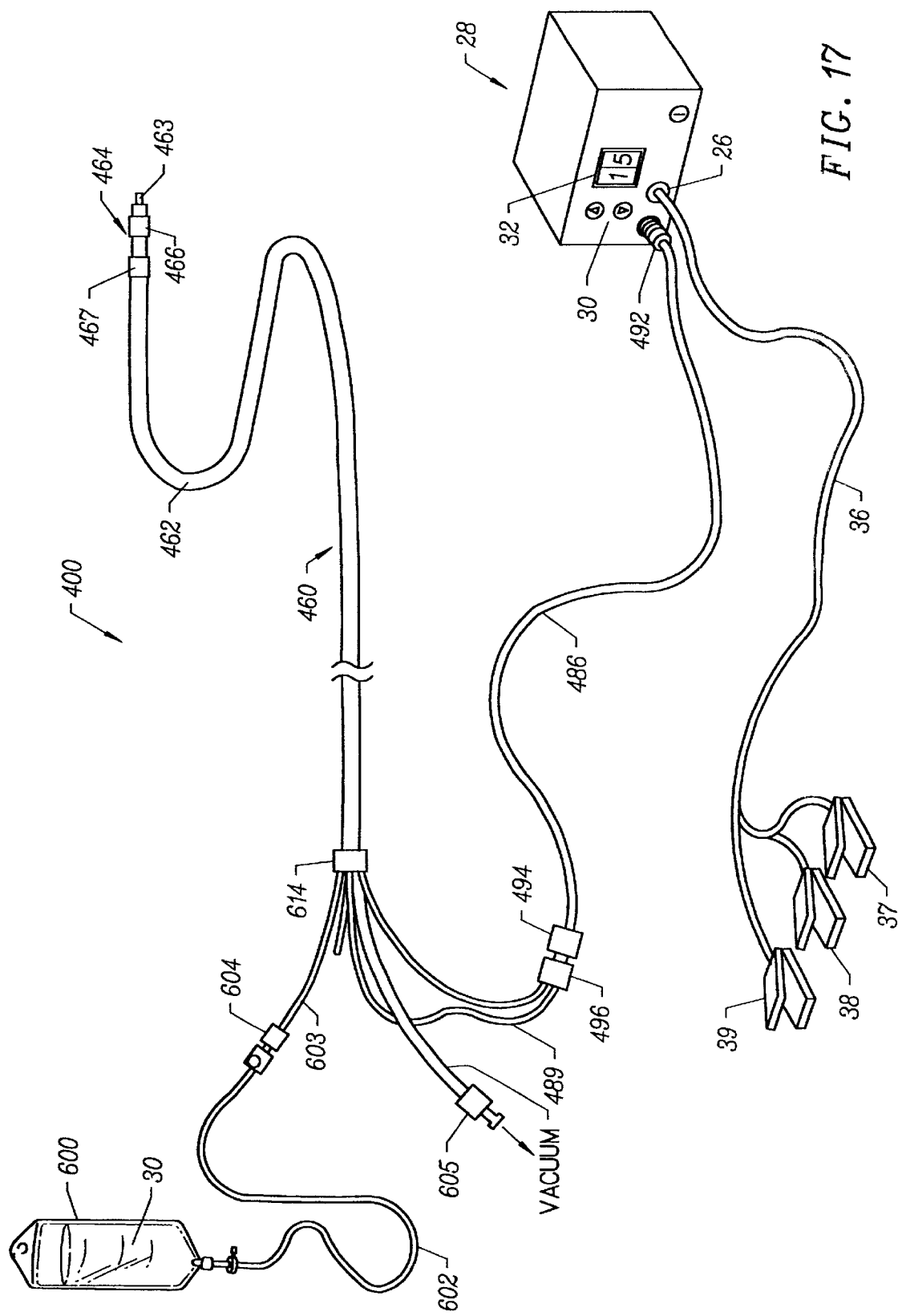
FIG. 17 illustrates a catheter system for electrosurgical treatment of intervertebral discs according to the present invention.
Figure 18:
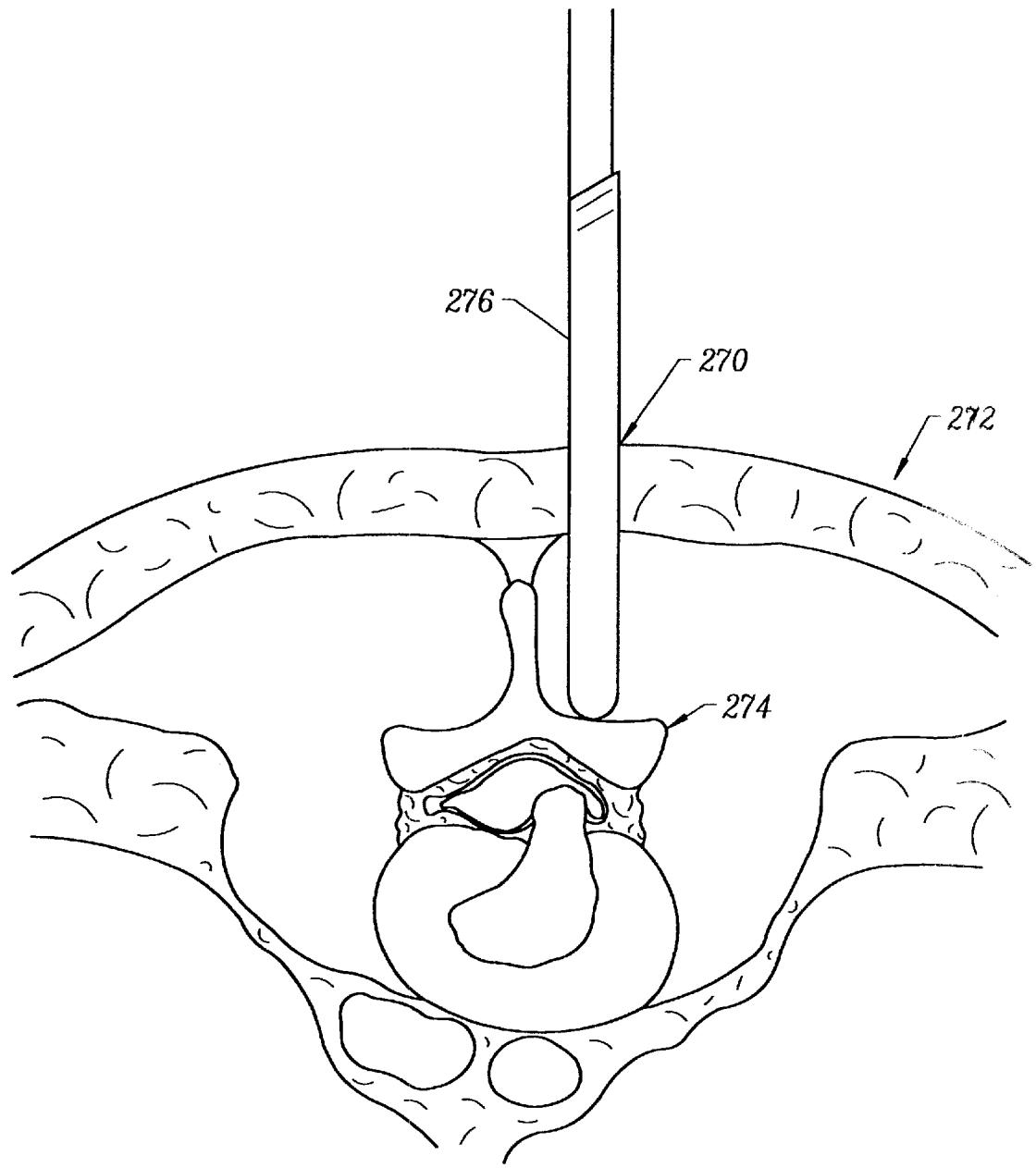
FIGS. 18–22 illustrate a method of performing a microendoscopic discectomy according to the principles of the present invention.

Referring to FIG. 17, the electrosurgical system according to the present invention may also be configured as a catheter system 400. As shown in FIG. 17, a catheter system 400 generally comprises an electrosurgical catheter 460 connected to a power supply 28 by an interconnecting cable 486 for providing high frequency voltage to a target tissue and an irrigant reservoir or source 600 for providing electrically conductive fluid to the target site. Catheter 460 generally comprises an elongate, flexible shaft body 462 including a tissue removing or ablating region 464 at the distal end of body 462. The proximal portion of catheter 460 includes a multi-lumen fitment 614 which provides for interconnections between lumens and electrical leads within catheter 460 and conduits and cables proximal to fitment 614. By way of example, a catheter electrical connector 496 is removably connected to a distal cable connector 494 which, in turn, is removably connectable to generator 28 through connector 492. One or more electrically conducting lead wires (not shown) within catheter 460 extend between one or more active electrodes 463 and a coagulation electrode 467 at tissue ablating region 464 and one or more corresponding electrical terminals (also not shown) in catheter connector 496 via active electrode cable branch 487. Similarly, a return electrode 466 at tissue ablating region 464 is coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque control for rotation of active electrodes during tissue engagement. This rigid portion of the catheter body 462 preferably extends only about 7 mm to 10 mm while the remainder of the catheter body 462 is flexible to provide good trackability during advancement and positioning of the electrodes adjacent target tissue.

In some embodiments, conductive fluid 50 is provided to tissue ablation region 464 of catheter 460 via a lumen (not shown in FIG. 17) within catheter 460. Fluid is supplied to the lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient and tissue ablating region. A control valve 604 may be positioned at the interface of fluid supply line 602 and conduit 603 to allow manual control of the flow rate of electrically conductive fluid 50. Alternatively, a metering pump or flow regulator may be used to precisely control the flow rate of the conductive fluid.

System 400 can further include an aspiration or vacuum system (not shown) to aspirate liquids and gases from the target site. The aspiration system will usually comprise a source of vacuum coupled to fitment 614 by a aspiration connector 605.

The present invention is particularly useful in microendoscopic discectomy procedures, e.g., for decompressing a nerve root with a lumbar discectomy. As shown in FIGS. 18–23, a percutaneous penetration 270 is made in the patients' back 272 so that the superior lamina 274 can be accessed. Typically, a small needle (not shown) is used initially to localize the disc space level, and a guidewire (not shown) is inserted and advanced under lateral fluoroscopy to the inferior edge of the lamina 274. Sequential cannulated dilators 276 are inserted over the guide wire and each other to provide a hole from the incision 220 to the lamina 274. The first dilator may be used to "palpate" the lamina 274, assuring proper location of its tip between the spinous process and facet complex just above the inferior edge of the lamina 274. As shown in FIG. 21, a tubular retractor 278 is then passed over the largest dilator down to the lamina 274. The dilators 276 are removed, establishing an operating corridor within the tubular retractor 278.

Figure 19:
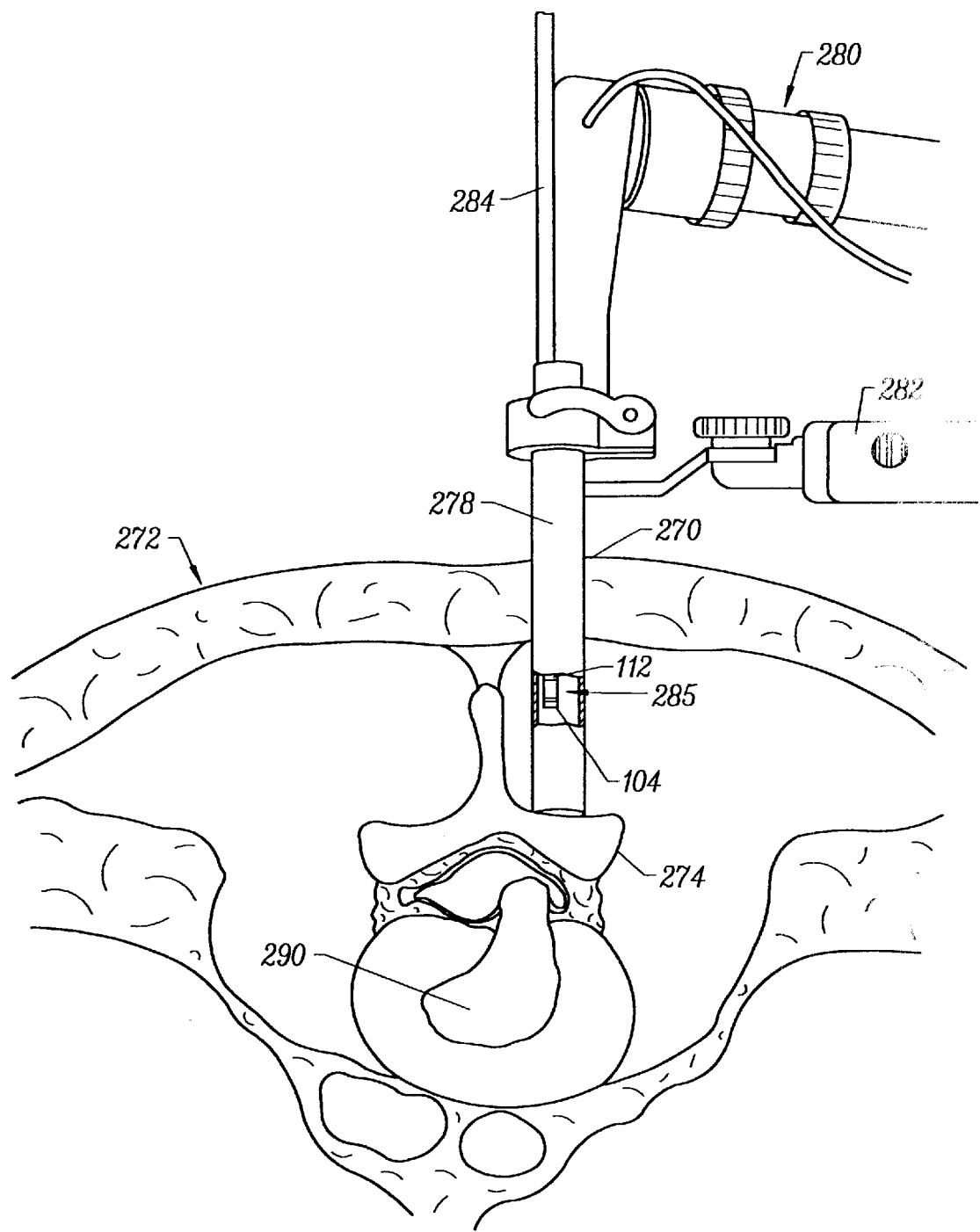

As shown in FIG. 19, an endoscope 280 is then inserted into the tubular retractor 278 and a ring clamp 282 is used to secure the endoscope 280. Typically, the formation of the operating corridor within retractor 278 requires the removal of soft tissue, muscle or other types of tissue that were forced into this corridor as the dilators 276 and retractor 278 were advanced down to the lamina 274. This tissue is usually removed with mechanical instruments, such as pituitary rongeurs, curettes, graspers, cutters, drills, microdebriders, and the like. Unfortunately, these mechanical instruments greatly lengthen and increase the complexity of the procedure. In addition, these instruments sever blood vessels within this tissue, usually causing profuse bleeding that obstructs the surgeon's view of the target site.

According to another aspect of the present invention, an electrosurgical probe or catheter 284 as described above is introduced into the operating corridor within the retractor 278 to remove the soft tissue, muscle and other obstructions from this corridor so that the surgeon can easily access and visualization the lamina 274. Once the surgeon has introduced the probe 284, electrically conductive fluid 285 can be delivered through tube 233 and opening 237 to the tissue (see FIG. 4). The fluid flows past the return electrode 112 to the active electrodes 104 at the distal end of the shaft. The rate of fluid flow is controlled with valve 17 (FIG. 1) such that the zone between the tissue and electrode support 102 is constantly immersed in the fluid. The power supply 28 is then turned on and adjusted such that a high frequency voltage difference is applied between active electrodes 104 and return electrode 112. The electrically conductive fluid provides the conduction path (see current flux lines) between active electrodes 104 and the return electrode 112.

The high frequency voltage is sufficient to convert the electrically conductive fluid (not shown) between the target tissue and active electrode(s) 104 into an ionized vapor layer or plasma (not shown). As a result of the applied voltage difference between active electrode(s) 104 and the target tissue (i.e., the voltage gradient across the plasma layer), charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue.

During the process, the gases will be aspirated through opening 209 and suction tube 211 to a vacuum source. In addition, excess electrically conductive fluid, and other fluids (e.g., blood) will be aspirated from the operating corridor to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure.

Another advantage of the present invention is the ability to precisely ablate soft tissue without causing necrosis or thermal damage to the underlying and surrounding tissues, nerves or bone. In addition, the voltage can be controlled so that the energy directed to the target site is insufficient to ablate the lamina 274 so that the surgeon can literally clean the tissue off the lamina 274, without ablating or otherwise effecting significant damage to the lamina.

Figure 20:
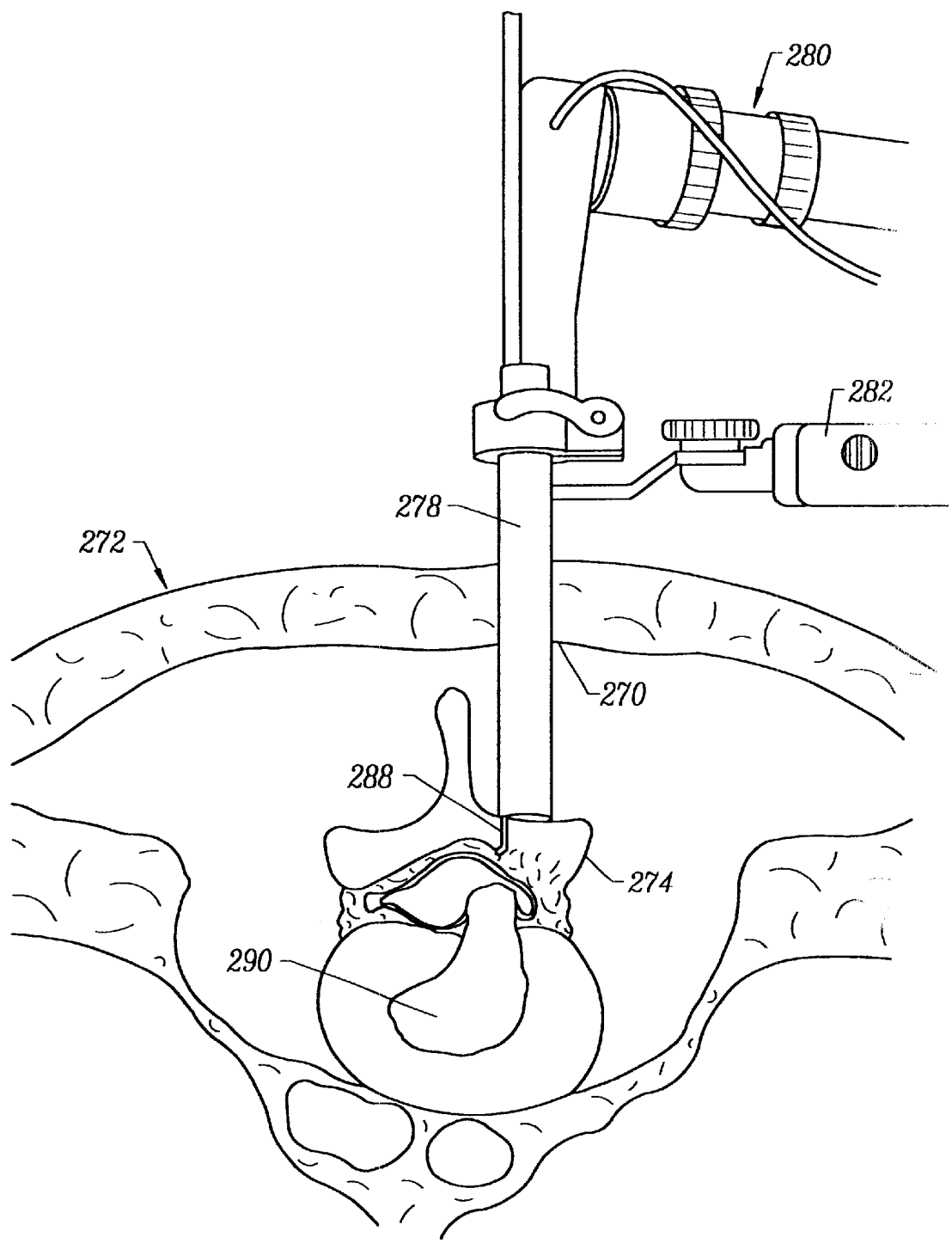
Figure 21:
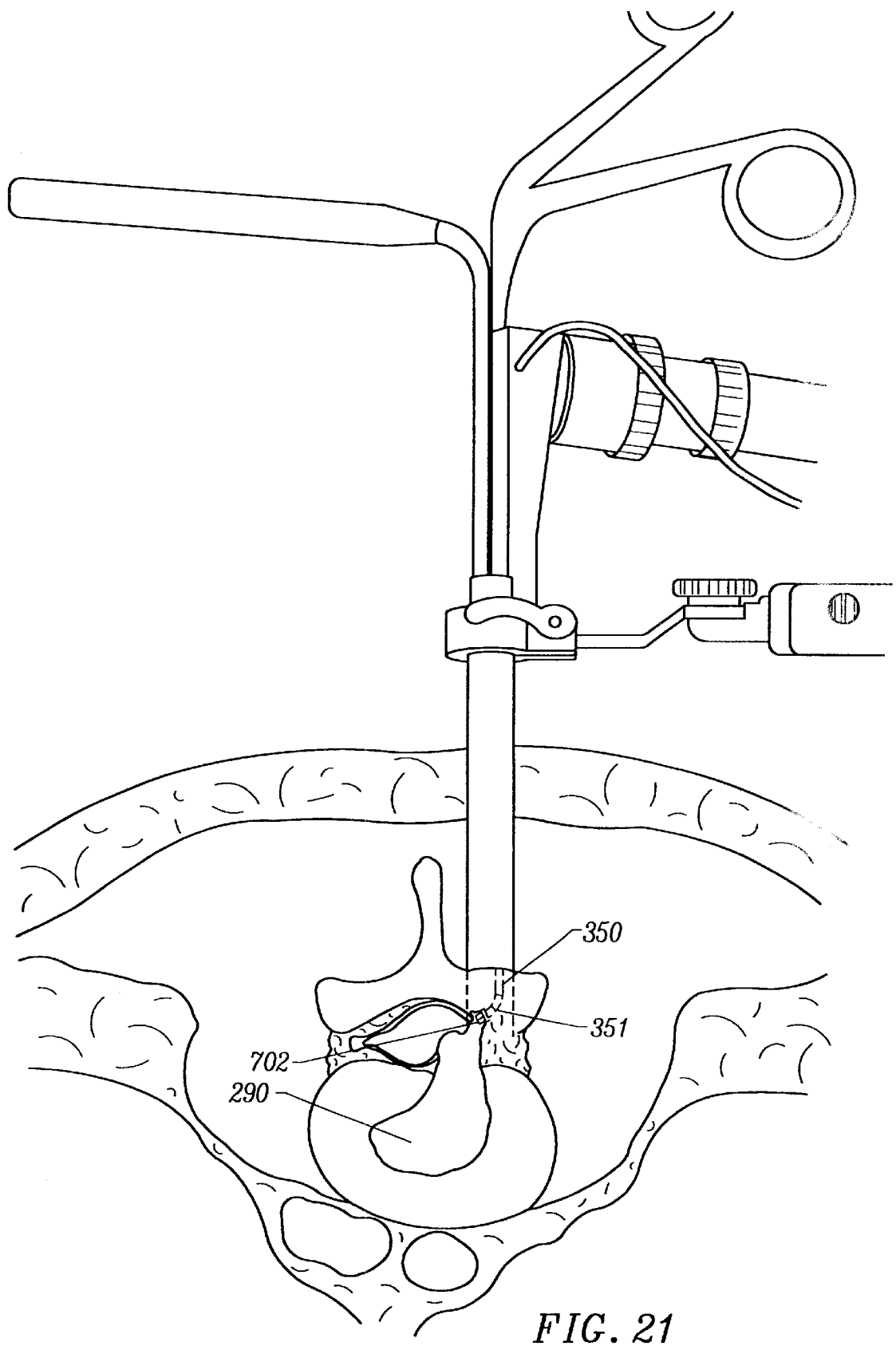

Referring now to FIGS. 20 and 21, once the operating corridor is sufficiently cleared, a laminotomy and medial facetectomy is accomplished either with conventional techniques (e.g., Kerrison punch or a high speed drill) or with the electrosurgical probe 284 as discussed above. After the nerve root is identified, medical retraction can be achieved with a retractor 288, or the present invention can be used to precisely ablate the disc. If necessary, epidural veins are cauterized either automatically or with the coagulation mode of the present invention. If an annulotomy is necessary, it can be accomplished with a microknife or the ablation mechanism of the present invention while protecting the nerve root with the retractor 288. The herniated disc 290 is then removed with a pituitary rongeur in a standard fashion, or once again through ablation as described above.

In another embodiment, the present invention involves a channeling technique in which small holes or channels are formed within the disc 290, and thermal energy is applied to the tissue surface immediately surrounding these holes or channels to cause thermal damage to the tissue surface, thereby stiffening and debulking the surrounding tissue structure of the disc. Applicant has discovered that such stiffening of the tissue structure in the disc helps to reduce the pressure applied against the spinal nerves by the disc, thereby relieving back and neck pain.

As shown in FIG. 21, the electrosurgical instrument 350 is introduced to the target site at the disc 290 as described above, or in another percutaneous manner (see FIGS. 23–25 below). The electrode assembly 351 is positioned adjacent to or against the disc surface, and electrically conductive fluid is delivered to the target site, as described above. Alternatively, the conductive fluid is applied to the target site, or the distal end of probe 350 is dipped into conductive fluid or gel prior to introducing the probe 350 into the patient. The power supply 28 is then activated and adjusted such that a high frequency voltage difference is applied to the electrode assembly as described above.

Depending on the procedure, the surgeon may translate or otherwise move the electrodes relative to the target disc tissue to form holes, channels, stripes, divots, craters or the like within the disc. In addition, the surgeon may purposely create some thermal damage within these holes, or channels to form scar tissue that will stiffen and debulk the disc. In one embodiment, the physician axially translates the electrode assembly 351 into the disc tissue as the tissue is volumetrically removed to form one or more holes 702 therein (see also FIG. 22). The holes 702 will typically have a diameter of less than 2 mm, preferably less than 1 mm. In another embodiment (not shown), the physician translates the active electrode across the outer surface of the disc to form one or more channels or troughs. Applicant has found that the present invention can quickly and cleanly create such holes, divots or channels in tissue with the cold ablation technology described herein. A more complete description of methods for forming holes or channels in tissue can be found in U.S. Pat. No. 5,683,366, the complete disclosure of which is incorporated herein by reference for all purposes.

Figure 22:
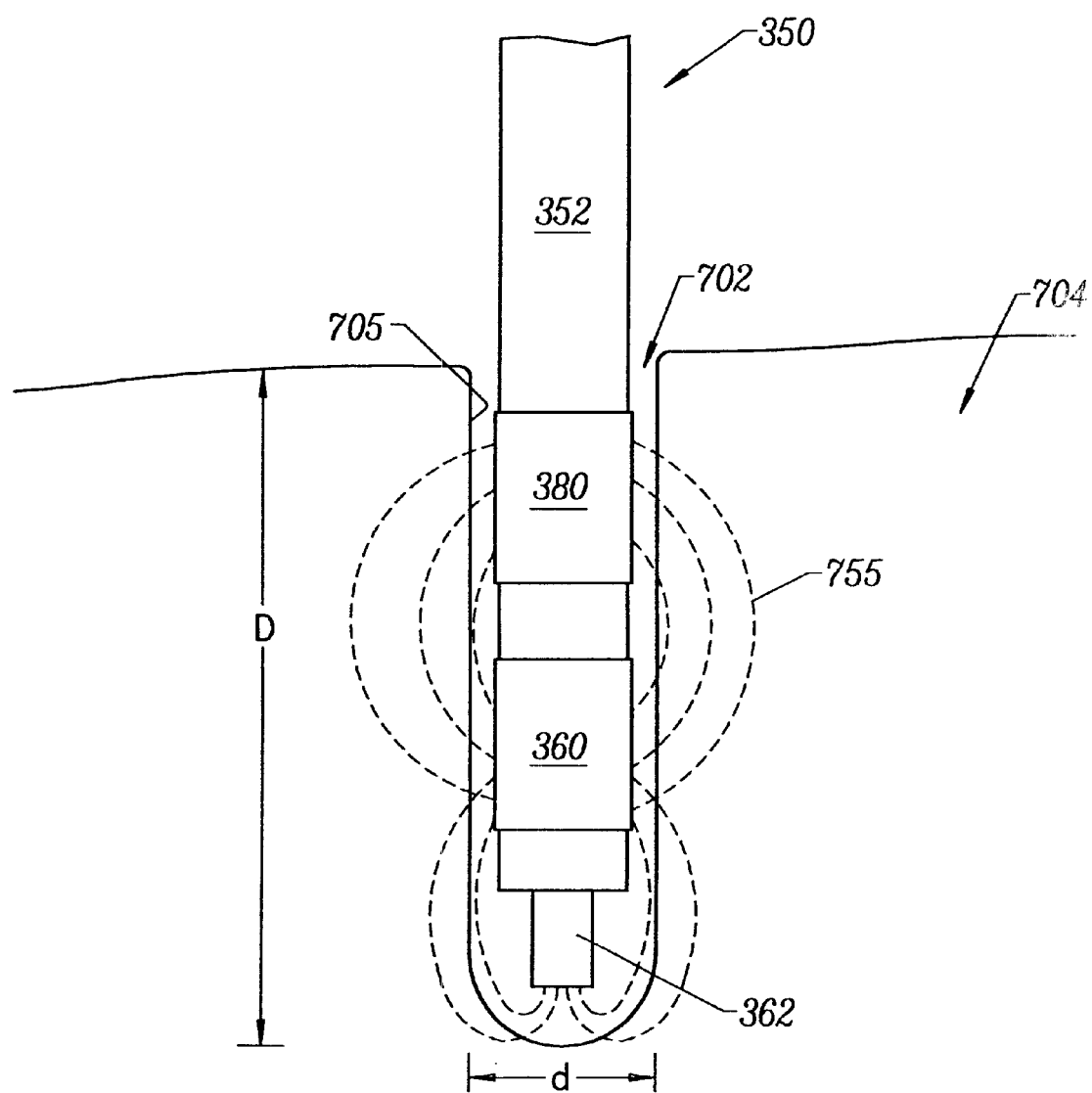

FIG. 22 is a more detailed viewed of the probe 350 of FIG. 15D forming a hole 702 in a disc 290. Hole 702 is preferably formed with the methods described in detail above. Namely, a high frequency voltage difference is applied between active and return electrodes 362, 360, respectively, in the presence of an electrically conductive fluid such that an electric current 361 passes from the active electrode 362, through the conductive fluid, to the return electrode 360. As shown in FIG. 22, this will result in shallow or no current penetration into the disc tissue 704. The fluid may be delivered to the target site, applied directly to the target site, or the distal end of the probe may be dipped into the fluid prior to the procedure. The voltage is sufficient to vaporize the fluid around active electrode 362 to form a plasma with sufficient energy to effect molecular dissociation of the tissue. The distal end of probe 350 is then axially advanced through the tissue as the tissue is removed by the plasma in front of the probe 350. The holes 702 will typically have a depth D in the range of about 0.5 cm to 2.5 cm, preferably about 1.2 cm to 1.8 cm, and a diameter d of about 0.5 mm to 5 mm, preferably about 1.0 mm to 3.0 mm. The exact diameter will, of course, depend on the diameter of the electrosurgical probe used for the procedure.

During the formation of each hole 702, the conductive fluid between active and return electrodes 362, 360 will generally minimize current flow into the surrounding tissue, thereby minimizing thermal damage to the tissue. Therefore, severed blood vessels on the surface 705 of the hole 702 may not be coagulated as the electrodes 362 advance through the tissue. In addition, in some procedures, it may be desired to thermally damage the surface 705 of the hole 702 to stiffen the tissue. For these reasons, it may be desired in some procedures to increase the thermal damage caused to the tissue surrounding hole 702. In the embodiment shown in FIG. 15D, it may be necessary to either: (1) withdraw the probe 350 slowly from hole 702 after coagulation electrode 380 has at least partially advanced past the outer surface of the disc tissue 704 into the hole 702 (as shown in FIG. 22); or (2) hold the probe 350 within the hole 702 for a period of time, e.g., on the order of 1 seconds to 30 seconds. Once the coagulation electrode is in contact with, or adjacent to, tissue, electric current 755 flows through the tissue surrounding hole 702 and creates thermal damage therein. The coagulation and return electrodes 380, 360 both have relatively large, smooth exposed surfaces to minimize high current densities at their surfaces, which minimizes damage to the surface 705 of hole. Meanwhile, the size and spacing of these electrodes 360, 380 allows for relatively deep current penetration into the tissue 704. In the representative embodiment, the thermal necrosis (not shown) will extend about 1.0 mm to 5.0 mm from surface 705 of hole 702. In this embodiment, the probe may include one or more temperature sensors (not shown) on probe coupled to one or more temperature displays on the power supply 28 such that the physician is aware of the temperature within the hole 702 during the procedure.

In other embodiments, the physician switches the electrosurgical system from the ablation mode to the subablation or thermal heating mode after the hole 702 has been formed. This is typically accomplished by pressing a switch or foot pedal to reduce the voltage applied to a level below the threshold required for ablation for the particular electrode configuration and the conductive fluid being used in the procedure (as described above). In the subablation mode, the physician will then remove the distal end of the probe 350 from the hole 702. As the probe is withdrawn, high frequency current flows from the active electrodes 362 through the surrounding tissue to the return electrode 360. This current flow heats the tissue and coagulates severed blood vessels at surface 705.

In another embodiment, the electrosurgical probe of the present invention can be used to ablate and/or contract soft tissue within the disc 290 to allow the annulus fibrosus 292 to repair itself to prevent reoccurrence of this procedure. For tissue contraction, a sufficient voltage difference is applied between the active electrodes 104 and the return electrode 112 to elevate the tissue temperature from normal body temperatures (e.g., 37° C.) to temperatures in the range of 45° C. to 90° C., preferably in the range from 60° C. to 70° C. This temperature elevation causes contraction of the collagen connective fibers within the disc tissue so that the nucleus pulposus withdraws into the annulus fibrosus 292.

In one method of tissue contraction according to the present invention, an electrically conductive fluid is delivered to the target site as described above, and heated to a sufficient temperature to induce contraction or shrinkage of the collagen fibers in the target tissue. The electrically conductive fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to the active electrode(s) in contact with the electrically conductive fluid. The current emanating from the active electrode(s) 104 heats the fluid and generates a jet or plume of heated fluid, which is directed towards the target tissue. The heated fluid elevates the temperature of the collagen sufficiently to cause hydrothermal shrinkage of the collagen fibers. The return electrode 112 draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the active electrode(s) 104 are held away from the tissue a sufficient distance such that the RF current does not pass into the tissue at all, but rather passes through the electrically conductive fluid back to the return electrode. In this embodiment, the primary mechanism for imparting energy to the tissue is the heated fluid, rather than the electric current.

In an alternative embodiment, the active electrode(s) 104 are brought into contact with, or close proximity to, the target tissue so that the electric current passes directly into the tissue to a selected depth. In this embodiment, the return electrode draws the electric current away from the tissue site to limit its depth of penetration into the tissue. Applicant has discovered that the depth of current penetration also can be varied with the electrosurgical system of the present invention by changing the frequency of the voltage applied to the active electrode and the return electrode. This is because the electrical impedance of tissue is known to decrease with increasing frequency due to the electrical properties of cell membranes which surround electrically conductive cellular fluid. At lower frequencies (e.g., less than 350 kHz), the higher tissue impedance, the presence of the return electrode and the active electrode configuration of the present invention (discussed in detail below) cause the current flux lines to penetrate less deeply resulting in a smaller depth of tissue heating. In an exemplary embodiment, an operating frequency of about 100 kHz to 200 kHz is applied to the active electrode(s) to obtain shallow depths of collagen shrinkage (e.g., usually less than 1.5 mm and preferably less than 0.5 mm).

In another aspect of the invention, the size (e.g., diameter or principal dimension) of the active electrodes employed for treating the tissue are selected according to the intended depth of tissue treatment. As described previously in co-pending patent application PCT International Application, U.S. National Phase Ser. No. PCT/US94/05168, the depth of current penetration into tissue increases with increasing dimensions of an individual active electrode (assuming other factors remain constant, such as the frequency of the electric current, the return electrode configuration, etc.). The depth of current penetration (which refers to the depth at which the current density is sufficient to effect a change in the tissue, such as collagen shrinkage, irreversible necrosis, etc.) is on the order of the active electrode diameter for the bipolar configuration of the present invention and operating at a frequency of about 100 kHz to about 200 kHz. Accordingly, for applications requiring a smaller depth of current penetration, one or more active electrodes of smaller dimensions would be selected. Conversely, for applications requiring a greater depth of current penetration, one or more active electrodes of larger dimensions would be selected.

Figure 23:
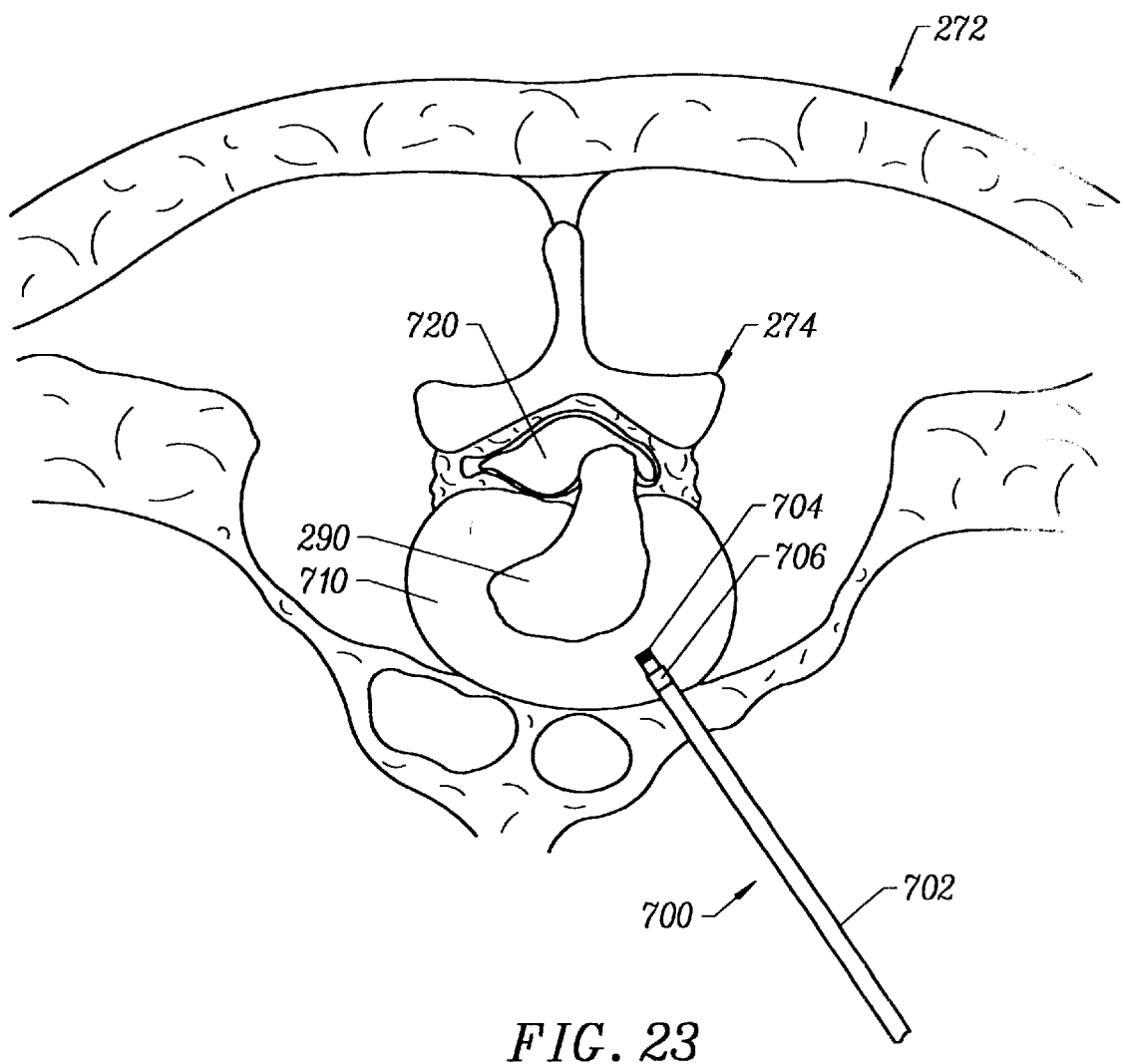
FIGS. 23–25 illustrates another method of treating a spinal disc with one of the catheters or probes of the present invention.
Figure 24:
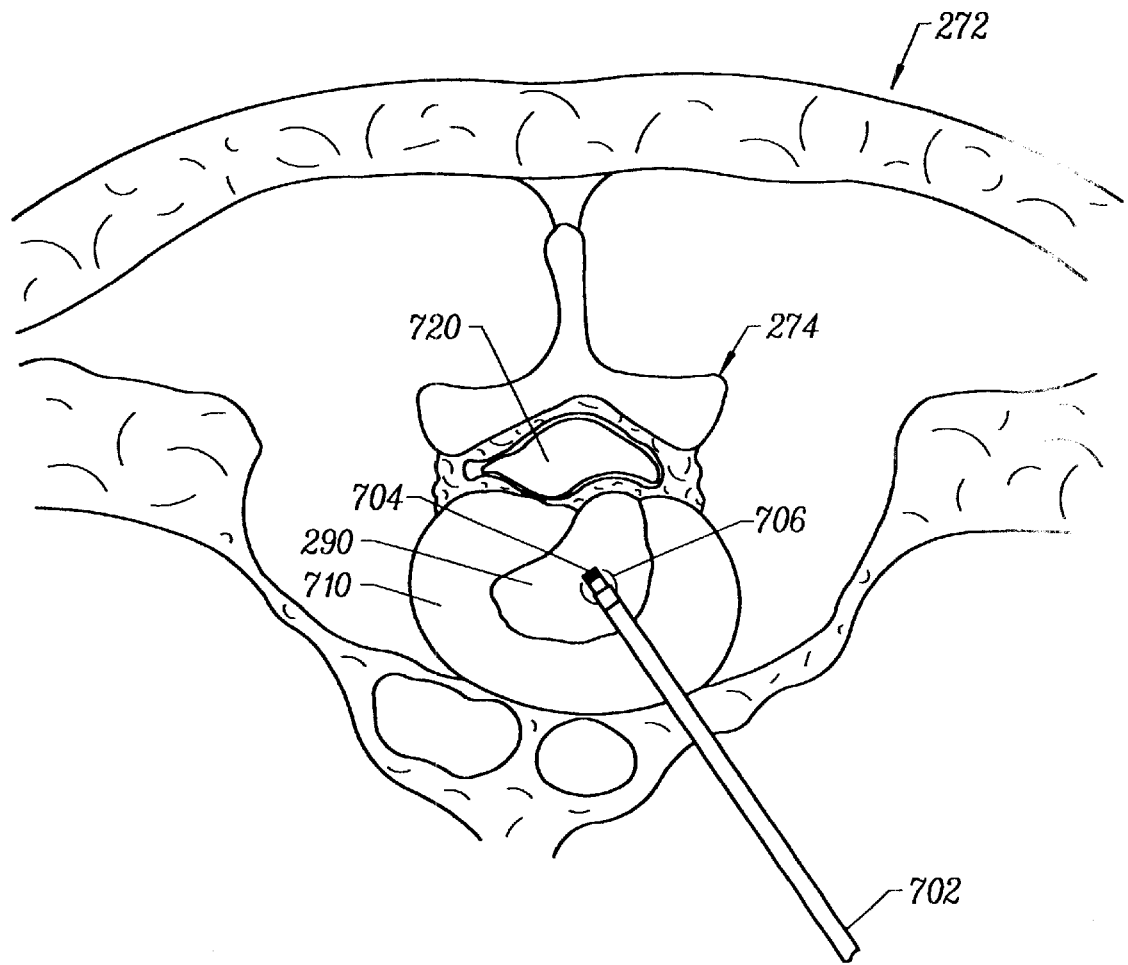
Figure 25:
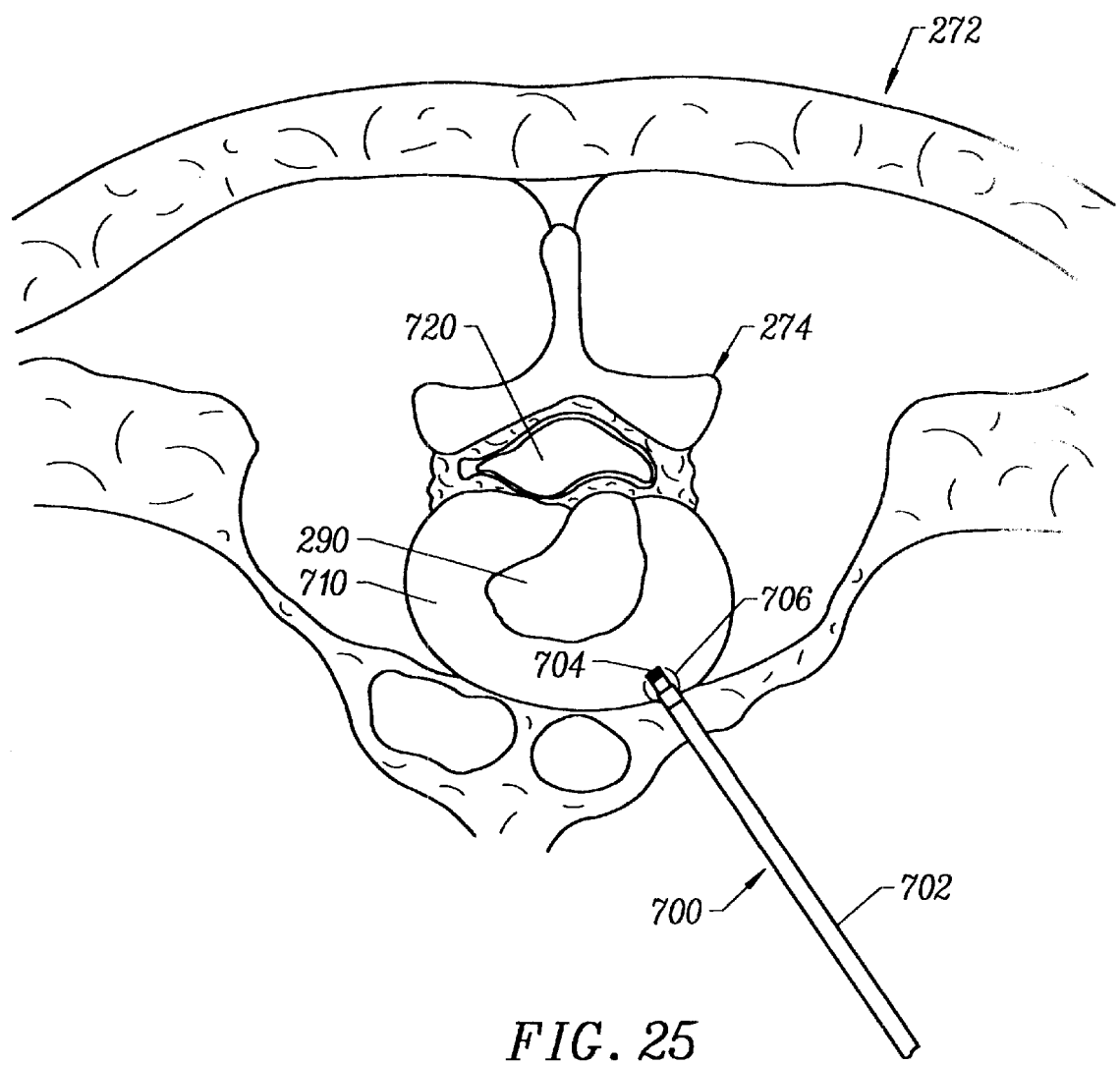

FIGS. 23–25 illustrate another system and method for treating swollen or herniated spinal discs according to the present invention. In this procedure, an electrosurgical probe 800 comprises a long, thin needle-like shaft 802 (e.g., on the order of about 1 mm in diameter or less) that can be percutaneously introduced posteriorly through the patient's back directly into the spine. The shaft 802 may or may not be flexible, depending on the method of access chosen by the physician. The probe shaft 802 will include one or more active electrode(s) 804 for applying electrical energy to tissues within the spine. The probe 800 may include one or more return electrode(s) 806, or the return electrode may be positioned on the patient's back, as a dispersive pad (not shown). As discussed below, however, a bipolar design is preferable.

As shown in FIG. 23, the distal portion of shaft 802 is introduced anteriorly through a small percutaneous penetration into the annulus fibrosus 292 of the target spinal disc. To facilitate this process, the distal end of shaft 802 may taper down to a sharper point (e.g., a needle), which can then be retracted to expose active electrode(s) 804. Alternatively, the electrodes may be formed around the surface of the tapered distal portion of shaft (not shown). In either embodiment, the distal end of shaft is delivered through the annulus 292 to the target nucleus pulposus 294, which may be herniated, extruded, non-extruded, or simply swollen. As shown in FIG. 24, high frequency voltage is applied between active electrode(s) 804 and return electrode(s) 806 to heat the surrounding collagen to suitable temperatures for contraction (i.e., typically about 55° C. to about 70° C.). As discussed above, this procedure may be accomplished with a monopolar configuration, as well. However, applicant has found that the bipolar configuration shown in FIGS. 23–25 provides enhanced control of the high frequency current, which reduces the risk of spinal nerve damage.

As shown in FIG. 24 and 25, once the nucleus pulposus 294 has been sufficiently contracted to retract from impingement on the nerve 720, the probe 800 is removed from the target site. In the representative embodiment, the high frequency voltage is applied between active and return electrode(s) 804, 806 as the probe is withdrawn through the annulus 292. This voltage is sufficient to cause contraction of the collagen fibers within the annulus 292, which allows the annulus 292 to contract around the hole formed by probe 800, thereby improving the healing of this hole. Thus, the probe 800 seals its own passage as it is withdrawn from the disc.

Figure 26A:
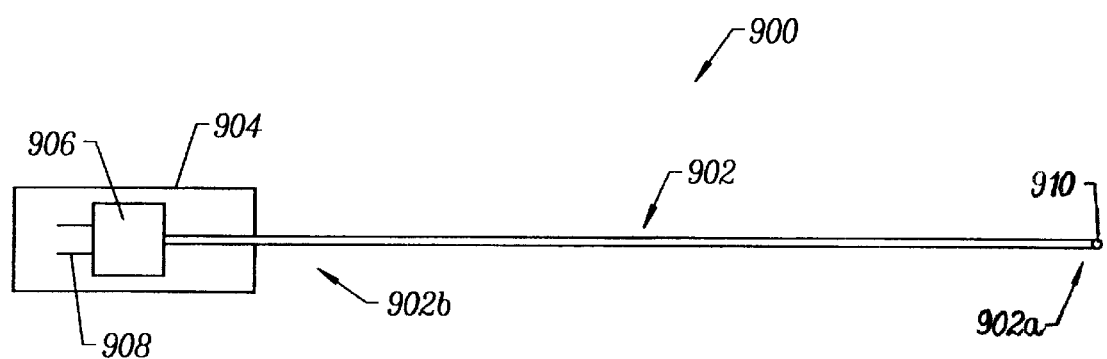
FIG. 26A is a side view of an electrosurgical probe according to the invention.

FIG. 26A is a side view of an electrosurgical probe 900, according to one embodiment of the invention. Probe 900 includes a shaft 902 having a distal end portion 902a and a proximal end portion 902b. An active electrode 910 is disposed on distal end portion 902a. Although only one active electrode is shown in FIG. 26A, embodiments including a plurality of active electrodes are also within the scope of the invention. Probe 900 further includes a handle 904 which houses a connection block 906 for coupling electrodes, e.g. active electrode 910, thereto. Connection block 906 includes a plurality of pins 908 adapted for coupling probe 900 to a power supply unit, e.g. power supply 28 (FIG. 1).

Figure 26B:
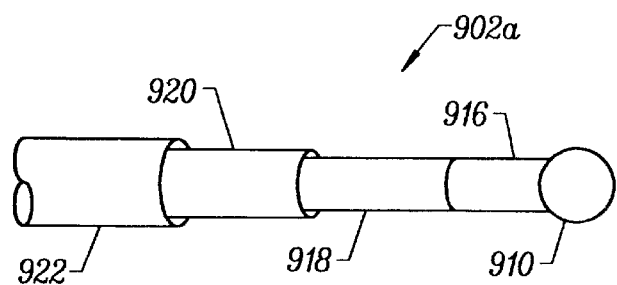
FIG. 26B is a side view of the distal end portion of the electrosurgical probe of FIG. 26A.
Figure 31A:
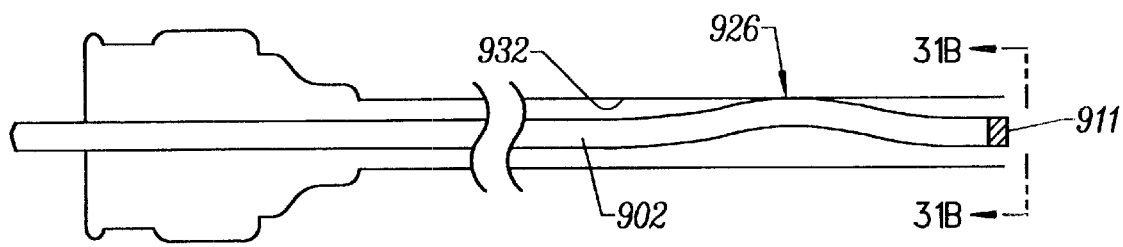
FIGS. 31A, 31B show a side view and an end view, respectively, of a curved shaft of an electrosurgical probe, in relation to an introducer needle.

FIG. 26B is a side view of the distal end portion of the electrosurgical probe of FIG. 26A, showing details of shaft distal end portion 902a. Distal end portion 902a includes an insulating collar or spacer 916 proximal to active electrode 910, and a return electrode 918 proximal to collar 916. A first insulating sleeve (FIG. 28B) may be located beneath return electrode 918. A second insulating jacket or sleeve 920 may extend proximally from return electrode 918. Second insulating sleeve 920 serves as an electrical insulator to inhibit current flow into the adjacent tissue. In a currently preferred embodiment, probe 900 further includes a shield 922 extending proximally from second insulating sleeve 920. Shield 922 may be formed from a conductive metal such as stainless steel, and the like. Shield 922 functions to decrease the amount of leakage current passing from probe 900 to a patient or a user (e.g., surgeon). In particular, shield 922 decreases the amount of capacitive coupling between return electrode 918 and an introducer needle 928 (FIG. 31A). Typically shield 922 is coupled to an outer floating conductive layer or cable shield (not shown) of a cable, e.g. cables 22, 34 (FIG. 1), connecting probe 900 to power supply 28. In this way, the capacitor balance of shaft 902 is disturbed. In one embodiment, shield 922 may be coated with a durable, hard compound such as titanium nitride. Such a coating has the advantage of providing reduced friction between shield 922 and introducer inner wall 932 as shaft 902 is axially translated within introducer needle 928 (e.g., FIGS. 31A, 31B).

Figure 27A:
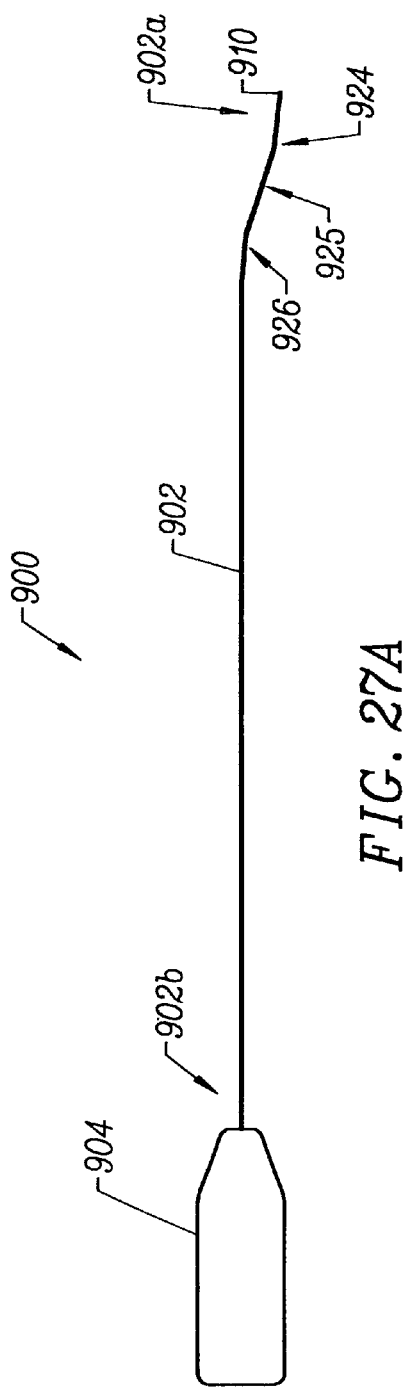
FIG. 27A is a side view of an electrosurgical probe having a curved shaft.

FIG. 27A is a side view of an electrosurgical probe 900 showing a first curve 924 and a second curve 926 located at distal end portion 902a, wherein second curve 926 is proximal to first curve 924. First curve 924 and second curve 926 may be separated by a linear (i.e. straight, or non-curved), or substantially linear, inter-curve portion 925 of shaft 902.

Figure 27B:
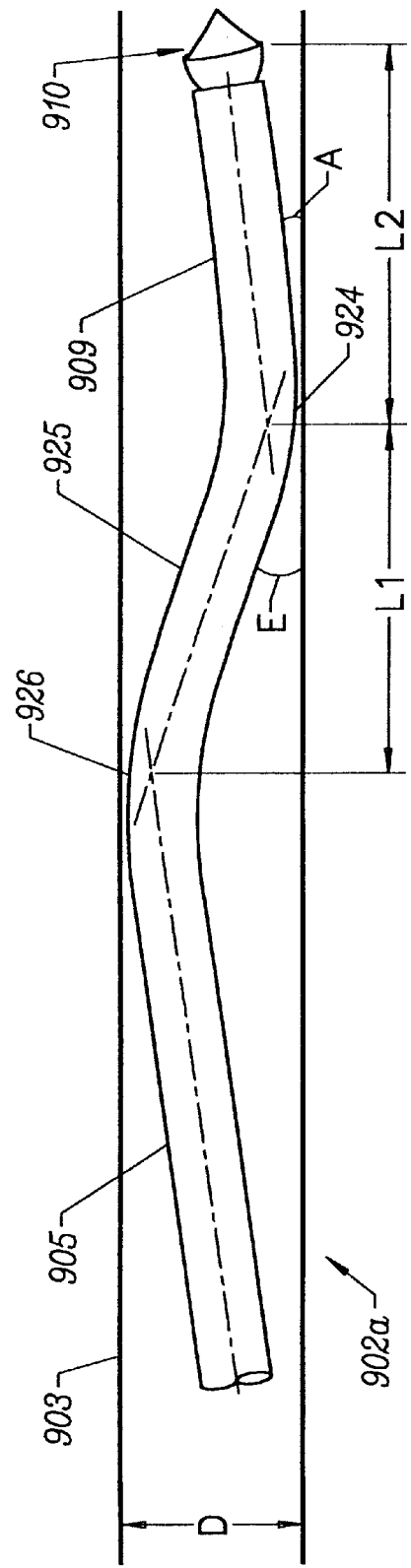
FIG. 27B is a side view of the distal end portion of the curved shaft of FIG. 27A, with the shaft distal end portion within an introducer device.

FIG. 27B is a side view of shaft distal end portion 902a within a representative introducer device or needle 928 having an inner diameter D. Shaft distal end portion 902a includes first curve 924 and second curve 926 separated by inter-curve portion 925. In one embodiment, shaft distal end portion 902a includes a linear or substantially linear proximal portion 901 extending from proximal end portion 902b to second curve 926, a linear or substantially linear inter-curve portion 925 between first and second curves 924, 926, and a linear or substantially linear distal portion 909 between first curve 924 and the distal tip of shaft 902 (the distal tip is represented in FIG. 27B as an electrode head 911). When shaft distal end portion 902a is located within introducer needle 928, first curve 924 subtends a first angle ∀ to the inner surface of needle 928, and second curve 926 subtends a second angle ∃ to inner surface 932 of needle 928. (In the situation shown in FIG. 27B, needle inner surface 932 is essentially parallel to the longitudinal axis of shaft proximal end portion 902b (FIG. 27A).) In one embodiment, shaft distal end portion 902a is designed such that the shaft distal tip occupies a substantially central transverse location within the lumen of introducer needle 928 when shaft distal end portion 902a is translated axially with respect to introducer needle 928. Thus, as shaft distal end portion 902a is advanced through the distal opening of needle 928 (FIGS. 30B, 31B), and then retracted back into the distal opening, the shaft distal tip will always occupy a transverse location towards the center of introducer needle 928 (even though the tip may be curved or biased away from the longitudinal axis of shaft 902 and needle 928 upon its advancement past the distal opening of introducer needle 928). In one embodiment, shaft distal end portion 902a is flexible and has a configuration which requires shaft distal end portion 902a be distorted in the region of at least second curve 926 by application of a lateral force imposed by inner wall 932 of introducer needle 928 as shaft distal end portion 902a is introduced or retracted into needle 928. In one embodiment, first curve 924 and second curve 926 are in the same plane relative to the longitudinal axis of shaft 902, and first and second curves 924, 926 are in opposite directions.

The "S-curve" configuration of shaft 902 shown in FIGS. 27A–C allows the distal end or tip of a device to be advanced or retracted through needle distal end 928a and within the lumen of needle 928 without the distal end or tip contacting introducer needle 928. Accordingly, this design allows a sensitive or delicate component to be located at the distal tip of a device, wherein the distal end or tip is advanced or retracted through a lumen of an introducer instrument comprising a relatively hard material (e.g., an introducer needle comprising stainless steel). This design also allows a component located at a distal end or tip of a device to be constructed from a relatively soft material, and for the component located at the distal end or tip to be passed through an introducer instrument comprising a hard material without risking damage to the component comprising a relatively soft material.

The "S-curve" design of shaft distal end portion 902a allows the distal tip (e.g., electrode head 911) to be advanced and retracted through the distal opening of needle 928 while avoiding contact between the distal tip and the edges of the distal opening of needle 928. (If, for example, shaft distal end portion 902a included only a single curve the distal tip would ordinarily come into contact with needle distal end 928a as shaft 902 is retracted into the lumen of needle 928.) In preferred embodiments, the length L2 of distal portion 909 and the angle ∀ between distal portion 909 and needle inner surface 932 928, when shaft distal end portion 902a is compressed within needle 928, are selected such that the distal tip is substantially in the center of the lumen of needle 928, as shown in FIG. 27B. Thus, as the length L2 increases, the angle ∀ will decrease, and vice versa. The exact values of length L2 and angle ∀ will depend on the inner diameter, D of needle 928, the inner diameter, d of shaft distal end portion 902a, and the size of the shaft distal tip.

The presence of first and second curves, 924, 926 provides a pre-defined bias in shaft 902. In addition, in one embodiment shaft distal end portion 902a is designed such that at least one of first and second curves 924, 926 are compressed to some extent as shaft distal end portion 902a is retracted into the lumen of needle 928. Accordingly, the angle of at least one of curves 924, 926 may be changed when distal end portion 902a is advanced out through the distal opening of introducer needle 928, as compared with the corresponding angle when shaft distal end portion is completely retracted within introducer needle 928. For example, FIG. 27C shows shaft 902 of FIG. 27B free from introducer needle 928, wherein first and second curves 924, 926 are allowed to adopt their natural or uncompressed angles ∀' and ∃', respectively, wherein ∃' is typically equal to or greater than ∃. Angle ∀' may be greater than, equal to, or less than angle ∀. Angle ∃' is subtended by inter-curve portion 925 and proximal portion 901. When shaft distal end portion 902a is unrestrained by introducer needle 928, proximal portion 901 approximates the longitudinal axis of shaft 902. Angle ∀' is subtended between linear distal portion 909 and a line drawn parallel to proximal portion 901. Electrode head 911 is omitted from FIG. 27C for the sake of clarity.

The principle described above with reference to shaft 902 and introducer needle 928 may equally apply to a range of other medical devices. That is to say, the "S-curve" configuration of the invention may be included as a feature of any medical system or apparatus in which a medical instrument may be axially translated or passed within an introducer device. In particular, the principle of the "S-curve" configuration of the invention may be applied to any apparatus wherein it is desired that the distal end of the medical instrument does not contact or impinge upon the introducer device as the medical instrument is advanced from or retracted into the introducer device. The introducer device may be any apparatus through which a medical instrument is passed. Such medical systems may include, for example, a catheter, a cannula, an endoscope, and the like.

When shaft 902 is advanced distally through the needle lumen to a point where second curve 926 is located distal to needle distal end 928a, the shaft distal tip is deflected from the longitudinal axis of needle 928. The amount of this deflection is determined by the relative size of angles ∃' and ∀', and the relative lengths of L1 and L2. The amount of this deflection will in turn determine the size of a channel or lesion (depending on the application) formed in a tissue treated by electrode head 911 when shaft 902 is rotated circumferentially with respect to the longitudinal axis of probe 900.

As a result of the pre-defined bias in shaft 902, shaft distal end portion 902a will contact a larger volume of tissue than a linear shaft having the same dimensions. In addition, in one embodiment the pre-defined bias of shaft 902 allows the physician to guide or steer the distal tip of shaft 902 by a combination of axial movement of needle distal end 928a and the inherent curvature at shaft distal end portion 902a of probe 900.

Shaft 902 preferably has a length in the range of from about 4 to 30 cm. In one aspect of the invention, probe 900 is manufactured in a range of sizes having different lengths and/or diameters of shaft 902. A shaft of appropriate size can then be selected by the surgeon according to the body structure or tissue to be treated and the age or size of the patient. In this way, patients varying in size from small children to large adults can be accommodated. Similarly, for a patient of a given size, a shaft of appropriate size can be selected by the surgeon depending on the organ or tissue to be treated, for example, whether an intervertebral disc to be treated is in the lumbar spine or the cervical spine. For example, a shaft suitable for treatment of a disc of the cervical spine may be substantially smaller than a shaft for treatment of a lumbar disc. For treatment of a lumbar disc in an adult, shaft 902 is preferably in the range of from about 15 to 25 cm. For treatment of a cervical disc, shaft 902 is preferably in the range of from about 4 to about 15 cm.

The diameter of shaft 902 is preferably in the range of from about 0.5 to about 2.5 mm, and more preferably from about 1 to 1.5 mm. First curve 924 is characterized by a length L1, while second curve 926 is characterized by a length L2 (FIG. 27B). Inter-curve portion 925 is characterized by a length L3, while shaft 902 extends distally from first curve 924 a length L4. In one embodiment, L2 is greater than L1. Length L1 may be in the range of from about 0.5 to about 5 mm, while L2 may be in the range of from about 1 to about 10 mm. Preferably, L3 and L4 are each in the range of from about 1 to 6 mm.

Figure 28A:
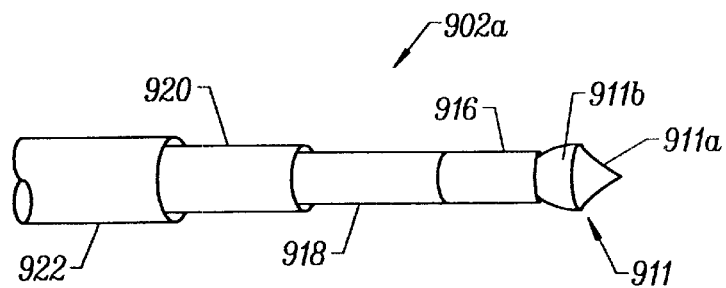
FIG. 28A is a side view of the distal end portion of an electrosurgical probe showing an active electrode having an apical spike and an equatorial cusp.

FIG. 28A is a side view of shaft distal end portion 902a of electrosurgical probe 900 showing a head 911 of active electrode 910 (the latter not shown in FIG. 28A), according to one embodiment of the invention. In this embodiment, electrode head 911 includes an apical spike 911a and an equatorial cusp 911b. Electrode head 911 exhibits a number of advantages as compared with, for example, an electrosurgical probe having a blunt, globular, or substantially spherical active electrode. In particular, electrode head 911 provides a high current density at apical spike 911a and cusp 911b. In turn, high current density in the vicinity of an active electrode is advantageous in the generation of a plasma; and, as is described fully hereinabove, generation of a plasma in the vicinity of an active electrode is fundamental to ablation of tissue with minimal collateral thermal damage according to certain embodiments of the instant invention. Electrode head 911 provides an additional advantage, in that the sharp edges of cusp 911b, and more particularly of apical spike 911a, facilitate movement and guiding of head 911 into tissue during surgical procedures, as described fully hereinbelow. In contrast, an electrosurgical probe having a blunt or rounded apical electrode is more likely to follow a path of least resistance, such as a channel which was previously ablated within nucleus pulposus tissue. Although certain embodiments of the invention depict head 911 as having a single apical spike, other shapes for the apical portion of active electrode 910 are also within the scope of the invention.

Figure 28B:
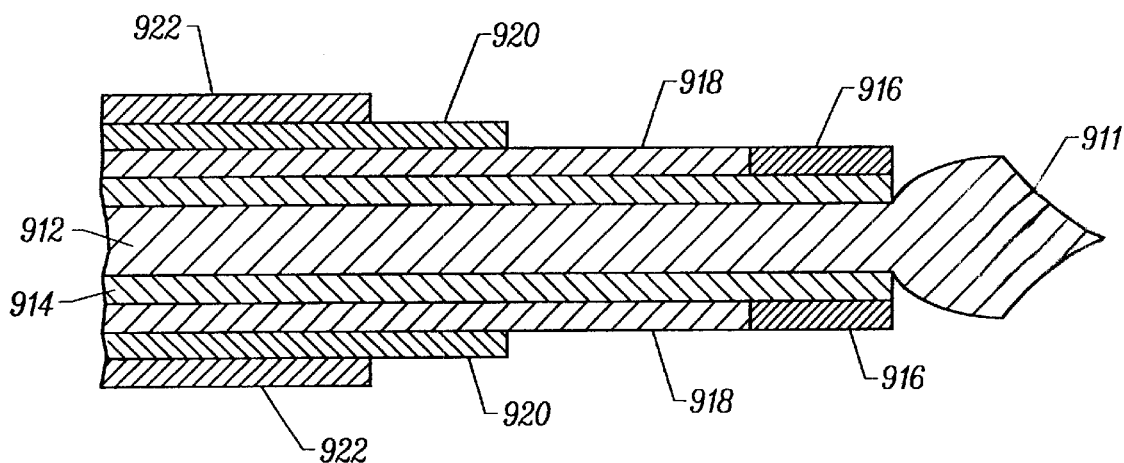
FIG. 28B is a cross-sectional view of the distal end portion of the electrosurgical probe of FIG. 28A.

FIG. 28B is a longitudinal cross-sectional view of distal end portion 902a of shaft 902. Apical electrode head 911 is in communication with a filament 912. Filament 912 typically comprises an electrically conductive wire encased within a first insulating sleeve 914. First insulating sleeve 914 comprises an insulator, such as various synthetic polymeric materials. An exemplary material from which first insulating sleeve 914 may be constructed is a polyimide. First insulating sleeve 914 may extend the entire length of shaft 902 proximal to head 911. An insulating collar or spacer 916 is disposed on the distal end of first insulating sleeve 914, adjacent to electrode head 911. Collar 916 preferably comprises a material such as a glass, a ceramic, or silicone. The exposed portion of first insulating sleeve 914 (i.e., the portion proximal to collar 916) is encased within a cylindrical return electrode 918. Return electrode 918 may extend proximally the entire length of shaft 902. Return electrode 918 may comprise an electrically conductive material such as stainless steel, tungsten, platinum or its alloys, titanium or its alloys, molybdenum or its alloys, nickel or its alloys, and the like. A proximal portion of return electrode 918 is encased within a second insulating sleeve 920, so as to provide an exposed band of return electrode 918 located distal to second sleeve 920 and proximal to collar 916. Second sleeve 920 provides an insulated portion of shaft 920 which facilitates handling of probe 900 by the surgeon during a surgical procedure. A proximal portion of second sleeve 920 is encased within an electrically conductive shield 922. Second sleeve 920 and shield 922 may also extend proximally for the entire length of shaft 902.

Figure 29:
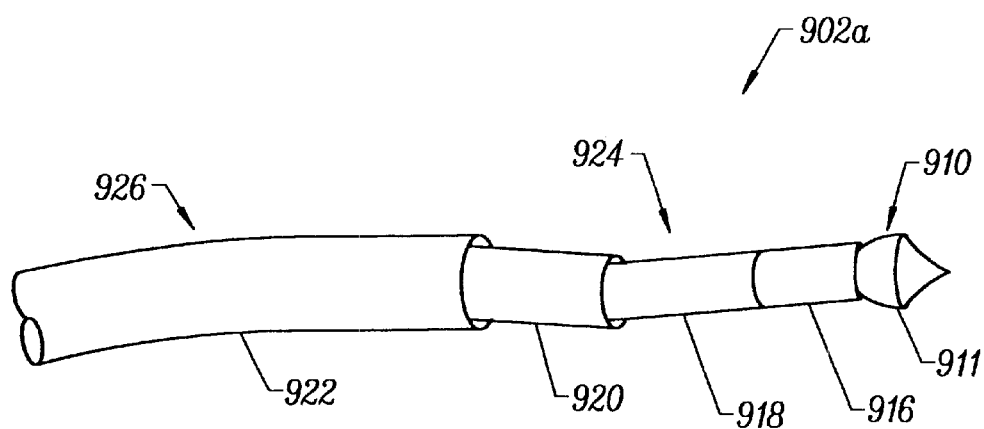
FIG. 29 is a side view of the distal end portion a shaft of an electrosurgical probe, indicating the position of a first curve and a second curve in relation to the head of the active electrode.

FIG. 29 is a side view of shaft distal end portion 902a of electrosurgical probe 900, indicating the position of first and second curves 924, 926, respectively. Probe 900 includes head 911, collar 916, return electrode 918, second insulating sleeve 920, and shield 922, generally as described with reference to FIGS. 28A, 28B. In the embodiment of FIG. 29, first curve 924 is located within return electrode 918, while second curve 926 is located within shield 922. However, according to various embodiments of the invention, shaft 902 may be provided in which one or more curves are present at alternative or additional locations or components of shaft 902, other than the location of first and second curves 924, 926, respectively, shown in FIG. 29.

Figure 30A:
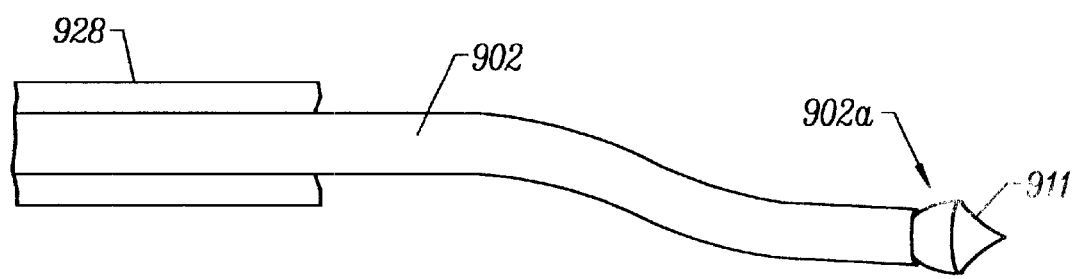
FIG. 30A shows the distal end portion of the shaft of an electrosurgical probe extended distally from an introducer needle.
Figure 30B:
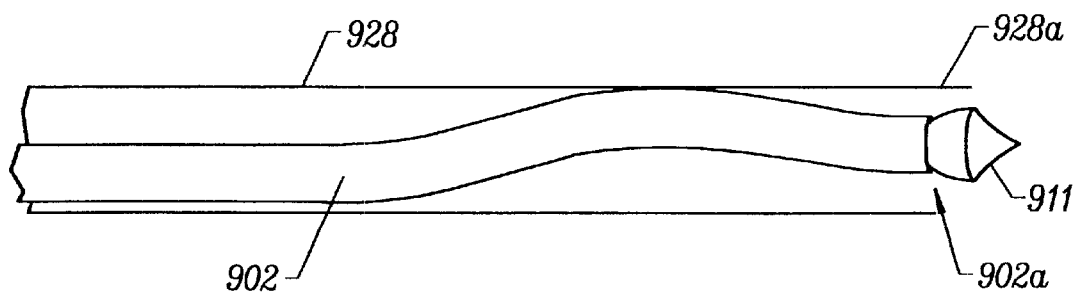
FIG. 30B illustrates the position of the active electrode in relation to the inner wall of the introducer needle upon retraction of the active electrode within the introducer needle.

FIG. 30A shows distal end portion 902a of shaft 902 extended distally from an introducer needle 928, according to one embodiment of the invention. Introducer needle 928 may be used to conveniently introduce shaft 902 into tissue, such as the nucleus pulposus of an intervertebral disc. In this embodiment, due to the curvature of shaft distal end 902a, when shaft 902 is extended distally beyond introducer needle 928, head 911 is displaced laterally from the longitudinal axis of introducer needle 928. However, as shown in FIG. 30B, as shaft 902 is retracted into introducer needle 928, head 911 assumes a substantially central transverse location within lumen 930 (see also FIG. 31B) of introducer 928. Such re-alignment of head 911 with the longitudinal axis of introducer 928 is achieved by specific design of the curvature of shaft distal end 902a, as accomplished by the instant inventors. In this manner, contact of various components of shaft distal end 902a (e.g., electrode head 911, collar 916, return electrode 918) is prevented, thereby not only facilitating extension and retraction of shaft 902 within introducer 928, but also avoiding a potential source of damage to sensitive components of shaft 902.

Figure 31B:
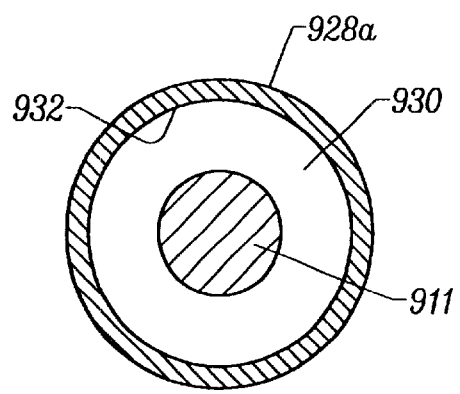

FIG. 31A shows a side view of shaft 902 in relation to an inner wall 932 of introducer needle 928 upon extension or retraction of electrode head 911 from, or within, introducer needle 928. Shaft 902 is located within introducer 928 with head 911 adjacent to introducer distal end 928a (FIG. 31B). Under these circumstances, curvature of shaft 902 may cause shaft distal end 902a to be forced into contact with introducer inner wall 932, e.g., at a location of second curve 926. Nevertheless, due to the overall curvature of shaft 902, and in particular the nature and position of first curve 924 (FIGS. 27A–B), head 911 does not contact introducer distal end 928a.

FIG. 31B shows an end view of electrode head 911 in relation to introducer needle 928 at a point during extension or retraction of shaft 902, wherein head 911 is adjacent to introducer distal end 928a (FIGS. 30B, 31B). In this situation, head 911 is substantially centrally positioned within lumen 930 of introducer 928. Therefore, contact between head 911 and introducer 928 is avoided, allowing shaft distal end 902a to be extended and retracted repeatedly without sustaining any damage to shaft 902.

Figure 32A:
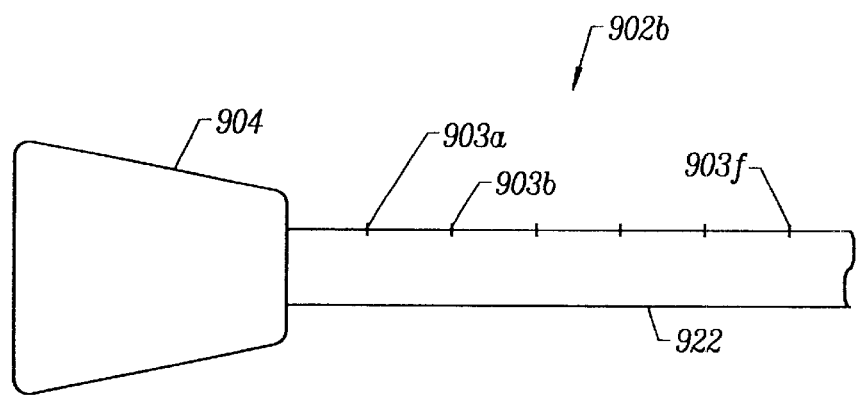
FIG. 32A shows the proximal end portion of the shaft of an electrosurgical probe, wherein the shaft includes a plurality of depth markings.

FIG. 32A shows shaft proximal end portion 902b of electrosurgical probe 900, wherein shaft 902 includes a plurality of depth markings 903 (shown as 903a–f in FIG. 32A). In other embodiments, other numbers and arrangements of depth markings 903 may be included on shaft 902. For example, in certain embodiments, depth markings may be present along the entire length of shield 922, or a single depth marking 903 may be present at shaft proximal end portion 902b. Depth markings serve to indicate to the surgeon the depth of penetration of shaft 902 into a patient's tissue, organ, or body, during a surgical procedure. Depth markings 903 may be formed directly in or on shield 922, and may comprise the same material as shield 922. Alternatively, depth markings 903 may be formed from a material other than that of shield 922. For example, depth markings may be formed from materials which have a different color and/or a different level of radiopacity, as compared with material of shield 922. For example, depth markings may comprise a metal, such as tungsten, gold, or platinum oxide (black), having a level of radiopacity different from that of shield 922. Such depth markings may be visualized by the surgeon during a procedure performed under fluoroscopy. In one embodiment, the length of the introducer needle and the shaft 902 are selected to limit the range of the shaft beyond the distal tip of the introducer needle.

Figure 32B:
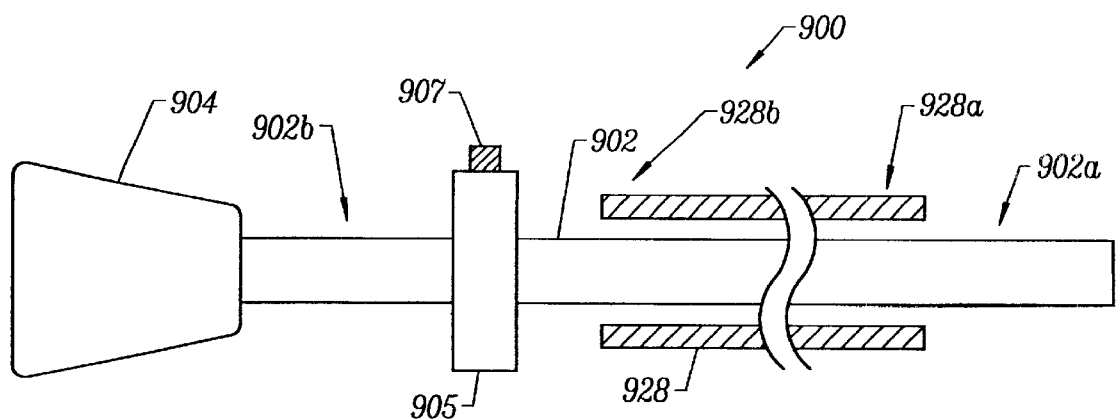
FIG. 32B shows the proximal end portion of the shaft of an electrosurgical probe, wherein the shaft includes a mechanical stop.

FIG. 32B shows a probe 900, wherein shaft 902 includes a mechanical stop 905. Preferably, mechanical stop 905 is located at shaft proximal end portion 902b. Mechanical stop 905 limits the distance to which shaft distal end 902a can be advanced through introducer 928 by making mechanical contact with a proximal end 928b of introducer 928. Mechanical stop 905 may be a rigid material or structure affixed to, or integral with, shaft 902. Mechanical stop 905 also serves to monitor the depth or distance of advancement of shaft distal end 902a through introducer 928, and the degree of penetration of distal end 902a into a patient's tissue, organ, or body. In one embodiment, mechanical stop 905 is movable on shaft 902, and stop 905 includes a stop adjustment unit 907 for adjusting the position of stop 905 and for locking stop 905 at a selected location on shaft 902.

Figure 33:
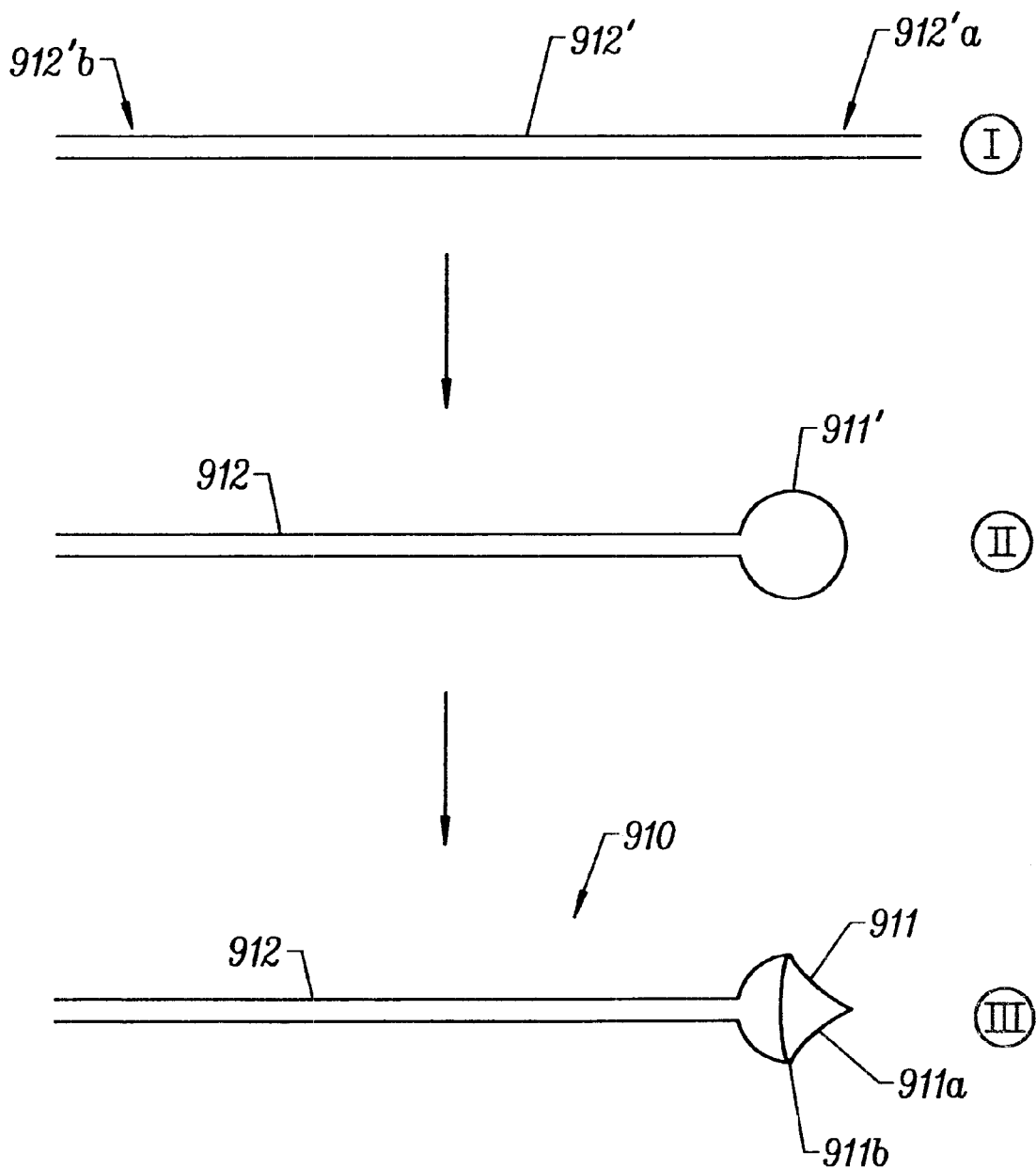
FIG. 33 illustrates stages in manufacture of an active electrode of an electrosurgical probe of the present invention.

FIG. 33 illustrates stages in manufacture of an active electrode 910 of a shaft 902, according to one embodiment of the present invention. Stage 33-I shows an elongated piece of electrically conductive material 912', e.g., a metal wire, as is well known in the art. Material 912' includes a first end 912'a and a second end 912'b. Stage 33-II shows the formation of a globular structure 911' from first end 912'a, wherein globular structure 911' is attached to filament 912. Globular structure 911' may be conveniently formed by applying heat to first end 912'a. Techniques for applying heat to the end of a metal wire are well known in the art. Stage 33-III shows the formation of an electrode head 911 from globular structure 911', wherein active electrode 910 comprises head 911 and filament 912 attached to head 911. In this particular embodiment, head 911 includes an apical spike 911a and a substantially equatorial cusp 911b.

Figure 34:
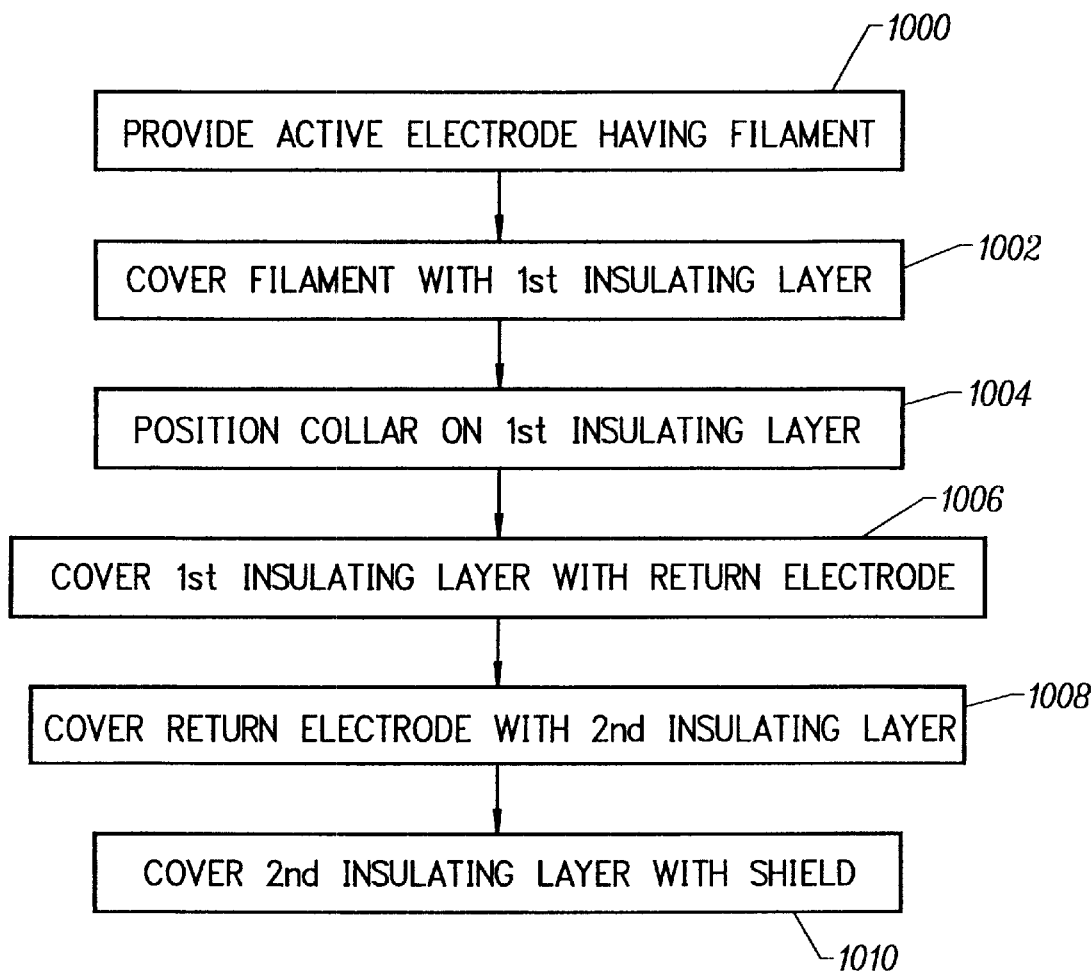
FIG. 34 schematically represents a series of steps involved in a method of making a probe shaft of the present invention.

FIG. 34 schematically represents a series of steps involved in a method of making a shaft according to one embodiment of the present invention, wherein step 1000 involves providing an active electrode having a filament, the active electrode including an electrode head attached to the filament. An exemplary active electrode to be provided in step 1000 is an electrode of the type described with reference to FIG. 33. At this stage (step 1000), the filament may be trimmed to an appropriate length for subsequent coupling to a connection block (FIG. 26A).

Step 1002 involves covering or encasing the filament with a first insulating sleeve of an electrically insulating material such as a synthetic polymer or plastic, e.g., a polyimide. Preferably, the first insulating sleeve extends the entire length of the shaft. Step 1004 involves positioning a collar of an electrically insulating material on the distal end of the first insulating sleeve, wherein the collar is located adjacent to the electrode head. The collar is preferably a material such as a glass, a ceramic, or silicone. Step 1006 involves placing a cylindrical return electrode over the first insulating sleeve. Preferably, the return electrode is positioned such that its distal end is contiguous with the proximal end of the collar, and the return electrode preferably extends proximally for the entire length of the shaft. The return electrode may be constructed from stainless steel or other non-corrosive, electrically conductive metal.

According to one embodiment, a metal cylindrical return electrode is prebent to include a curve within its distal region (i.e. the return electrode component is bent prior to assembly onto the shaft). As a result, the shaft assumes a first curve upon placing the return electrode over the first insulating sleeve, i.e. the first curve in the shaft results from the bend in the return electrode. Step 1008 involves covering a portion of the return electrode with a second insulating layer or sleeve such that a band of the return electrode is exposed distal to the distal end of the second insulating sleeve. In one embodiment, the second insulating sleeve comprises a heat-shrink plastic material which is heated prior to positioning the second insulating sleeve over the return electrode. According to one embodiment, the second insulating sleeve is initially placed over the entire length of the shaft, and thereafter the distal end of the second insulating sleeve is cut back to expose an appropriate length of the return electrode. Step 1010 involves encasing a proximal portion of the second insulating sleeve within a shield of electrically conductive material, such as a cylinder of stainless steel or other metal, as previously described herein.

Figure 35:
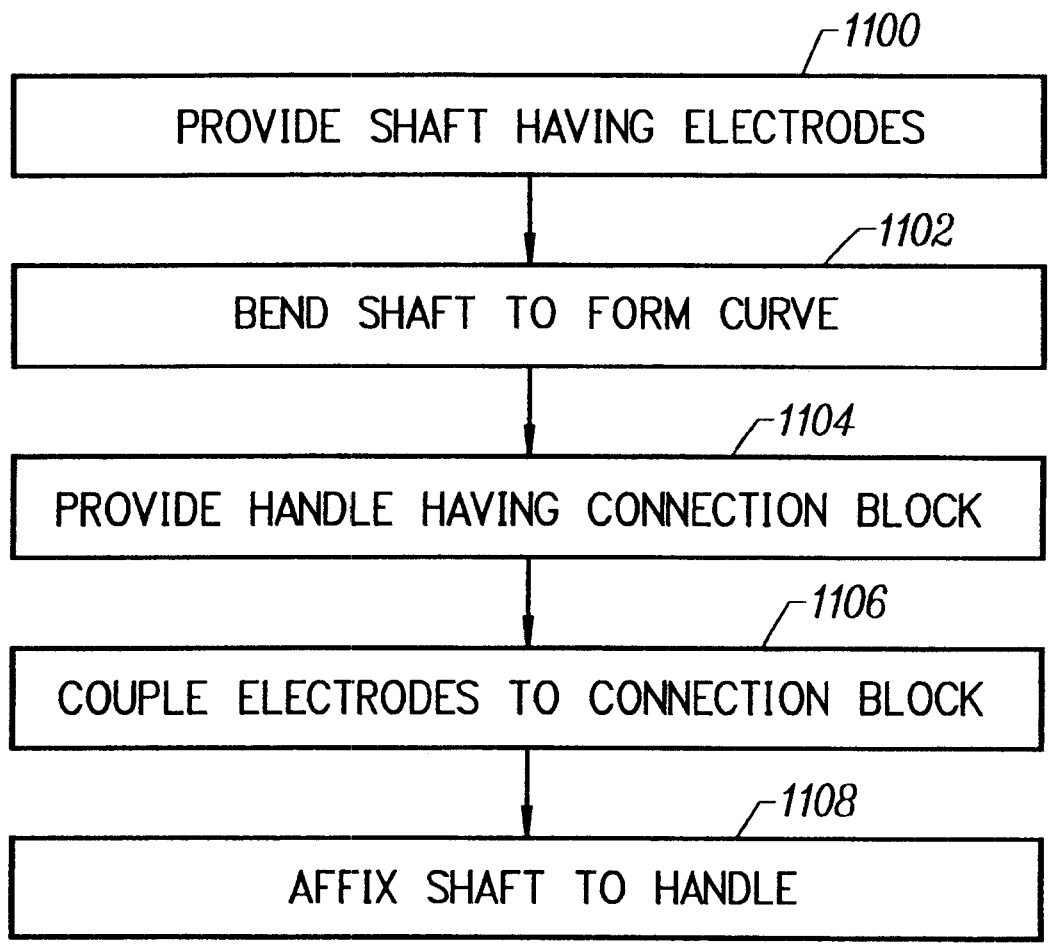
FIG. 35 schematically represents a series of steps involved in a method of making an electrosurgical probe of the present invention.

FIG. 35 schematically represents a series of steps involved in a method of making an electrosurgical probe of the present invention, wherein step 1100 involves providing a shaft having at least one active electrode and at least one return electrode. An exemplary shaft to be provided in step 1100 is that prepared according to the method described hereinabove with reference to FIG. 34, i.e., the shaft includes a first curve. Step 1102 involves bending the shaft to form a second curve. Preferably, the second curve is located at the distal end portion of the shaft, but proximal to the first curve. In one embodiment, the second curve is greater than the first curve. (Features of both the first curve and second curve have been described hereinabove, e.g., with reference to FIG. 27B.) Step 1104 involves providing a handle for the probe. The handle includes a connection block for electrically coupling the electrodes thereto. Step 1106 involves coupling the active and return electrodes of the shaft to the connection block. The connection block allows for convenient coupling of the electrosurgical probe to a power supply (e.g., power supply 28, FIG. 1). Thereafter, step 1108 involves affixing the shaft to the handle.

Figure 36A:
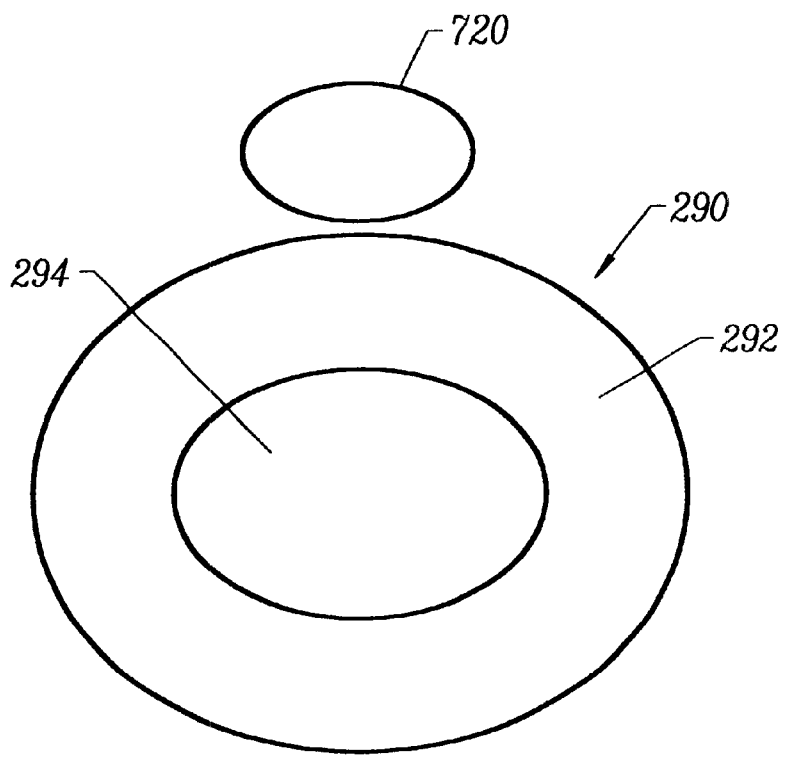
FIG. 36A schematically represents a normal intervertebral disc in relation to the spinal cord.
Figure 36B:
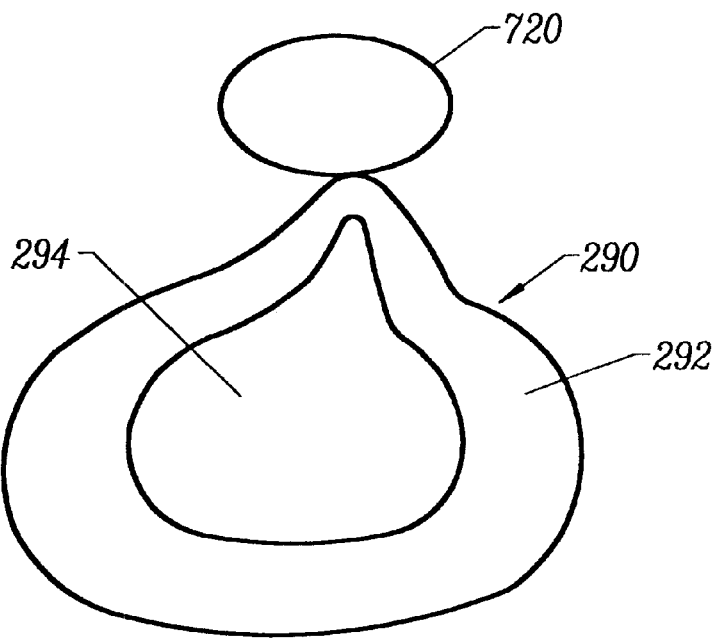
FIG. 36B schematically represents an intervertebral disc exhibiting a protrusion of the nucleus pulposus and a concomitant distortion of the annulus fibrosus.
Figure 36C:
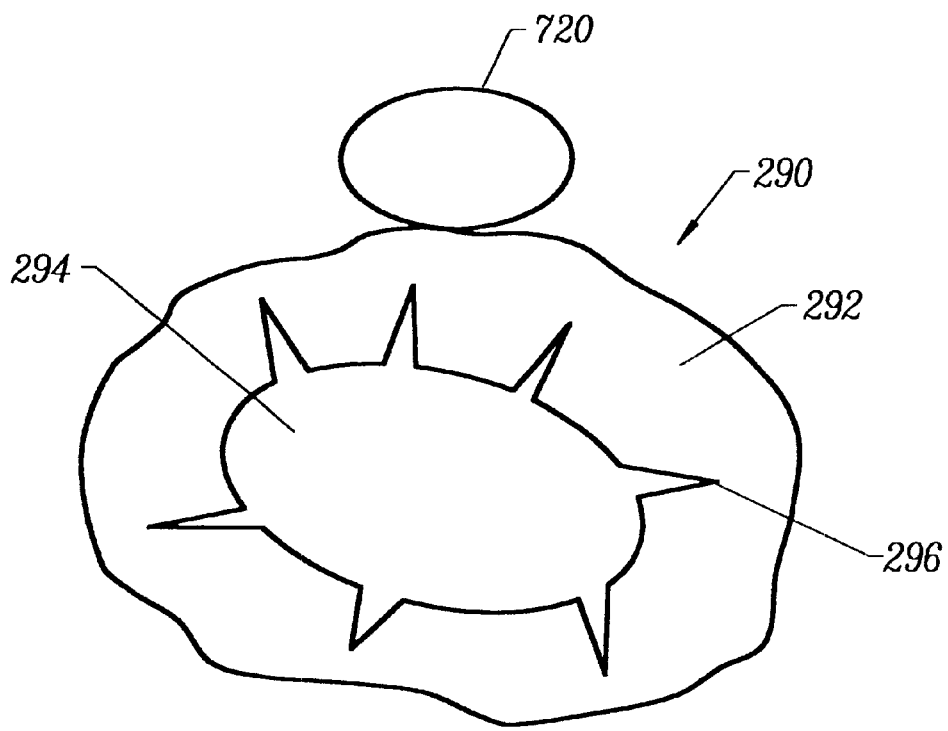
FIG. 36C schematically represents an intervertebral disc exhibiting a plurality of fissures within the annulus fibrosus and a concomitant distortion of the annulus fibrosus.
Figure 36D:
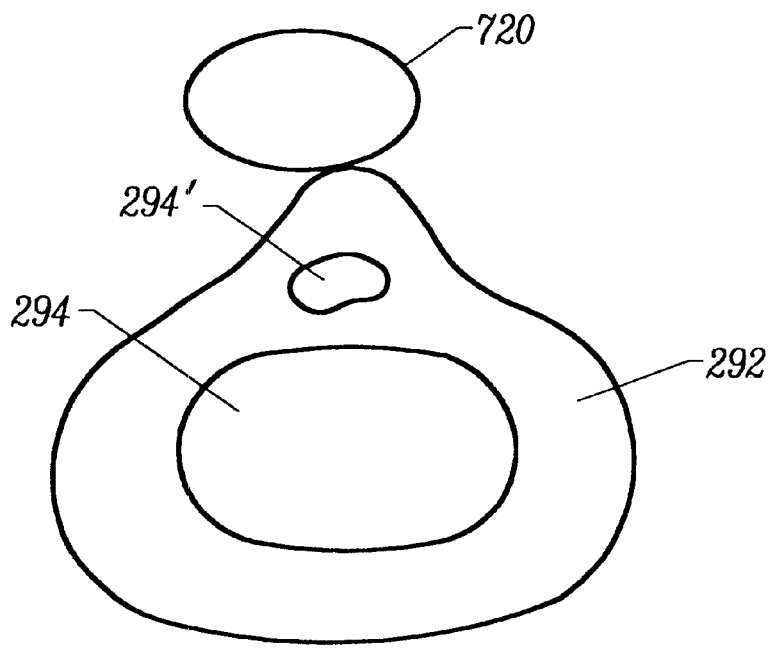
FIG. 36D schematically represents an intervertebral disc exhibiting fragmentation of the nucleus pulposus and a concomitant distortion of the annulus fibrosus.

FIG. 36A schematically represents a normal intervertebral disc 290 in relation to the spinal cord 720, the intervertebral disc having an outer annulus fibrosus 292 enclosing an inner nucleus pulposus 294. The nucleus pulposus is a relatively soft tissue comprising proteins and having a relatively high water content, as compared with the harder, more fibrous annulus fibrosus. FIGS. 36B–D each schematically represent an intervertebral disc having a disorder which can lead to discogenic pain, for example due to compression of a nerve root by a distorted annulus fibrosus. Thus, FIG. 36B schematically represents an intervertebral disc exhibiting a protrusion of the nucleus pulposus and a concomitant distortion of the annulus fibrosus. The condition depicted in FIG. 36B clearly represents a contained herniation, which can result in severe and often debilitating pain. FIG. 36C schematically represents an intervertebral disc exhibiting a plurality of fissures within the annulus fibrosus, again with concomitant distortion of the annulus fibrosus. Such annular fissures may be caused by excessive pressure exerted by the nucleus pulposus on the annulus fibrosus. Excessive pressure within the nucleus pulposus tends to intensify disc disorders associated with the presence of such fissures. FIG. 36D schematically represents an intervertebral disc exhibiting fragmentation of the nucleus pulposus and a concomitant distortion of the annulus fibrosus. In this situation, over time, errant fragment 294' of the nucleus pulposus tends to dehydrate and to diminish in size, often leading to a decrease in discogenic pain over an extended period of time (e.g., several months). For the sake of clarity, each FIG. 36B, 36C, 36D shows a single disorder. However, in practice more than one of the depicted disorders may occur in the same disc.

Many patients suffer from discogenic pain resulting, for example, from conditions of the type depicted in FIGS. 36B–D. However, only a small percentage of such patients undergo laminotomy or discectomy. Presently, there is a need for interventional treatment for the large group of patients who ultimately do not undergo major spinal surgery, but who sustain significant disability due to various disorders or abnormalities of an intervertebral disc. A common disorder of intervertebral discs is a contained herniation in which the nucleus pulposus does not breach the annulus fibrosus, but a protrusion of the disc causes compression of the exiting nerve root, leading to radicular pain. Typical symptoms are leg pain compatible with sciatica. Such radicular pain may be considered as a particular form of discogenic pain. Most commonly, contained herniations leading to radicular pain are associated with the lumbar spine, and in particular with intervertebral discs at either L4–5 or L5–S1. Various disc abnormalities are also encountered in the cervical spine. Methods and apparatus of the invention are applicable to all segments of the spine, including the cervical spine and the lumbar spine.

Figure 37:
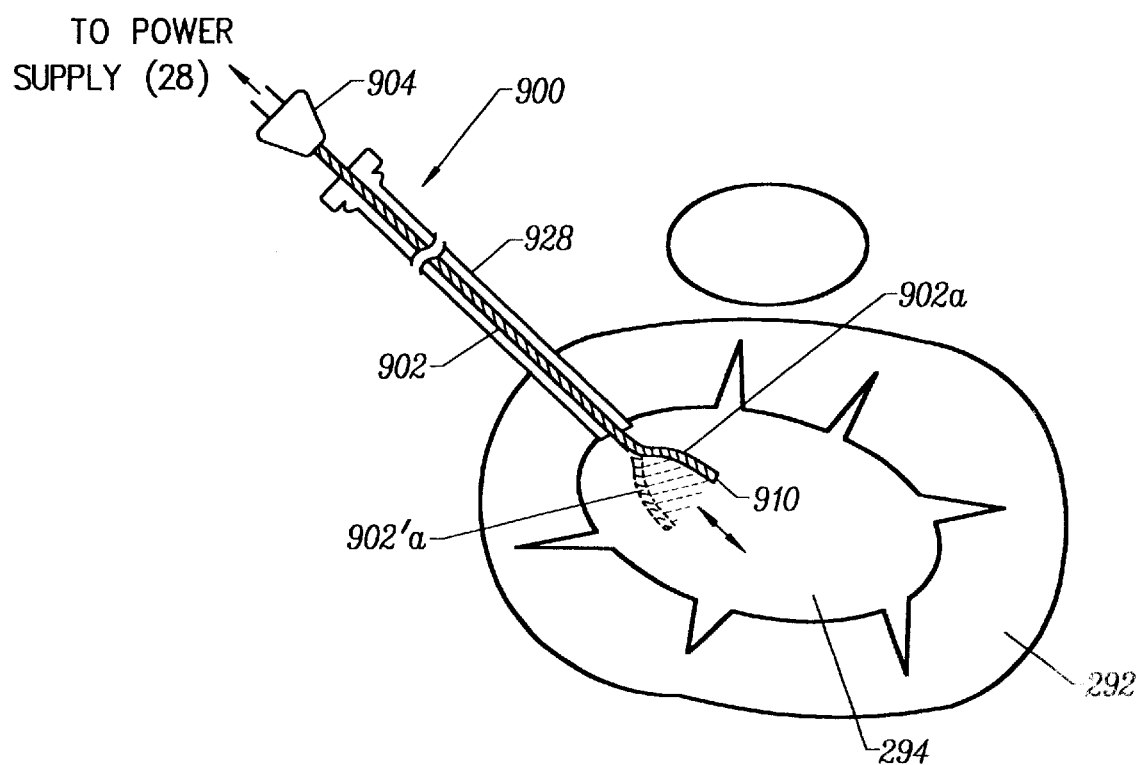
FIG. 37 schematically represents translation of a curved shaft of an electrosurgical probe within the nucleus pulposus for treatment of an intervertebral disc.

FIG. 37 schematically represents shaft 902 of probe 900 inserted within a nucleus pulposus of a disc having at least one fissure in the annulus. Shaft 902 may be conveniently inserted within the nucleus pulposus via introducer needle 928 in a minimally invasive percutaneous procedure. In a preferred embodiment, a disc in the lumbar spine may be accessed via a posterior lateral approach, although other approaches are possible and are within the scope of the invention. The preferred length and diameter of shaft 902 and introducer needle 928 to be used in a procedure will depend on a number of factors, including the region of the spine (e.g., lumbar, cervical) or other body region to be treated, and the size of the patient. Preferred ranges for shaft 902 are given elsewhere herein. In one embodiment for treatment of a lumbar disc, introducer needle 928 preferably has a diameter in the range of from about 50% to 150% the inside diameter of a 17 Gauge needle. In an embodiment for treatment of a cervical disc, introducer needle 928 preferably has a diameter in the range of from about 50% to 150% the inner diameter of a 20 Gauge needle.

Shaft 902 includes an active electrode 910, as described hereinabove. Shaft 902 features curvature at distal end 902a/902'a, for example, as described with reference to FIGS. 27A–B. By rotating shaft 902 through approximately 180°, shaft distal end 902a can be moved to a position indicated by the dashed lines and labeled as 902'a. Thereafter, rotation of shaft 902 through an additional 180° defines a substantially cylindrical three-dimensional space with a proximal conical area represented as a hatched area (shown between 902a and 902'a). The bidirectional arrow distal to active electrode 910 indicates translation of shaft 902 substantially along the longitudinal axis of shaft 902. By a combination of axial and rotational movement of shaft 902, a much larger volume of the nucleus pulposus can be contacted by electrode 910, as compared with a corresponding probe having a linear (non-curved) shaft. Furthermore, the curved nature of shaft 902 allows the surgeon to change the direction of advancement of shaft 902 by appropriate rotation thereof, and to guide shaft distal end 902a to a particular target site within the nucleus pulposus.

It is to be understood that according to certain embodiments of the invention, the curvature of shaft 902 is the same, or substantially the same, both prior to it being used in a surgical procedure and while it is performing ablation during a procedure, e.g., within an intervertebral disc. (One apparent exception to this statement, relates to the stage in a procedure wherein shaft 902 may be transiently "molded" into a somewhat more linear configuration by the constraints of introducer inner wall 932 during housing, or passing, of shaft 902 within introducer 928.) In contrast, certain prior art devices, and embodiments of the invention to be described hereinbelow (e.g., with reference to FIG. 43A, 43B), may be linear or lacking a naturally defined configuration prior to use, and then be steered into a selected configuration during a surgical procedure.

While shaft distal end 902a is at or adjacent to a target site within the nucleus pulposus, probe 900 may be used to ablate tissue by application of a first high frequency voltage between active electrode 910 and return electrode 918 (e.g., FIG. 26B), wherein the volume of the nucleus pulposus is decreased, the pressure exerted by the nucleus pulposus on the annulus fibrosus is decreased, and at least one nerve or nerve root is decompressed. Accordingly, discogenic pain experienced by the patient may be alleviated. Preferably, application of the first high frequency voltage results in formation of a plasma in the vicinity of active electrode 910, and the plasma causes ablation by breaking down high molecular weight disc tissue components (e.g., proteins) into low molecular weight gaseous materials. Such low molecular weight gaseous materials may be at least partially vented or exhausted from the disc, e.g., by piston action, upon removal of shaft 902 and introducer 928 from the disc and the clearance between the introducer 928 and the shaft 902. In addition, by-products of tissue ablation may be removed by an aspiration device (not shown in FIG. 37), as is well known in the art. In this manner, the volume and/or mass of the nucleus pulposus may be decreased.

Figure 41:
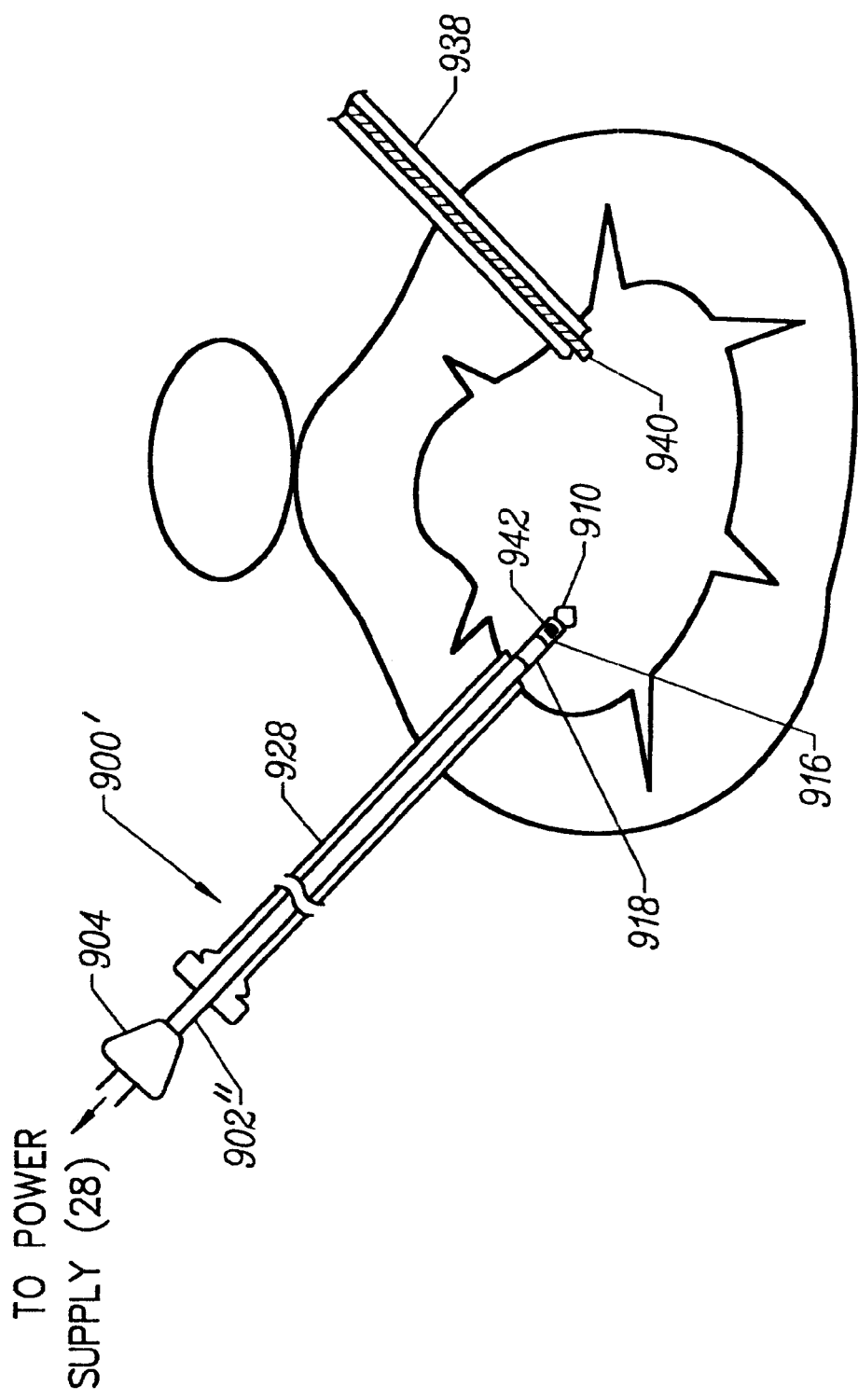
FIG. 41 shows treatment of an intervertebral disc using an electrosurgical probe and a separately introduced ancillary device, according to another embodiment of the invention.

In order to initiate and/or maintain a plasma in the vicinity of active electrode 910, a quantity of an electrically conductive fluid may be applied to shaft 902 and/or the tissue to ablated. The electrically conductive fluid may be applied to shaft 902 and/or to the tissue to be ablated, either before or during application of the first high frequency voltage. Examples of electrically conductive fluids are saline (e.g., isotonic saline), and an electrically conductive gel. An electrically conductive fluid may be applied to the tissue to be ablated before or during ablation. A fluid delivery unit or device may be a component of the electrosurgical probe itself, or may comprise a separate device, e.g., ancillary device 940 (FIG. 41). Alternatively, many body fluids and/or tissues (e.g., the nucleus pulposus, blood) at the site to be ablated are electrically conductive and can participate in initiation or maintenance of a plasma in the vicinity of the active electrode.

In one embodiment, after ablation of nucleus pulposus tissue by the application of the first high frequency voltage and formation of a cavity or channel within the nucleus pulposus, a second high frequency voltage may be applied between active electrode 910 and return electrode 918, wherein application of the second high frequency voltage causes coagulation of nucleus pulposus tissue adjacent to the cavity or channel. Such coagulation of nucleus pulposus tissue may lead to increased stiffness, strength, and/or rigidity within certain regions of the nucleus pulposus, concomitant with an alleviation of discogenic pain. Furthermore, coagulation of tissues may lead to necrotic tissue which is subsequently broken down as part of a natural bodily process and expelled from the body, thereby resulting in de-bulking of the disc. Although FIG. 37 depicts a disc having fissures within the annulus fibrosus, it is to be understood that apparatus and methods of the invention discussed with reference to FIG. 37 are also applicable to treating other types of disc disorders, including those described with reference to FIGS. 36B, 36D.

Figure 38:
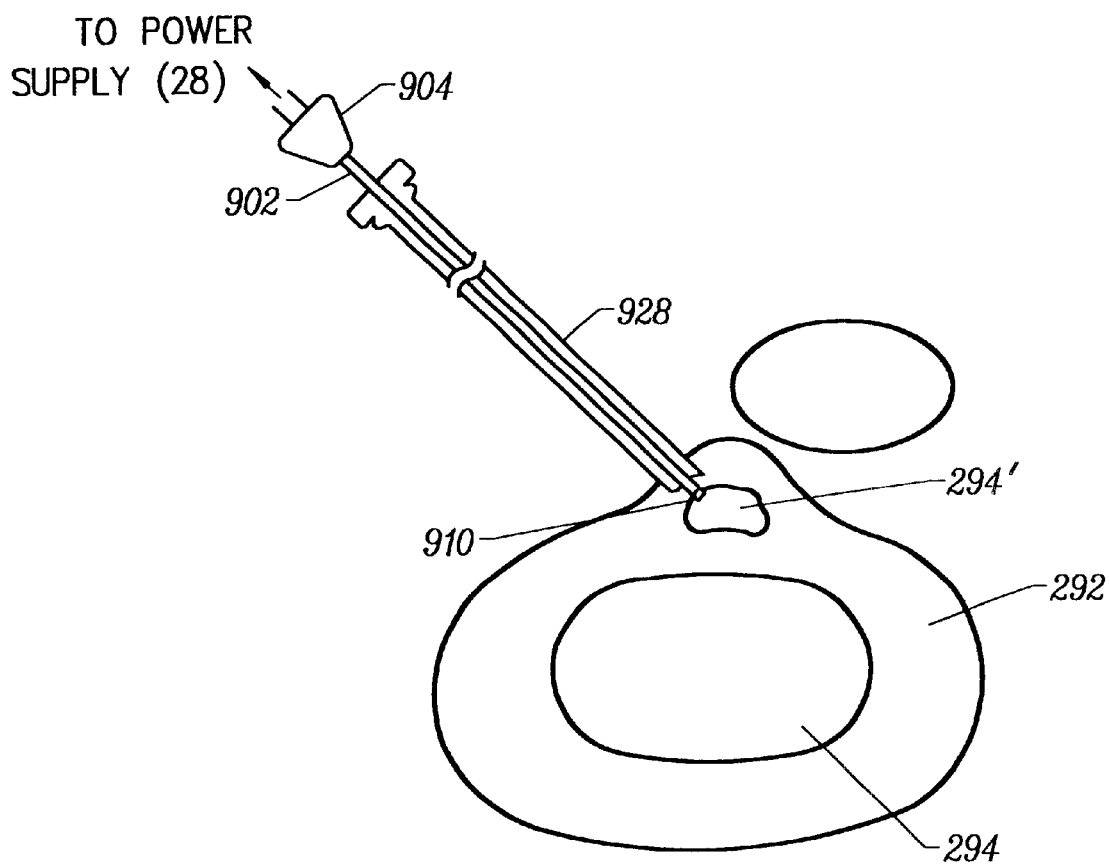
FIG. 38 shows a shaft of an electrosurgical probe within an intervertebral disc, wherein the shaft distal end is targeted to a specific site within the disc.

FIG. 38 shows shaft 902 of electrosurgical probe 900 within an intervertebral disc, wherein shaft distal end 902a is targeted to a specific site within the disc. In the situation depicted in FIG. 38, the target site is occupied by an errant fragment 294' of nucleus pulposus tissue. Shaft distal end 902 may be guided or directed, at least in part, by appropriate placement of introducer 928, such that active electrode 910 is in the vicinity of fragment 294'. Preferably, active electrode 910 is adjacent to, or in contact with, fragment 294'. Although FIG. 38 depicts a disc in which a fragment of nucleus pulposus is targeted by shaft 902, the invention described with reference to FIG. 38 may also be used for targeting other aberrant structures within an intervertebral disc, including annular fissures and contained herniations. In a currently preferred embodiment, shaft 902 includes at least one curve (not shown in FIG. 38), and other features described herein with reference to FIGS. 26A–35, wherein shaft distal end 902a may be precisely guided by an appropriate combination of axial and rotational movement of shaft 902. The procedure illustrated in FIG. 38 may be performed generally according to the description presented with reference to FIG. 37. That is, shaft 902 is introduced into the disc via introducer 928 in a percutaneous procedure. After shaft distal end 902a has been guided to a target site, tissue at or adjacent to that site is ablated by application of a first high frequency voltage. Thereafter, depending on the particular condition of the disc being treated, a second high frequency voltage may optionally be applied in order to locally coagulate tissue within the disc.

Figure 39:
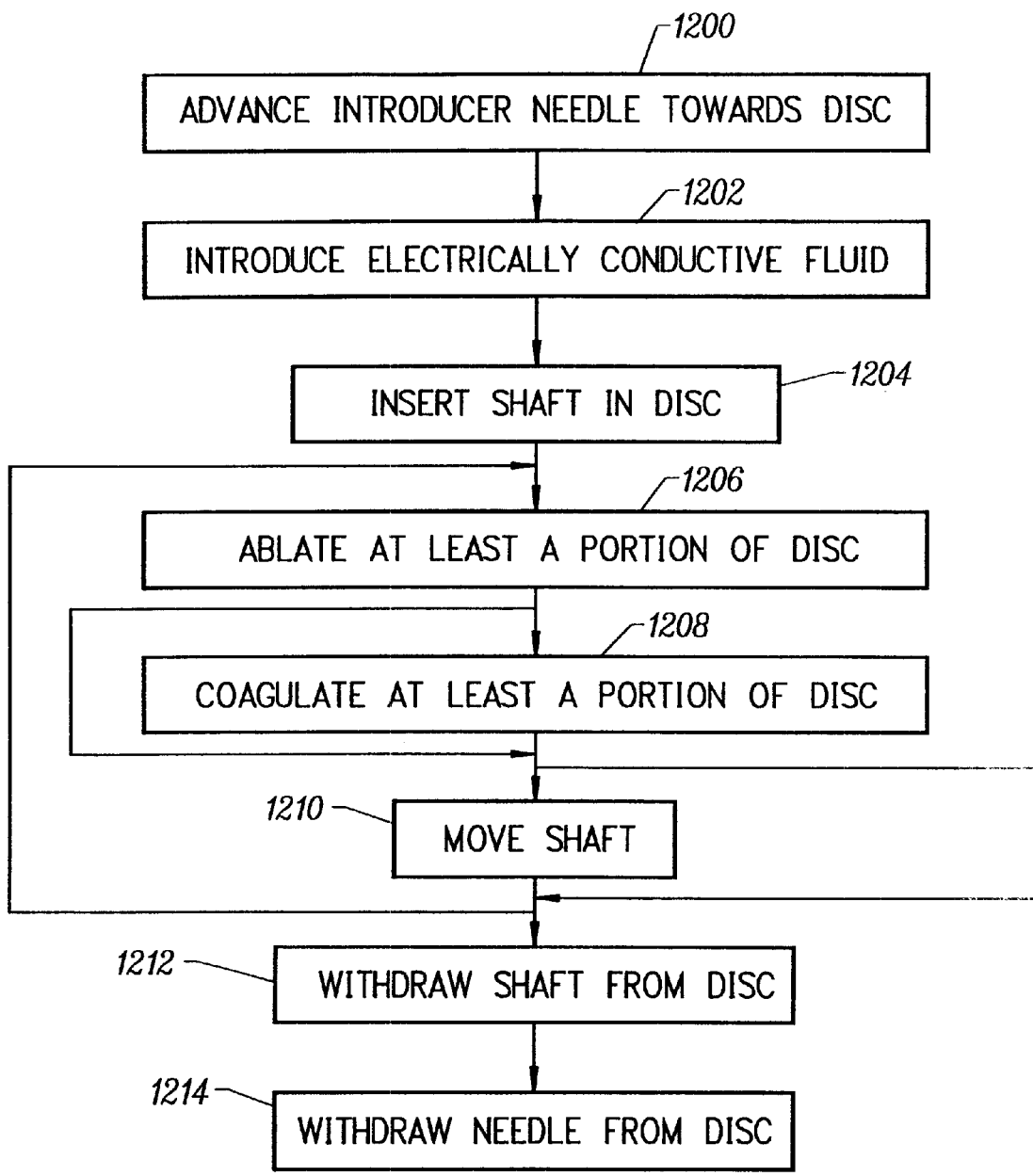
FIG. 39 schematically represents a series of steps involved in a method of ablating disc tissue according to the present invention.

FIG. 39 schematically represents a series of steps involved in a method of ablating disc tissue according to the present invention; wherein step 1200 involves advancing an introducer needle towards an intervertebral disc to be treated. The introducer needle has a lumen having a diameter greater than the diameter of the shaft distal end, thereby allowing free passage of the shaft distal end through the lumen of the introducer needle. In one embodiment, the introducer needle preferably has a length in the range of from about 3 cm to about 25 cm, and the lumen of the introducer needle preferably has a diameter in the range of from about 0.5 cm. to about 2.5 mm. Preferably, the lumen of the introducer needle has a diameter in the range of from about 105% to about 500% of the diameter of the shaft distal end. The introducer needle may be inserted in the intervertebral disc percutaneously, e.g. via a posterior lateral approach. In one embodiment, the introducer needle may have dimensions similar to those of an epidural needle, the latter well known in the art.

Optional step 1202 involves introducing an electrically conductive fluid, such as saline, into the disc. In one embodiment, in lieu of step 1202, the ablation procedure may rely on the electrical conductivity of the nucleus pulposus itself. Step 1204 involves inserting the shaft of the electrosurgical probe into the disc, e.g., via the introducer needle, wherein the distal end portion of the shaft bears an active electrode and a return electrode. In one embodiment, the shaft includes an outer shield, first and second curves at the distal end portion of the shaft, and an electrode head having an apical spike, generally as described with reference to FIGS. 26A–32.

Step 1206 involves ablating at least a portion of disc tissue by application of a first high frequency voltage between the active electrode and the return electrode. In particular, ablation of nucleus pulposus tissue according to methods of the invention serves to decrease the volume of the nucleus pulposus, thereby relieving pressure exerted on the annulus fibrosus, with concomitant decompression of a previously compressed nerve root, and alleviation of discogenic pain.

In one embodiment, the introducer needle is advanced towards the intervertebral disc until it penetrates the annulus fibrosus and enters the nucleus pulposus. The shaft distal end in introduced into the nucleus pulposus, and a portion of the nucleus pulposus is ablated. These and other stages of the procedure may be performed under fluoroscopy to allow visualization of the relative location of the introducer needle and shaft relative to the nucleus pulposus of the disc. Additionally or alternatively, the surgeon may introduce the introducer needle into the nucleus pulposus from a first side of the disc, then advance the shaft distal end through the nucleus pulposus until resistance to axial translation of the electrosurgical probe is encountered by the surgeon. Such resistance may be interpreted by the surgeon as the shaft distal end having contacted the annulus fibrosus at the opposite side of the disc. Then, by use of depth markings on the shaft (FIG. 32A), the surgeon can retract the shaft a defined distance in order to position the shaft distal end at a desired location relative to the nucleus pulposus. Once the shaft distal end is suitably positioned, high frequency voltage may be applied to the probe via the power supply unit.

After step 1206, optional step 1208 involves coagulating at least a portion of the disc tissue. In one embodiment, step 1206 results in the formation of a channel or cavity within the nucleus pulposus. Thereafter, tissue at the surface of the channel may be coagulated during step 1208. Coagulation of disc tissue may be performed by application of a second high frequency voltage, as described hereinabove. After step 1206 or step 1208, the shaft may be moved (step 1210) such that the shaft distal end contacts fresh tissue of the nucleus pulposus. The shaft may be axially translated (i.e. moved in the direction of its longitudinal axis), may be rotated about its longitudinal axis, or may be moved by a combination of axial and rotational movement. In the latter case, a substantially spiral path is defined by the shaft distal end. After step 1210, steps 1206 and 1208 may be repeated with respect to the fresh tissue of the nucleus pulposus contacted by the shaft distal end. Alternatively, after step 1206 or step 1208, the shaft may be withdrawn from the disc (step 1212). Step 1214 involves withdrawing the introducer needle from the disc. In one embodiment, the shaft and the needle may be withdrawn from the disc concurrently. Withdrawal of the shaft from the disc may facilitate exhaustion of ablation by-products from the disc. Such ablation by-products include low molecular weight gaseous compounds derived from molecular dissociation of disc tissue components, as described hereinabove. The above method may be used to treat any disc disorder in which Coblation® and or coagulation of disc tissue is indicated, including contained herniations. In one embodiment, an introducer needle may be introduced generally as described for step 1200, and a fluoroscopic fluid may be introduced through the lumen of the introducer needle for the purpose of visualizing and diagnosing a disc abnormality or disorder. Thereafter, depending on the diagnosis, a treatment procedure may be performed, e.g., according to steps 1202 through 1214, using the same introducer needle as access. In one embodiment, a distal portion, or the entire length, of the introducer needle may have an insulating coating on its external surface. Such an insulating coating on the introducer needle may prevent interference between the electrically conductive introducer needle and electrode(s) on the probe.

The size of the cavity or channel formed in a tissue by a single straight pass of the shaft through the tissue to be ablated is a function of the diameter of the shaft (e.g., the diameter of the shaft distal end and active electrode) and the amount of axial translation of the shaft. (By a "single straight pass" of the shaft is meant one axial translation of the shaft in a distal direction through the tissue, in the absence of rotation of the shaft about the longitudinal axis of the shaft, with the power from the power supply turned on.) In the case of a curved shaft, according to various embodiments of the instant invention, a larger channel can be formed by rotating the shaft as it is advanced through the tissue. The size of a channel formed in a tissue by a single rotational pass of the shaft through the tissue to be ablated is a function of the deflection of the shaft, and the amount of rotation of the shaft about its longitudinal axis, as well as the diameter of the shaft (e.g., the diameter of the shaft distal end and active electrode) and the amount of axial translation of the shaft. (By a "single rotational pass" of the shaft is meant one axial translation of the shaft in a distal direction through the tissue, in the presence of rotation of the shaft about the longitudinal axis of the shaft, with the power from the power supply turned on.) To a large extent, the diameter of a channel formed during a rotational pass of the shaft through tissue can be controlled by the amount of rotation of the shaft, wherein the "amount of rotation" encompasses both the rate of rotation (e.g., the angular velocity of the shaft), and the number of degrees through which the shaft is rotated (e.g. the number of turns) per unit length of axial movement. Typically, according to the invention, the amount of axial translation per pass (for either a straight pass or a rotational pass) is not limited by the length of the shaft. Instead, the amount of axial translation per single pass is preferably determined by the size of the tissue to be ablated. Depending on the size of the disc or other tissue to be treated, and the nature of the treatment, etc., a channel formed by a probe of the instant invention may preferably have a length in the range of from about 2 mm to about 50 mm, and a diameter in the range of from about 0.5 mm to about 7.5 mm. In comparison, a channel formed by a shaft of the instant invention during a single rotational pass may preferably have a diameter in the range of from about 1.5 mm to about 25 mm.

Figure 40:
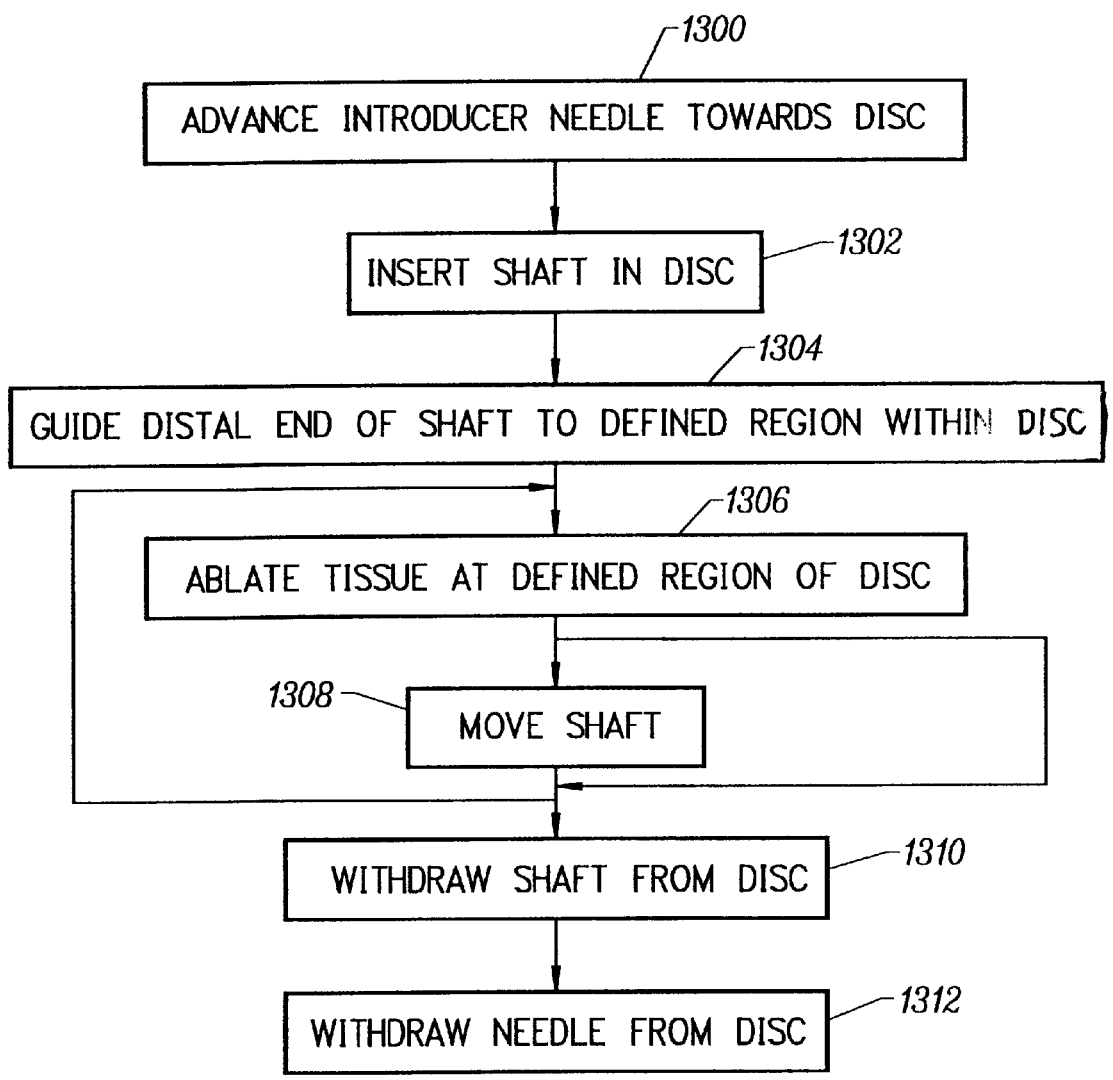
FIG. 40 schematically represents a series of steps involved in a method of guiding an electrosurgical probe to a target site within an intervertebral disc for ablation of targeted disc tissue, according to another embodiment of the invention.

A channel formed by a shaft of the instant invention during a single straight pass may preferably have a volume in the range of from about 1 $mm^3$, or less, to about 2,500 $mm^3$. More preferably, a channel formed by a straight pass of a shaft of the instant invention has a volume in the range of from about 10 $mm^3$ to about 2,500 $mm^3$, and more preferably in the range of from about 50 $mm^3$ to about 2,500 $mm^3$. In comparison, a channel formed by a shaft of the instant invention during a single rotational pass typically has a volume from about twice to about 15 times the volume of a channel of the same length formed during a single rotational pass, i.e., in the range of from about 2 $mm^3$ to about 4,000 $mm^3$, more preferably in the range of from about 50 $mm^3$ to about 2,000 $mm^3$. While not being bound by theory, the reduction in volume of a disc having one or more channels therein is a function of the total volume of the one or more channels. FIG. 40 schematically represents a series of steps involved in a method of guiding the distal end of a shaft of an electrosurgical probe to a target site within an intervertebral disc for ablation of specifically targeted disc tissue, wherein steps 1300 and 1302 are analogous to steps 1200 and 1204 of FIG. 39. Thereafter step 1304 involves guiding the shaft distal end to a defined region within the disc. The specific target site may be pre-defined as a result of a previous procedure to visualize the disc and its abnormality, e.g., via X-ray examination, endoscopically, or fluoroscopically. As an example, a defined target site within a disc may comprise a fragment of the nucleus pulposus that has migrated within the annulus fibrosus (see, e.g., FIG. 36D) resulting in discogenic pain. However, guiding the shaft to defined sites associated with other types of disc disorders are also possible and is within the scope of the invention.

Guiding the shaft distal end to the defined target site may be performed by axial and/or rotational movement of a curved shaft, as described hereinabove. Or the shaft may be steerable, for example, by means of a guide wire, as is well known in the art. Guiding the shaft distal end may be performed during visualization of the location of the shaft relative to the disc, wherein the visualization may be performed endoscopically or via fluoroscopy. Endoscopic examination may employ a fiber optic cable (not shown). The fiber optic cable may be integral with the electrosurgical probe, or be part of a separate instrument (endoscope). Step 1306 involves ablating disc tissue, and is analogous to step 1206 (FIG. 39). Before or during step 1306, an electrically conductive fluid may be applied to the disc tissue and/or the shaft in order to provide a path for current flow between active and return electrodes on the shaft, and to facilitate and/or maintain a plasma in the vicinity of the distal end portion of the shaft. After the shaft distal end has been guided to a target site and tissue at that site has been ablated, the shaft may be moved locally, e.g., within the same region of the nucleus pulposus, or to a second defined target site within the same disc. The shaft distal end may be moved as described herein (e.g., with reference to step 1210, FIG. 39). Or, according to an alternative embodiment, the shaft may be steerable, e.g., by techniques well known in the art. Steps 1310 and 1312 are analogous to steps 1212 and 1214, respectively (described with reference to FIG. 39).

It is known in the art that epidural steroid injections can transiently diminish perineural inflammation of an affected nerve root, leading to alleviation of discogenic pain. In one embodiment of the invention, methods for ablation of disc tissue described hereinabove may be conveniently performed in conjunction with an epidural steroid injection. For example, ablation of disc tissue and epidural injection could be carried out as part of a single procedure, by the same surgeon, using equipment common to both procedures (e.g. visualization equipment). Combining Coblation® and epidural injection in a single procedure may provide substantial cost-savings to the healthcare industry, as well as a significant improvement in patient care.

As alluded to hereinabove, methods and apparatus of the present invention can be used to accelerate the healing process of intervertebral discs having fissures and/or contained herniations. In one method, the present invention is useful in microendoscopic discectomy procedures, e.g., for decompressing a nerve root with a lumbar discectomy. For example, as described above in relation to FIGS. 18–20, a percutaneous penetration can be made in the patient's back so that the superior lamina can be accessed. Typically, a small needle is used initially to localize the disc space level, and a guide wire is inserted and advanced under lateral fluoroscopy to the inferior edge of the lamina. Sequential cannulated dilators can be inserted over the guide wire and each other to provide a hole from the incision to the lamina. The first dilator may be used to "palpate" the lamina, assuring proper location of its tip between the spinous process and facet complex just above the inferior edge of the lamina. A tubular retractor can then be passed over the largest dilator down to the lamina. The dilators can then be removed, so as to establish an operating corridor within the tubular retractor. It should be appreciated however, that other conventional or proprietary methods can be used to access the target intervertebral disc. Once the target intervertebral disc has been accessed, an introducer device may be inserted into the intervertebral disc.

With reference to FIG. 41, in one embodiment, both introducer needle 928 and a second or ancillary introducer 938 may be inserted into the same disc, to allow introduction of an ancillary device 940 into the target disc via ancillary introducer 938. Ancillary device 940 may comprise, for example, a fluid delivery device, a return electrode, an aspiration lumen, a second electrosurgical probe, or an endoscope having an optical fiber component. Each of introducer needle 928 and ancillary introducer 938 may be advanced through the annulus fibrosus until at least the distal end portion of each introducer 928 and 938, is positioned within the nucleus pulposus. Thereafter, shaft 902" of electrosurgical probe 900' may be inserted through at least one of introducers 928, 938, to treat the intervertebral disc. Typically, shaft 902" of probe 900' has an outer diameter no larger than about 7 French (1 Fr: 0.33 mm), and preferably between about 6 French and 7 French.

Prior to inserting electrosurgical probe 900 into the intervertebral disc, an electrically conductive fluid can be delivered into the disk via a fluid delivery assembly (e.g., ancillary device 940) in order to facilitate or promote the Coblation® mechanism within the disc following the application of a high frequency voltage via probe 900'. By providing a separate device (940) for fluid delivery, the dimensions of electrosurgical probe 900' can be kept to a minimum. Furthermore, when the fluid delivery assembly is positioned within ancillary introducer 938, electrically conductive fluid can be conveniently replenished to the interior of the disc at any given time during the procedure. Nevertheless, in other embodiments, the fluid delivery assembly can be physically coupled to electrosurgical probe 900'.

In some methods, a radiopaque contrast solution (not shown) may be delivered through a fluid delivery assembly so as to allow the surgeon to visualize the intervertebral disc under fluoroscopy. In some configurations, a tracking device 942 can be positioned on shaft distal end portion 902"*a*. Additionally or alternatively, shaft 902" can be marked incrementally, e.g., with depth markings 903, to indicate to the surgeon how far the active electrode is advanced into the intervertebral disc. In one embodiment, tracking device 942 includes a radiopaque material that can be visualized under fluoroscopy. Such a tracking device 942 and depth markings 903 provide the surgeon with means to track the position of the active electrode 910 relative to a specific target site within the disc to which active electrode 910 is to be guided. Such specific target sites may include, for example, an annular fissure, a contained herniation, or a fragment of nucleus pulposus. The surgeon can determine the position of the active electrode 910 by observing the depth markings 903, or by comparing tracking device output, and a fluoroscopic image of the intervertebral disc to a pre-operative fluoroscopic image of the target intervertebral disc.

In other embodiments, an optical fiber (not shown) can be introduced into the disc. The optical fiber may be either integral with probe 900' or may be introduced as part of an ancillary device 940 via ancillary introducer 938. In this manner, the surgeon can visually monitor the interior of the intervertebral disc and the position of active electrode 910.

In addition to monitoring the position of the distal portion of electrosurgical probe 900', the surgeon can also monitor whether the probe is in Coblation® mode. In most embodiments, power supply 28 (e.g., FIG. 1) includes a controller having an indicator, such as a light, an audible sound, or a liquid crystal display (LCD), to indicate whether probe 900' is generating a plasma within the disc. If it is determined that the Coblation® mechanism is not occurring, (e.g., due to an insufficiency of electrically conductive fluid within the disc), the surgeon can then replenish the supply of the electrically conductive fluid to the disc.

Figure 42:
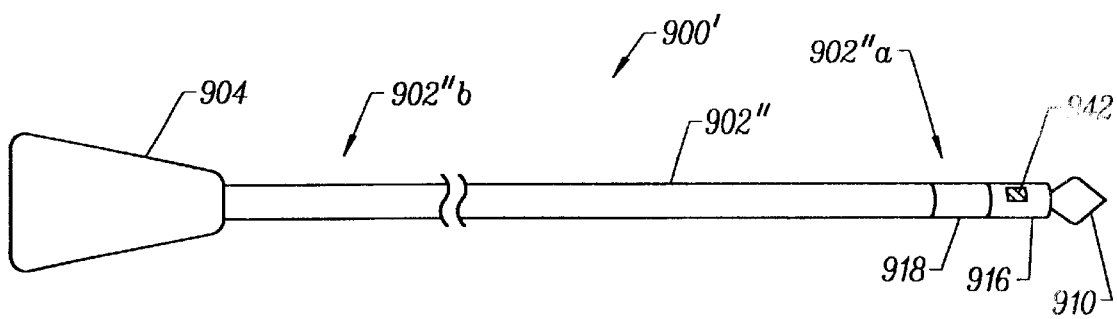
FIG. 42 is a side view of an electrosurgical probe having a tracking device;.

FIG. 42 is a side view of an electrosurgical probe 900' including shaft 902" having tracking device 942 located at distal end portion 902"*a*. Tracking device 942 may serve as a radiopaque marker adapted for guiding distal end portion 902"*a* within a disc. Shaft 902" also includes at least one active electrode 910 disposed on the distal end portion 902"*a*. Preferably, electrically insulating support member or collar 916 is positioned proximal of active electrode 910 to insulate active electrode 910 from at least one return electrode 918. In most embodiments, the return electrode 918 is positioned on the distal end portion of the shaft 902" and proximal of the active electrode 910. In other embodiments, however, return electrode 918 can be omitted from shaft 902", in which case at least one return electrode may be provided on ancillary device 940, or the return electrode may be positioned on the patient's body, as a dispersive pad (not shown).

Although active electrode 910 is shown in FIG. 42 as comprising a single apical electrode, other numbers, arrangements, and shapes for active electrode 910 are within the scope of the invention. For example, active electrode 910 can include a plurality of isolated electrodes in a variety of shapes. Active electrode 910 will usually have a smaller exposed surface area than return electrode 918, such that the current density is much higher at active electrode 910 than at return electrode 918. Preferably, return electrode 918 has a relatively large, smooth surfaces extending around shaft 902" in order to reduce current densities in the vicinity of return electrode 918, thereby minimizing damage to non-target tissue.

While bipolar delivery of a high frequency energy is the preferred method of debulking the nucleus pulposus, it should be appreciated that other energy sources (i.e., resistive, or the like) can be used, and the energy can be delivered with other methods (i.e., monopolar, conductive, or the like) to debulk the nucleus.

Figure 43A:
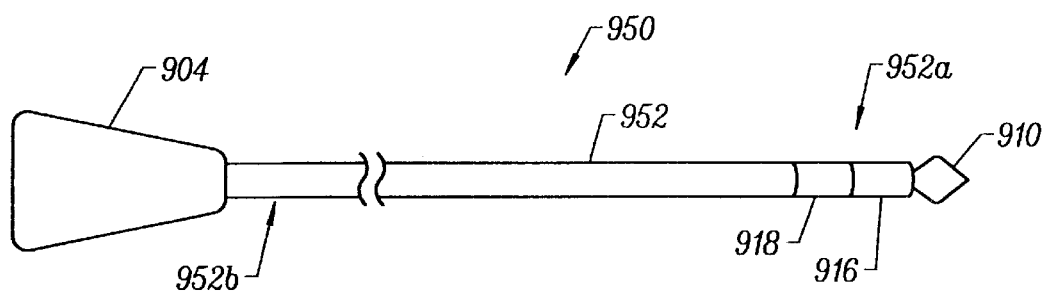
FIG. 43A shows a steerable electrosurgical probe wherein the shaft of the probe assumes a substantially linear configuration.
Figure 43B:
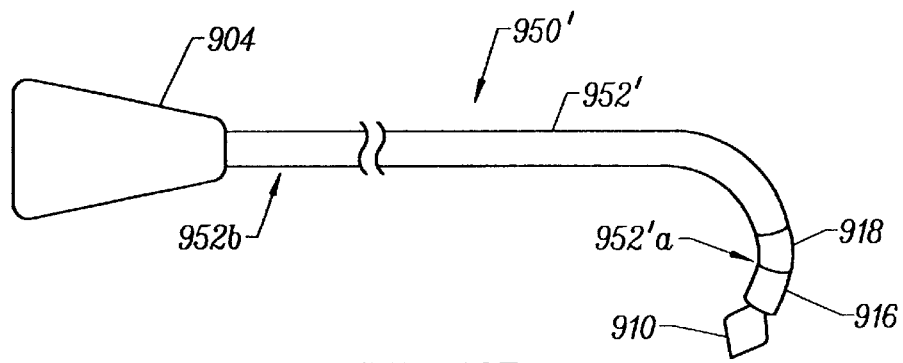
FIG. 43B shows the steerable electrosurgical probe of FIG. 44A, wherein the shaft distal end of the probe adopts a bent configuration.

FIG. 43A shows a steerable electrosurgical probe 950 including a shaft 952, according to another embodiment of the invention. Preferably, shaft 952 is flexible and may assume a substantially linear configuration as shown. Probe 950 includes handle 904, shaft distal end 952a, active electrode 910, insulating collar 916, and return electrode 918. As can be seen in FIG. 43B, under certain circumstances, e.g., upon application of a force to shaft 952 during guiding or steering probe 950 during a procedure, shaft distal end 952a can adopt a non-linear configuration, designated 952'a. The deformable nature of shaft distal end 952'a allows active electrode 910 to be guided to a specific target site within a disc.

Figure 44:
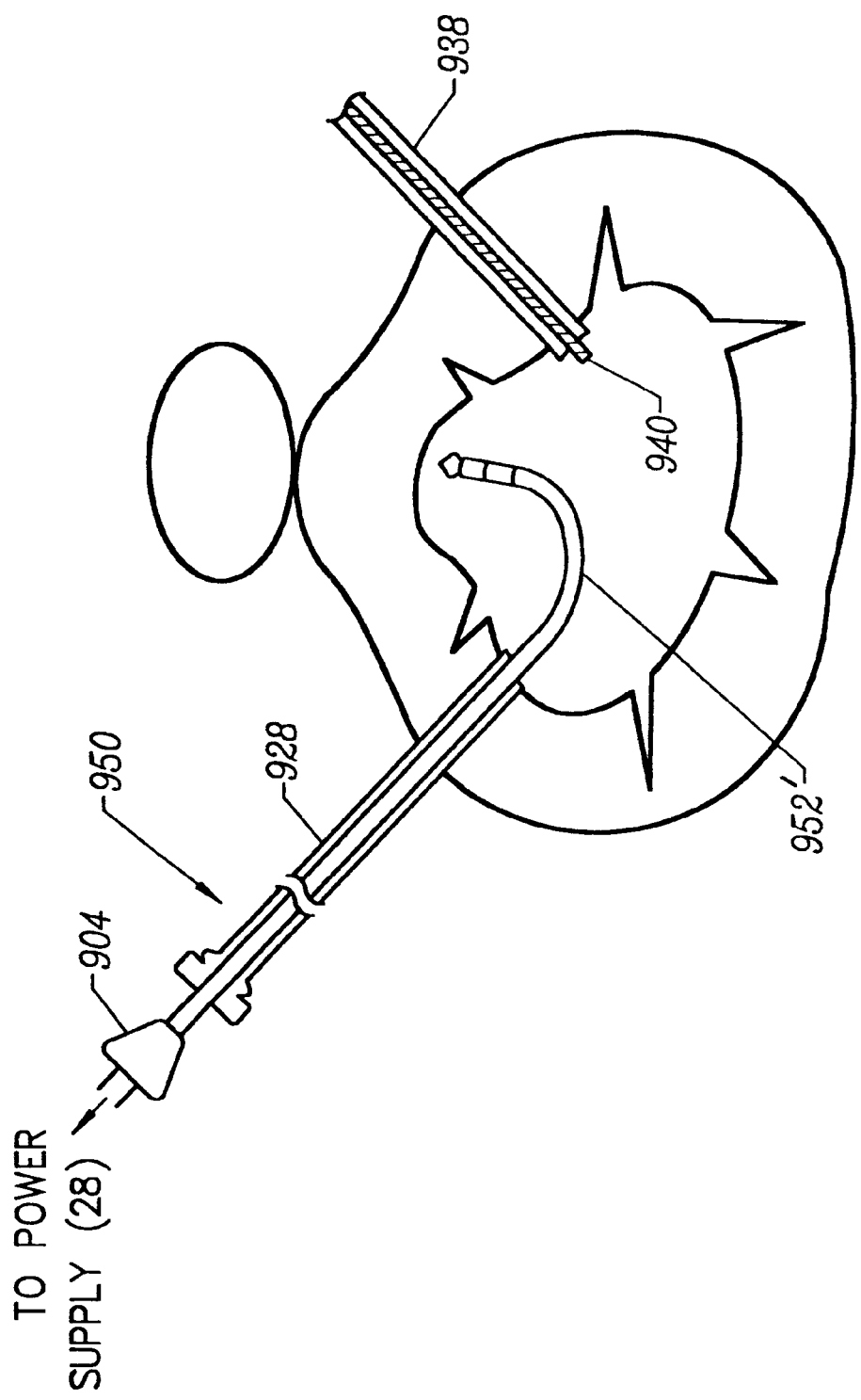
FIG. 44 shows a steerable electrosurgical probe and an ancillary device inserted within the nucleus pulposus of an intervertebral disc.

FIG. 44 shows steerable electrosurgical probe 950 inserted within the nucleus pulposus of an intervertebral disc. An ancillary device 940 and ancillary introducer 928 may also be inserted within the nucleus pulposus of the same disc. To facilitate the debulking of the nucleus pulposus adjacent to a contained herniation, shaft 952 (FIG. 43A) can be manipulated to a non-linear configuration, represented as 952'. Preferably, shaft 955/952' is flexible over at least shaft distal end 952a so as to allow steering of active electrode 910 to a position adjacent to the targeted disc abnormality. The flexible shaft may be combined with a sliding outer shield, a sliding outer introducer needle, pull wires, shape memory actuators, and other known mechanisms (not shown) for effecting selective deflection of distal end 952a to facilitate positioning of active electrode 910 within a disc. Thus, it can be seen that the embodiment of FIG. 44 may be used for the targeted treatment of annular fissures, or any other disc abnormality in which Coblation® is indicated.

In one embodiment shaft 952 has a suitable diameter and length to allow the surgeon to reach the target disc or vertebra by introducing the shaft through the thoracic cavity, the abdomen or the like. Thus, shaft 952 may have a length in the range of from about 5.0 cm to 30.0 cm, and a diameter in the range of about 0.2 mm to about 20 mm. Alternatively, shaft 952 may be delivered percutaneously in a posterior lateral approach. Regardless of the approach, shaft 952 may be introduced via a rigid or flexible endoscope. In addition, it should be noted that the methods described with reference to FIGS. 41 and 44 may also be performed in the absence of ancillary introducer 938 and ancillary device 940.

Although the invention has been described primarily with respect to electrosurgical treatment of intervertebral discs, it is to be understood that the methods and apparatus of the invention are also applicable to the treatment of other tissues, organs, and bodily structures. For example, the principle of the "S-curve" configuration of the invention may be applied to any medical system or apparatus in which a medical instrument is passed within an introducer device, wherein it is desired that the distal end of the medical instrument does not contact or impinge upon the introducer device as the instrument is advanced from or retracted within the introducer device. The introducer device may be any apparatus through which a medical instrument is passed. Such a medical system or apparatus may include, for example, a catheter, a cannula, an endoscope, and the like. Thus, while the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. A method of treating an inter-vertebral disc, comprising:
    a) contacting at least a first region of a nucleus pulposus of the inter-vertebral disc with at least one active electrode of an electrosurgical system, the at least one active electrode disposed on a shaft of an electrosurgical probe, and the at least one active electrode functionally coupled to a power supply unit; and
    b) applying a first high frequency voltage between the at least one active electrode and at least one return electrode, wherein at least a portion of the nucleus pulposus is ablated and the volume of the nucleus pulposus is decreased.

2. The method of claim 1, further comprising:
    c) contacting at least a second region of the nucleus pulposus of the inter-vertebral disc with the at least one active electrode, and thereafter, repeating said step b).

3. The method of claim 1, wherein during said step b), the at least one active electrode is translated within the nucleus pulposus, wherein a channel is formed within the nucleus pulposus, and translation of the at least one active electrode within the nucleus pulposus is implemented via movement of the probe.

4. The method of claim 3, wherein movement of the probe is selected from the group consisting of axial movement, rotational movement, and concurrent axial and rotational movement.

5. The method of claim 1, wherein said steps a) and b) result in formation of a channel within the nucleus pulposus, the channel having a channel wall, and the method further comprises:
    d) positioning the at least one active electrode adjacent to the channel wall; and
    e) coagulating tissue of the nucleus pulposus by applying a second high frequency voltage between the at least one active electrode and the at least one return electrode.

6. The method of claim 5, wherein tissue at the channel wall is coagulated, and the nucleus pulposus undergoes a physical change selected from the group consisting of stiffening, increased rigidity, increased strength, decrease in volume, and decrease in mass.

7. The method of claim 5, wherein the first high frequency voltage is in the range of from about 150 to about 700 volts rms, and the second high frequency voltage is in the range of from about 20 to about 150 volts rms.

8. The method of claim 5, wherein the first high frequency voltage is in the range of from about 150 to about 350 volts rms, and the second high frequency voltage is in the range of from about 20 to about 90 volts rms.

9. The method of claim 1, wherein the at least one active electrode and the at least one return electrode are disposed on a distal end of the shaft, and the at least one return electrode is spaced proximally from the at least one active electrode.

10. The method of claim 1, further comprising the step of:
   f) prior to said step b), providing an electrically conductive fluid at the at least a first region of the nucleus pulposus.

11. The method of claim 10, wherein said step f) comprises applying the electrically conductive fluid to the at least one active electrode, or applying the electrically conductive fluid to the disc.

12. The method of claim 10, wherein the at least one active electrode and the at least one return electrode are disposed on a distal end of the shaft, and the at least one return electrode is spaced proximally from the at least one active electrode, and the electrically conductive fluid provides an electrically conductive path between the at least one active electrode and the at least one return electrode.

13. The method of claim 1, wherein the shaft includes a shaft distal end, and the shaft distal end is introduced into the nucleus pulposus via an introducer needle, the introducer needle includes a lumen and a needle distal end, the shaft distal end includes at least one curve therein, and the shaft distal end is retractable into the lumen without contacting the needle distal end.

14. The method of claim 1, wherein the shaft is visualized fluoroscopically or endoscopically.

15. The method of claim 1, wherein the at least one active electrode comprises an electrode head having a substantially apical spike and a substantially equatorial cusp, and the shaft includes an insulating collar located proximal to the electrode head.

16. The method of claim 15, wherein the insulating collar comprises a material selected from the group consisting of: a ceramic, a glass, and a silicone.

17. The method of claim 1, wherein the at least one active electrode includes a filament, the shaft includes a first insulating sleeve encasing the filament, a return electrode on the first insulating sleeve, and a second insulating sleeve on the return electrode.

18. The method of claim 1, wherein the shaft includes a shield encasing the shaft, wherein the shield decreases the amount of leakage current passing from the electrosurgical probe.

19. The method of claim 1, wherein the shaft includes a first curve and a second curve proximal to the first curve, the first curve and the second curve are in the same plane relative to the longitudinal axis of the shaft, and the first curve and the second curve are in different directions relative to the longitudinal axis of the shaft, the first curve is characterized by a first angle and the second curve is characterized by a second angle, wherein the first angle is less than the second angle.

20. The method of claim 1, wherein decreasing the volume of the nucleus pulposus relieves pressure exerted by the nucleus pulposus on an annulus fibrosus.

21. The method of claim 1, wherein decreasing the volume of the nucleus pulposus decompresses at least one nerve or nerve root, and discogenic pain is alleviated.

22. The method of claim 1, wherein during said step b), the at least one active electrode is axially translated within the nucleus pulposus to form a channel within the nucleus pulposus, wherein the channel is formed by a single straight pass of the shaft in the nucleus pulposus, and the channel has a volume in the range of from about 1 $mm^3$ to about 2,500 $mm^3$.

23. The method of claim 22, wherein the channel has a volume in the range of from about 10 $mm^3$ to about 2,500 $mm^3$.

24. The method of claim 22, wherein the channel has a diameter in the range of from about 0.5 mm to about 7.5 mm.

25. The method of claim 22, wherein the channel has a length in the range of from about 2 mm to about 50 mm.

26. The method of claim 1, wherein during said step b), the at least one active electrode is axially translated within the nucleus pulposus and concurrently therewith the shaft is rotated about its longitudinal axis, wherein the at least one active electrode forms a channel within the nucleus pulposus, the channel is formed by a single rotational pass of the shaft, wherein the at least one active electrode is disposed on a distal end of the shaft, the shaft includes at least one curve, and the channel has a volume in the range of from about 2 $mm^3$ to about 38,000 $mm^3$.

27. The method of claim 26, wherein the channel has a volume in the range of from about 50 $mm^3$ to about 10,000 $mm^3$.

28. The method of claim 1, wherein the shaft has a length in the range of from about 4 cm to about 30 cm, and the shaft has a diameter in the range of from about 0.5 mm to about 2.5 mm.

29. The method of claim 1, wherein the shaft includes a shaft distal end, and wherein the shaft distal end is introduced into the nucleus pulposus via an introducer needle, the introducer needle including a lumen, wherein the introducer needle has a length in the range of from about 3 cm to about 25 cm, and the lumen has a diameter in the range of from about 0.5 mm to about 2.5 mm.

30. The method of claim 1, wherein the method is performed percutaneously, and the at least a portion of the nucleus pulposus is ablated at a temperature in the range of from about 45° C. to about 90° C.

31. The method of claim 1, wherein the intervertebral disc is a lumbar disc, and the shaft has a length in the range of from about 10 cm to about 25 cm.

32. The method of claim 1, wherein the intervertebral disc is a cervical disc, and the shaft has a length in the range of from about 4 cm to about 15 cm.

33. A method of treating an inter-vertebral disc, comprising:
   providing an electrosurgical system including a probe and a power supply unit, wherein the probe includes a shaft and a handle, the shaft including a distal end portion, at least one active electrode, and at least one return electrode, the at least one active electrode located on the distal end portion of the shaft, the distal end portion of the shaft having a pre-defined bias in the longitudinal direction thereof;
   inserting the distal end portion of the shaft within the disc; and
   ablating at least a portion of nucleus pulposus tissue from the disc, wherein at least one channel is formed within the nucleus pulposus.

34. The method of claim 33, wherein said ablating step comprises applying a first high frequency voltage between the at least one active electrode and the at least one return electrode, wherein a plasma is formed in the vicinity of the at least one active electrode, high molecular weight components of the nucleus pulposus tissue undergo molecular dissociation to form low molecular weight gaseous materials, and the volume of the nucleus pulposus is decreased.

35. The method of claim 33, wherein said ablating step comprises ablating the nucleus pulposus tissue at a temperature in the range of from about 45° C. to about 90° C.

36. The method of claim 33, wherein said ablating step results in the production of ablation by-products, and the ablation by-products are aspirated from the disc by a suction device.

37. The method of claim 34, further comprising the step of:

removing the shaft from the disc, wherein said removing step causes the low molecular weight gaseous materials to be exhausted from the disc.

38. The method of claim 33, wherein said ablating step causes localized ablation of targeted disc tissue with minimal collateral damage to non-target tissue within the disc.

39. The method of claim 33, wherein said ablating step comprises applying a first high frequency voltage between the at least one active electrode and the at least one return electrode, and the method further comprises:

after said ablating step, applying a second high frequency voltage between the at least one active electrode and the at least one return electrode, wherein the second high frequency voltage is sufficient to coagulate disc tissue adjacent to the distal end portion of the shaft.

40. The method of claim 33, further comprising:

before said ablating step, contacting the at least one active electrode with a quantity of an electrically conductive fluid.

41. The method of claim 33, wherein said inserting step comprises advancing the shaft distal end portion via an introducer needle having a lumen and a needle distal end, wherein the shaft distal end portion is advanced distally beyond the needle distal end, wherein the at least one active electrode does not make contact with the needle distal end; and the method further comprises retracting the shaft distal end portion proximally within the lumen of the introducer needle, wherein the at least one active electrode does not make contact with the needle distal end.

42. The method of claim 33, wherein the shaft includes a shield, the shaft distal end portion includes a first curve, a second curve proximal to the first curve, and an insulating collar distal to the first curve, and the at least one active electrode comprises a filament and a head having an apical spike and an equatorial cusp.

43. A method of treating an inter-vertebral disc with an electrosurgical system, the electrosurgical system including a probe having a shaft, the shaft including a shaft distal end portion, an active electrode disposed on the shaft distal end portion, and a return electrode disposed proximal to the active electrode, the method comprising:

a) contacting a nucleus pulposus of the disc with the active electrode;

b) applying a high frequency voltage between the active electrode and the return electrode, wherein the high frequency voltage is sufficient to ablate disc tissue; and c) during the applying step, translating the shaft distal end portion within the nucleus pulposus, wherein tissue of the nucleus pulposus is ablated and the volume of the nucleus pulposus is decreased.

44. The method of claim 43, wherein the shaft distal end portion includes a first curve and a second curve proximal to the first curve, wherein the first curve allows the active electrode to be retracted within an introducer needle without contacting the introducer needle.

45. The method of claim 44, wherein the second curve allows the active electrode to contact fresh tissue within the nucleus pulposus when the shaft is rotated about its longitudinal axis.

46. The method of claim 43, wherein the active electrode includes an electrode head having a substantially equatorial cusp and an apical spike, wherein the apical spike promotes high current density at the active electrode and facilitates axial translation of the shaft distal end portion within a tissue.

47. The method of claim 43, wherein the method is performed percutaneously, and the shaft distal end portion is introduced into the disc via an introducer needle.

48. The method of claim 43, wherein decrease in the volume of the nucleus pulposus leads to decompression of a nerve root and alleviation of discogenic pain.

49. The method of claim 48, wherein the discogenic pain is caused by a contained herniation, an annular fissure, or fragmentation of the nucleus pulposus.

50. The method of claim 43, further comprising:

d) inserting an ancillary introducer needle into the disc; and e) advancing, via the ancillary introducer needle, an ancillary device into the nucleus pulposus, wherein the ancillary device comprises an endoscope, an optical fiber, an aspiration device, a fluid delivery assembly, or a return electrode.

51. The method of claim 43, wherein the shaft distal end portion includes a tracking device for indicating a location of the shaft distal end portion relative to the nucleus pulposus.

52. The method of claim 43, wherein the shaft includes at least one depth marking for indicating a location of the shaft distal end portion relative to the nucleus pulposus.

53. The method of claim 43, wherein said contacting step comprises:

f) advancing the shaft distally through the nucleus pulposus until the shaft distal end portion contacts an inner wall of an annulus fibrosus; and thereafter, retracting the shaft a defined distance.

54. The method of claim 43, further comprising the step of:

g) determining a depth of penetration of the shaft distal end portion within the disc.

55. The method of claim 54, wherein the shaft distal end portion is introduced into the disc via an introducer needle having an introducer proximal end, and said step g) comprises monitoring the position of the introducer proximal end relative to a mechanical stop or at least one depth marking.

56. The method of claim 54, wherein said step g) comprises:

h) advancing the shaft distal end portion through the nucleus pulposus until the shaft distal end portion contacts the annulus fibrosus; and thereafter, i) retracting the shaft distal end portion a defined distance.

57. The method of claim 55, wherein said step g) comprises:

h) advancing the shaft distal end portion through the nucleus pulposus until the mechanical stop contacts a proximal end of the introducer needle.

* * * * *